United States Patent
Frank et al.

(10) Patent No.: US 11,542,328 B2
(45) Date of Patent: *Jan. 3, 2023

(54) THERAPEUTIC AND DIAGNOSTIC METHODS RELATING TO CANCER STEM CELLS

(71) Applicant: Children's Medical Center Corporation, Boston, MA (US)

(72) Inventors: Markus H. Frank, Cambridge, MA (US); Natasha Y. Frank, Cambridge, MA (US)

(73) Assignees: The Brigham and Women's Hospital, Inc., Boston, MA (US); Children's Medical Center Corporation, Boston, MA (US)

( * ) Notice: Subject to any disclaimer, the term of this patent is extended or adjusted under 35 U.S.C. 154(b) by 425 days.

This patent is subject to a terminal disclaimer.

(21) Appl. No.: 16/435,929

(22) Filed: Jun. 10, 2019

(65) Prior Publication Data

US 2020/0385464 A1 Dec. 10, 2020
US 2021/0355210 A9 Nov. 18, 2021

Related U.S. Application Data

(63) Continuation of application No. 14/868,126, filed on Sep. 28, 2015, now Pat. No. 10,316,085, which is a continuation of application No. 13/128,915, filed as application No. PCT/US2009/006089 on Nov. 13, 2009, now abandoned.

(60) Provisional application No. 61/114,490, filed on Nov. 14, 2008.

(51) Int. Cl.

| | | |
|---|---|---|
| A61K 39/00 | (2006.01) | |
| C07K 16/28 | (2006.01) | |
| C12N 15/113 | (2010.01) | |
| G01N 33/574 | (2006.01) | |
| A61K 51/10 | (2006.01) | |
| A61K 38/17 | (2006.01) | |

(52) U.S. Cl.
CPC ...... *C07K 16/2803* (2013.01); *A61K 38/1709* (2013.01); *A61K 51/1096* (2013.01); *C12N 15/1138* (2013.01); *G01N 33/57415* (2013.01); *G01N 33/57419* (2013.01); *G01N 33/57434* (2013.01); *C07K 2317/24* (2013.01); *C07K 2317/51* (2013.01); *C07K 2317/54* (2013.01); *C07K 2317/55* (2013.01); *C07K 2317/56* (2013.01); *C07K 2317/76* (2013.01); *C12N 2310/122* (2013.01); *C12N 2310/14* (2013.01); *C12N 2310/3513* (2013.01)

(58) Field of Classification Search
CPC ............ C07K 16/2803; C07K 2317/24; C07K 2317/51; C07K 2317/54; C07K 2317/56; C07K 2317/622; C07K 2317/76; A61K 38/1709; A61K 51/1096; C12N 15/1138
See application file for complete search history.

(56) References Cited

U.S. PATENT DOCUMENTS

| | | |
|---|---|---|
| 5,399,483 A | 3/1995 | Shibano et al. |
| 5,434,075 A | 7/1995 | Mechetner et al. |
| 5,612,185 A | 3/1997 | Uhr et al. |
| 6,008,002 A | 12/1999 | Bodey |
| 6,152,142 A | 11/2000 | Tseng |
| 6,846,883 B2 | 1/2005 | Frank et al. |
| 6,875,430 B2 | 4/2005 | McIntosh et al. |
| 6,899,873 B2 | 5/2005 | Ma et al. |
| 6,905,678 B2 | 6/2005 | Havenga et al. |
| 7,029,666 B2 | 4/2006 | Bruder et al. |
| 7,202,346 B2 | 4/2007 | Payne et al. |
| 7,465,554 B2 | 12/2008 | Frank et al. |
| 7,928,202 B2 | 4/2011 | Frank et al. |
| 8,076,091 B2 | 12/2011 | Frank et al. |
| 8,425,876 B2 | 4/2013 | Frank et al. |
| 8,455,245 B2 | 6/2013 | Frank et al. |
| 8,507,273 B2 | 8/2013 | Frank et al. |
| 8,697,072 B2 | 4/2014 | Frank et al. |
| 9,266,946 B2 | 2/2016 | Frank et al. |
| 9,561,264 B2 | 2/2017 | Frank et al. |
| 9,801,912 B2 | 10/2017 | Frank et al. |

(Continued)

FOREIGN PATENT DOCUMENTS

| | | |
|---|---|---|
| CN | 105734075 A | 7/2016 |
| EP | 0 174 810 A2 | 3/1986 |

(Continued)

OTHER PUBLICATIONS

U.S. Appl. No. 17/050,424, filed Oct. 23, 2020, Frank.

(Continued)

*Primary Examiner* — Lei Yao
(74) *Attorney, Agent, or Firm* — Wolf, Greenfield & Sacks, P.C.

(57) ABSTRACT

The present invention relates in part to the discovery of genes that are deregulated in cancer stem cells (e.g., melanoma stem cells). In some aspects, methods for treating individuals having melanoma are provided; the methods involve modulating (e.g., inducing, inhibiting, etc.) the activity of the cancer stem cell associated genes. In other aspects, cell surface genes that are upregulated in melanoma stem cells are targeted for the selective isolation, detection, and killing of cancer stem cells in melanoma. Other aspects of the invention relate to reagents, arrays, compositions, and kits that are useful for diagnosing and treating melanoma.

18 Claims, 4 Drawing Sheets

Specification includes a Sequence Listing.

(56) References Cited

U.S. PATENT DOCUMENTS

| | | | |
|---|---|---|---|
| 9,855,342 B2 | 1/2018 | Frank et al. | |
| 10,017,738 B2 | 7/2018 | Frank et al. | |
| 10,316,085 B2 | 6/2019 | Frank et al. | |
| 11,129,854 B2 | 9/2021 | Frank et al. | |
| 2002/0160000 A1* | 10/2002 | Wood | A61P 37/02 424/93.7 |
| 2006/0019256 A1 | 1/2006 | Clarke et al. | |
| 2007/0099209 A1 | 5/2007 | Clarke et al. | |
| 2007/0105133 A1 | 5/2007 | Clarke et al. | |
| 2007/0116691 A1 | 5/2007 | Cambier et al. | |
| 2008/0003206 A1 | 1/2008 | Frank et al. | |
| 2008/0047026 A1 | 2/2008 | Fuchs et al. | |
| 2008/0132423 A1 | 6/2008 | Kondo | |
| 2009/0117117 A1 | 5/2009 | Frank et al. | |
| 2009/0162873 A1 | 6/2009 | Frank et al. | |
| 2010/0145030 A1 | 6/2010 | Frank et al. | |
| 2011/0015090 A1 | 1/2011 | Majeti et al. | |
| 2011/0165149 A1 | 7/2011 | Frank et al. | |
| 2011/0287034 A1 | 11/2011 | Frank et al. | |
| 2012/0034196 A1 | 2/2012 | Frank et al. | |
| 2013/0017175 A1 | 1/2013 | Bartholomew et al. | |
| 2013/0287785 A1 | 10/2013 | Frank et al. | |
| 2013/0315880 A1 | 11/2013 | Frank | |
| 2014/0302031 A1 | 10/2014 | Frank et al. | |
| 2015/0374756 A1 | 12/2015 | Frank et al. | |
| 2016/0009804 A1 | 1/2016 | Frank et al. | |
| 2016/0106782 A1 | 4/2016 | Frank et al. | |
| 2016/0136297 A1 | 5/2016 | Frank et al. | |
| 2018/0064762 A1 | 3/2018 | Frank et al. | |
| 2018/0320131 A1 | 11/2018 | Frank | |
| 2021/0095254 A1 | 4/2021 | Frank et al. | |
| 2021/0188999 A1 | 6/2021 | Frank | |
| 2022/0118024 A1 | 4/2022 | Frank et al. | |
| 2022/0184136 A1 | 6/2022 | Frank et al. | |

FOREIGN PATENT DOCUMENTS

| | | |
|---|---|---|
| EP | 0 267 781 A2 | 5/1988 |
| EP | 1 537 878 A1 | 6/2005 |
| KR | 10-2007-0001108 A | 1/2007 |
| WO | WO 96/04313 | 2/1996 |
| WO | WO 01/23540 A2 | 4/2001 |
| WO | WO 01/23540 A3 | 4/2001 |
| WO | WO 01/098361 A2 | 12/2001 |
| WO | WO 2001/094400 A1 | 12/2001 |
| WO | WO 02/40541 A2 | 5/2002 |
| WO | WO 2004/056875 | 7/2004 |
| WO | WO 2005/005601 A2 | 1/2005 |
| WO | WO 2006/121168 A1 | 11/2006 |
| WO | WO 2006/133396 A2 | 12/2006 |
| WO | WO 2007/112097 A2 | 10/2007 |
| WO | WO 2007/138334 A1 | 12/2007 |
| WO | WO 2008/013492 A1 | 1/2008 |
| WO | WO 2008/079269 A2 | 7/2008 |
| WO | WO 2008/127656 | 10/2008 |
| WO | WO 2009/002440 A2 | 12/2008 |
| WO | WO 2009/009116 A2 | 1/2009 |
| WO | WO 2009/097270 A2 | 8/2009 |
| WO | WO 2009/024531 A1 | 12/2009 |
| WO | WO 2010/065711 A1 | 6/2010 |
| WO | WO 2010/133853 A1 | 11/2010 |
| WO | WO 2011/140828 A1 | 11/2011 |
| WO | WO 2014/182994 A1 | 11/2014 |
| WO | WO 2016/179576 A1 | 11/2016 |
| WO | WO 2018/185584 A1 | 10/2018 |
| WO | WO 2019/210109 A1 | 10/2019 |
| WO | WO 2020/198611 A1 | 10/2020 |
| WO | WO 2020/219895 A1 | 10/2020 |
| WO | WO 2021/076043 A1 | 4/2021 |

OTHER PUBLICATIONS

U.S. Appl. No. 16/835,144, filed Mar. 30, 2020, Frank et al.
U.S. Appl. No. 17/598,848, filed Sep. 27, 2021, Frank et al.
U.S. Appl. No. 17/605,862, filed Oct. 22, 2021, Frank et al.
EP 20156762.5, Sep. 24, 2020, Partial European Search Report.
EP 20156762.5, Jan. 13, 2021, Extended European Search Report.
Extended European Search Report dated Feb. 14, 2014 for EP 09826430.2.
European Summons to attend Oral Proceedings mailed Jan. 27, 2016 for Application No. EP 09826430.2.
European Office Communication dated Jul. 18, 2016 for Application No. EP 09826430.2.
European Office Communication dated Jul. 20, 2016 for Application No. EP 16177814.7.
Extended European Search Report for European Application No. 16177814.7 dated Dec. 20, 2016.
International Search Report and Written Opinion for PCT/US09/06089 dated Mar. 10, 2010.
International Preliminary Report on Patentability for PCT/US09/06089 dated May 26, 2011.
Bork et al., Go hunting in sequence databases but watch out for the traps. Trends Genet. Oct. 1996;12(10):425-7.
Bork, Powers and pitfalls in sequence analysis: the 70% hurdle. Genome Res. Apr. 2000;10(4):398-400.
Chaudhary et al., Expression and activity of P-glycoprotein, a multidrug efflux pump, in human hematopoietic stem cells. Cell. Jul. 12, 1991;66(1):85-94.
Cotsarelis et al., Existence of slow-cycling limbal epithelial basal cells that can be preferentially stimulated to proliferate: implications on epithelial stem cells. Cell. Apr. 21, 1989;57(2):201-9.
Easton et al., Genome-wide association studies in cancer. Hum Mol Genet. Oct. 15, 2008;17(R2):R109-15.
Frank et al. 2005, ABCB5-mediated doxorubicin transport and chemoresistance in human malignant melanoma. Cancer Research. 65:10;4320-4333.
Frank et al., ABCB5 P-glycoprotein is a molecular marker of the Hoechst 33342 side population phenotype among human fetal skeletal muscle cells. FASEB Journal. 2004;18(4-5):A183. Abstract 144.9.
Frank et al., Immunomodulatory functions of mesenchymal stem cells. Lancet. May 1, 2004;363(9419):1411-2.
Frank et al., Regulation of progenitor cell fusion by ABCB5 P-glycoprotein, a novel human ATP-binding cassette transporter. J Biol Chem. Nov. 21, 2003;278(47):47156-65. Epub Sep. 7, 2003.
Frank et al., Specific MDR1 P-glycoprotein blockade inhibits human alloimmune T cell activation in vitro. J Immunol. Feb. 15, 2001;166(4):2451-9.
Frank et al., VEGFR-1 expressed by malignant melanoma-initiating cells is required for tumor growth. Cancer Res. Feb. 15, 2011;71(4):1474-85. Epub Jan. 6, 2011.
Freshney, Culture of Animal Cells, A Manual of Basic Technique. Alan R. Liss, Inc. New York, New York. 1983:3-4.
Gillet et al., Chemotherapy-induced resistance by ATP-binding cassette transporter genes. Biochim Biophys Acta. Jun. 2007;1775(2):237-62. Epub Jun. 6, 2007.
Gold et al., Genome-wide association study provides evidence for a breast cancer risk locus at 6q22.33. Proc Natl Acad Sci U S A. Mar. 15, 2008;105(11):4340-5. doi: 10.1073/pnas.0800441105. Epub Mar. 7, 2008.
Goodell et al., Isolation and functional properties of murine hematopoietic stem cells that are replicating in vivo. J Exp Med. Apr. 1, 1996;183(4):1797-806.
Heimerl et al., Mapping ATP-binding cassette transporter gene expression profiles in melanocytes and melanoma cells. Melanoma Res. Oct. 2007;17(5):265-73.
Herbst et al., Monoclonal antibodies to target epidermal growth factor receptor-positive tumors: a new paradigm for cancer therapy. Cancer. Mar. 1, 2002;94(5):1593-611.
Iwai et al., PD-1 blockade inhibits hematogenous spread of poorly immunogenic tumor cells by enhanced recruitment of effector T cells. Int Immunol. Feb. 2005;17(2):133-44. Epub Dec. 20, 2004.
Jorgensen et al., Engineering mesenchymal stem cells for immunotherapy. Gene Ther. May 2003;10(10):928-31.
Kim et al., Identification of human ABCB5(+) dermal progenitor cells with multipotent differentiation plasticity. Apr. 1, 2010;130(Suppl 1):S107. Abstract.

(56) References Cited

OTHER PUBLICATIONS

Kim et al., MicroRNA Biogenesis: Coordinated Cropping and Dicing. Nat Rev Mol Cell Biol. May 2005;6(5):376-85.
Kleffel et al., ABCB5 inhibition sensitizes Merkel cell carcinoma cells to chemotherapy-induced apoptosis. J Invest Dermatol. 2014;134:S18. Meeting abstract.
Knutsen et al., Cytogenetic and molecular characterization of random chromosomal rearrangements activating the drug resistance gene, MDR1/P-glycoprotein, in drug-selected cell lines and patients with drug refractory ALL. Genes Chromosomes Cancer. Sep. 1998;23(1):44-54.
Lee et al., Integration of genomic analysis and in vivo transfection to identify sprouty 2 as a candidate tumor suppressor in liver cancer. Hepatology. Apr. 2008;47(4):1200-10.
Linster et al., Ethylmalonyl-CoA decarboxylase, a new enzyme involved in metabolite proofreading. J Biol Chem. Dec. 16, 2011;286(50):42992-3003. doi: 10.1074/jbc.M111.281527. Epub Oct. 20, 2011.
Mechetner et al., Efficient inhibition of P-glycoprotein-mediated multidrug resistance with a monoclonal antibody. Proc Natl Acad Sci U S A. Jul. 1, 1992 ;89(13):5824-8.
Meier et al., Progressive decrease in number and change in niche preference of the ABCB5(+) mesenchymal stem cell subset in the skin during aging. Sep. 1, 2010;130(Suppl. 2):S88. Abstract.
Menke et al., Expression analysis of multi drug efflux pump genes in mouse hematopoietic stem and progenitor cells. Blood. 1999;94(10)(Supp 1, Part 1):Abstract#132.
Milenic et al., Cetuximab: preclinical evaluation of a monoclonal antibody targeting EGFR for radioimmunodiagnostic and radioimmunotherapeutic applications. Cancer Biother Radiopharm. Oct. 2008;23(5):619-31. doi: 10.1089/cbr.2008.0493.
Miwa et al., Biological characteristics of CD7(+) acute leukemia. Leuk Lymphoma. Apr. 1996;21(3-4):239-44.
Nomi et al., Clinical significance and therapeutic potential of the programmed death-1 ligand/programmed death-1 pathway in human pancreatic cancer. Clin Cancer Res. Apr. 1, 2007;13(7):2151-7.
Pendse et al., P-Glycoprotein Functions as a Differentiation Switch in Antigen Presenting Cell Maturation. Am J Transplant Dec. 2008; 6(12):2884-93.
Robert, Multidrug resistance in oncology: diagnostic and therapeutic approaches. Eur J Clin Invest. Jun. 1999;29(6):536-45.
Sayegh et al., The role of T-cell costimulatory activation pathways in transplant rejection. N Engl J Med. Jun. 18, 1998;338(25):1813-21.
Schatton et al., ABCB5 Identifies Immunoregulatory Dermal Cells. Cell Rep. Sep. 8, 2015;12(10):1564-74. doi: 10.1016/j.celrep.2015.08.010.
Schatton et al., Identification of cells initiating human melanomas. Nature. Jan. 17, 2008; 451(7176):345-9.
Schatton et al., In vivo immunomodulatory function of abcb5+ dermal mesenchymal stem cells. Transplantation. Jul. 15, 2006; 82(1): 185-86. Abstract #351.
Schatton et al., Modulation of T-cell activation by malignant melanoma initiating cells. Cancer Res. Jan. 15, 2010;70(2):697-708. Epub Jan. 12, 2010.
Schatton et al., The Chemoresistance Mediator ABCB5 Identifies Melanoma Stem Cells. 14th SPORE Investigator's Workshop. 2006:92. Abstract 150.
Setia et al., Profiling of ABC transporters ABCB5, ABCF2 and nestin-positive stem cells in nevi, in situ and invasive melanoma. Mod Pathol. Aug. 2012;25(8):1169-75. doi: 10.1038/modpathol.2012.71. Epub May 4, 2012.
Sharma et al., Immuno-expression of human melanoma stem cell markers in tissues at different stages of the disease. J Surg Res. Sep. 2010;163(1):e11-5. doi: 10.1016/j.jss.2010.03.043. Epub Apr. 14, 2010.
Shi et al., Transplantation of dermal multipotent cells promotes the hematopoietic recovery in sublethally irradiated rats. J Radiat Res (Tokyo). Mar. 2004;45(1):19-24.
Skolnick et al., From genes to protein structure and function: novel applications of computational approaches in the genomic era. Trends Biotechnol. Jan. 2000;18(1):34-9.
Spangrude et al., Two mechanisms of discrimination between stem cells and progenitors by rhodamine-123: Mitochondrial activation and multi-drug resistance. Blood. 1995;86(1)(Supp 1):461A. Abstract #1830.
Taipalensuu et al., Correlation of gene expression of ten drug efflux proteins of the ATP-binding cassette transporter family in normal human jejunum and in human intestinal epithelial Caco-2 cell monolayers. J Pharmacol Exp Ther. Oct. 2001;299(1):164-70.
Tolcher et al., A randomized phase II and pharmacokinetic study of the antisense oligonucleotides ISIS 3521 and ISIS 5132 in patients with hormone-refractory prostate cancer. Clin Cancer Res. Aug. 2002;8(8):2530-5.
Tsushima et al., Predominant expression of B7-H1 and its immunoregulatory roles in oral squamous cell carcinoma. Oral Oncol. Mar. 2006;42(3):268-74. Epub Nov. 3, 2005.
Young et al., Adult-derived stem cells and their potential for use in tissue repair and molecular medicine. J Cell Mol Med. Jul.-Sep. 2005;9(3):753-69.
Young et al., Human pluripotent and progenitor cells display cell surface cluster differentiation markers CD10, CD13, CD56, and MHC class-I. Proc Soc Exp Biol Med. May 1999;221(1):63-71.
Partial European Search Report for Application No. EP 20156762.5 dated Sep. 24, 2020.
Extended European Search Report dated Jan. 13, 2021 for Application No. EP 20156762.5.
Adamowicz et al., Frequent amplifications and abundant expression of TRIO, NKD2, and IRX2 in soft tissue sarcomas. Genes Chromosomes Cancer. Sep. 2006;45(9):829-38.
Aggarwal et al., Human mesenchymal stem cells modulate allogeneic immune cell responses. Blood. Feb. 15, 2005;105(4):1815-22. doi: 10.1182/blood-2004-04-1559.
Pittenger et al., Multilineage potential of adult human mesenchymal stem cells. Science. Apr. 2, 1999;284(5411):143-7.
Zheng et al., TRIO amplification and abundant mRNA expression is associated with invasive tumor growth and rapid tumor cell proliferation in urinary bladder cancer. Am J Pathol. Jul. 2004;165(1):63-9.
Extended European Search Report for Application No. EP 21187993.7 dated Mar. 7, 2022.
Baer et al., Phase 3 study of the multidrug resistance modulator PSC-833 in previously untreated patients 60 years of age and older with acute myeloid leukemia: Cancer and Leukemia Group B Study 9720. Blood. Aug. 15, 2002;100(4):1224-32.

\* cited by examiner

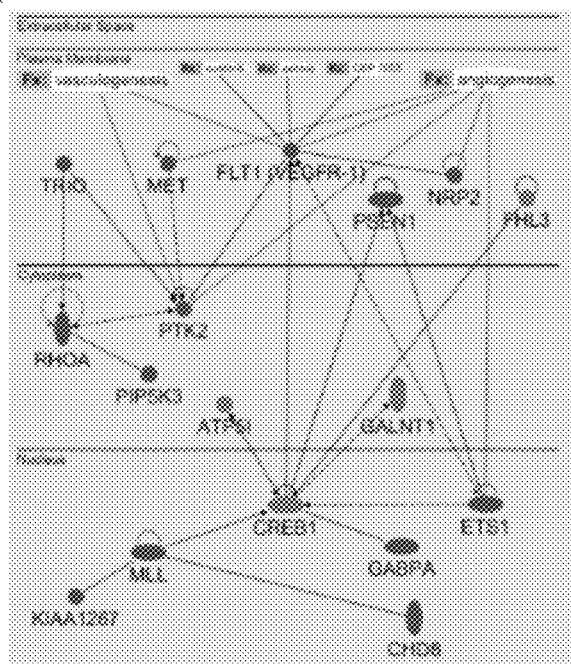
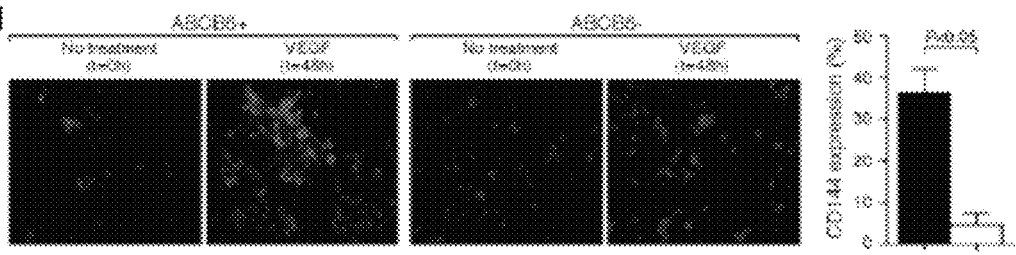
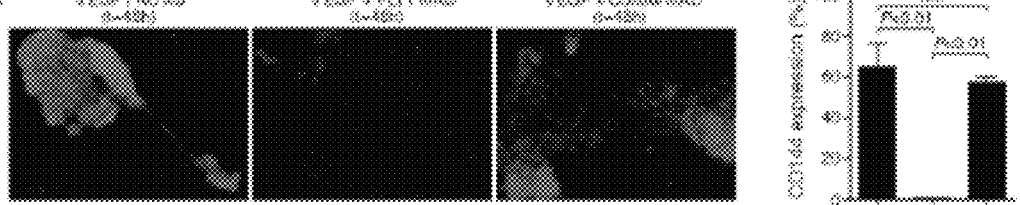
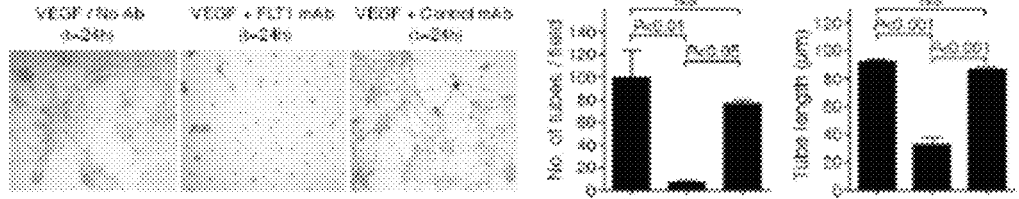
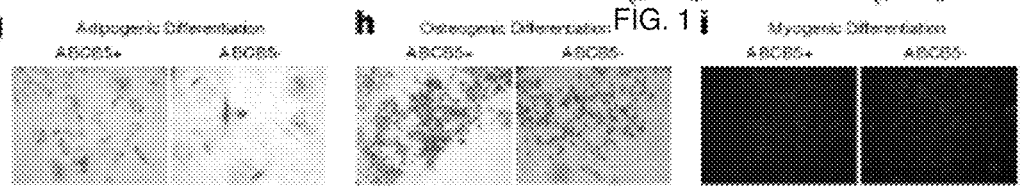

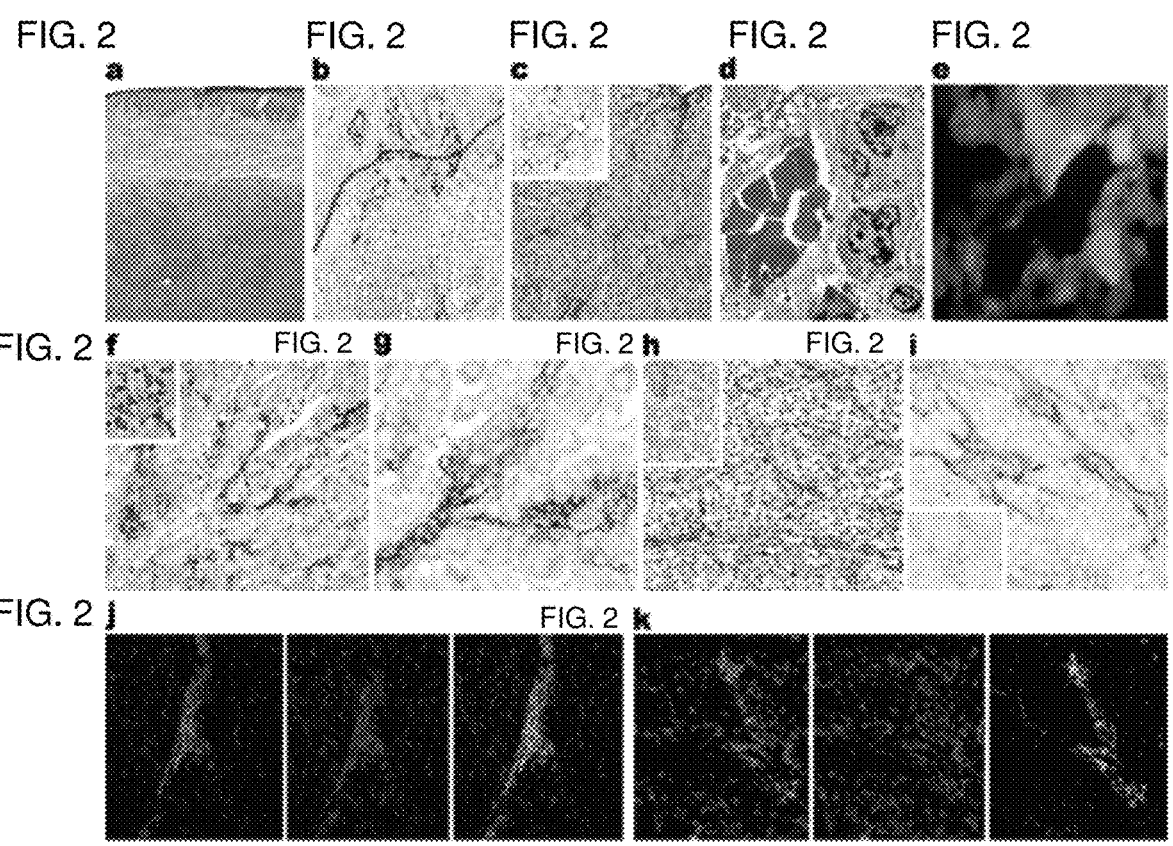

FIG. 3a
 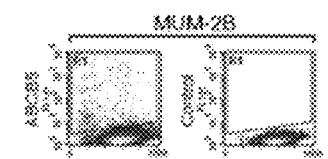 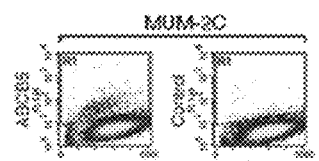
FIG. 3b
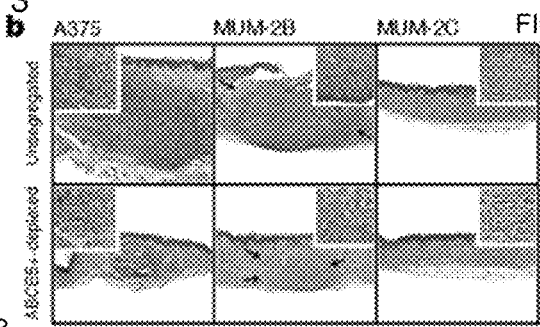
FIG. 3c
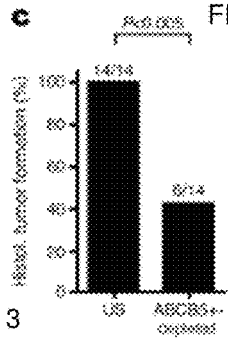
FIG. 3d
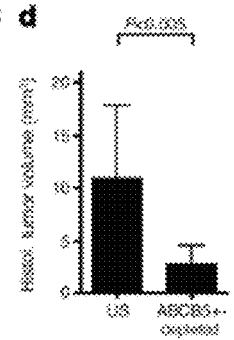
FIG. 3e
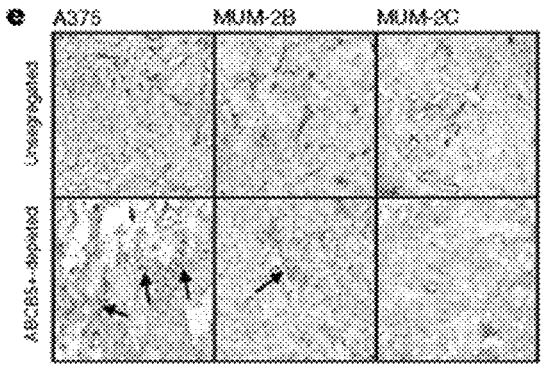
FIG. 3f
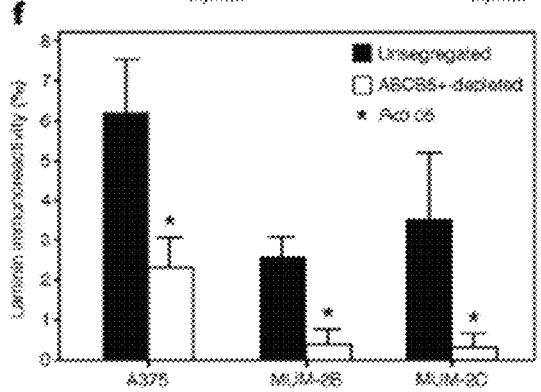

_US 11,542,328 B2_

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 1
tgccttttac tttcgtgtgg                                                   20

<210> SEQ ID NO 2
<211> LENGTH: 21
<212> TYPE: DNA
<213> ORGANISM: Artificial Sequence
<220> FEATURE:
<223> OTHER INFORMATION: Synthetic Olignucleotide

<400> SEQUENCE: 2
ccaaattcct gttttgcttc a                                                 21

<210> SEQ ID NO 3
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 3
ccccacctta tcctgacgta                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 4
cgtgtgtcca cctcatcatc                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 5
gaggcagggg aaaatagagg                                                   20

<210> SEQ ID NO 6
```

```
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 6
tctcccgaaa ggttgaaatg                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 7
cgcttactct gttgggtct                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 8
tctccagcaa aatgatgtgc                                                   20

<210> SEQ ID NO 9
<211> LENGTH: 22
<212> TYPE: DNA
<213> ORGANISM: Artificial Sequence
<220> FEATURE:
<223> OTHER INFORMATION: Synthetic Olignucleotide

<400> SEQUENCE: 9
tggcaactgc ttttatgttc tg                                                22

<210> SEQ ID NO 10
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 10
tccatagggt gatggtcaaa                                                   20

<210> SEQ ID NO 11
<211> LENGTH: 21
<212> TYPE: DNA
<213> ORGANISM: Artificial Sequence
<220> FEATURE:
<223> OTHER INFORMATION: Synthetic Olignucleotide

<400> SEQUENCE: 11
gctgaggaat ccacccaatc t                                                 21

<210> SEQ ID NO 12
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 12
```
agcctgaatg gccttttgtg                                           20

<210> SEQ ID NO 13
<211> LENGTH: 18
<212> TYPE: DNA
<213> ORGANISM: Artificial Sequence
<220> FEATURE:
<223> OTHER INFORMATION: Synthetic Olignucleotide

<400> SEQUENCE: 13
cctggcaccc agcacaat                                             18

<210> SEQ ID NO 14
<211> LENGTH: 20
<212> TYPE: DNA
<213> ORGANISM: Artificial Sequence
<220> FEATURE:
<223> OTHER INFORMATION: Synthetic Olignucleotide

<400> SEQUENCE: 14
agtactccgt gtggatcggc                                           20

<210> SEQ ID NO 15
<211> LENGTH: 45
<212> TYPE: DNA
<213> ORGANISM: Artificial Sequence
<220> FEATURE:
<223> OTHER INFORMATION: Synthetic Olignucleotide

<400> SEQUENCE: 15
taatacgact cactataggg atgtctggct ttttcccttc ttgac               45

<210> SEQ ID NO 16
<211> LENGTH: 45
<212> TYPE: DNA
<213> ORGANISM: Artificial Sequence
<220> FEATURE:
<223> OTHER INFORMATION: Synthetic Olignucleotide

<400> SEQUENCE: 16
gatttaggtg acactataga aattcaagct ggacgaatga cccca               45

<210> SEQ ID NO 17
<211> LENGTH: 42
<212> TYPE: DNA
<213> ORGANISM: Artificial Sequence
<220> FEATURE:
<223> OTHER INFORMATION: Synthetic Olignucleotide

<400> SEQUENCE: 17
taatacgact cactataggg agcagcccca ggacacagca ta                  42

<210> SEQ ID NO 18
<211> LENGTH: 41
<212> TYPE: DNA
<213> ORGANISM: Artificial Sequence
<220> FEATURE:
<223> OTHER INFORMATION: Synthetic Olignucleotide

<400> SEQUENCE: 18
gatttaggtg acactataga gacccaagac tcccataaag c                   41

THERAPEUTIC AND DIAGNOSTIC METHODS RELATING TO CANCER STEM CELLS

RELATED APPLICATION

This application is a Continuation of U.S. application Ser. No. 14/868,126, filed Sep. 28, 2015, which is a Continuation of U.S. application Ser. No. 13/128,915, filed Aug. 9, 2011, which is a national stage filing under 35 U.S.C. 371 of International Patent Application Serial No. PCT/US2009/006089, filed Nov. 13, 2009, which claims priority under 35 U.S.C. § 119 from U.S. provisional application Ser. No. 61/114,490, filed Nov. 14, 2008, the contents of which are incorporated herein in their entirety.

FEDERALLY SPONSORED RESEARCH

This invention was made with Government support under Grant 5R01CA113796-03 from the National Cancer Institute. The Government has certain rights to this invention.

FIELD OF INVENTION

The present invention relates in part to methods for treating individuals having cancer. The methods involve modulating, e.g., inducing or inhibiting, the activity of genes that are deregulated in cancer stem cells. In some aspects, cell surface genes that are upregulated in cancer stem cells are targeted for selective isolation, detection, or killing of cancer stem cells in melanoma. Other aspects of the invention relate to reagents, arrays, compositions, and kits that are useful for diagnosing and treating cancer.

BACKGROUND OF INVENTION

Self-renewing cancer stem cells (CSCs) initiate tumours and drive malignant progression by generating and supporting replication of more differentiated non-stem cell progeny. (M. Al-Hajj, et al., Proc Natl Acad Sci USA 100 (7), 3983 (2003); D. Bonnet and J. E. Dick, Nat Med 3 (7), 730 (1997); C. A. O'Brien, et al., Nature 445 (7123), 106 (2007); L. Ricci-Vitiani, et al., Nature 445 (7123), 111 (2007); S. K. Singh, et al., Nature 432 (7015), 396 (2004); T. Schatton and M. H. Frank, Pigment cell & melanoma research 21 (1), 39 (2008)). The mechanisms by which CSCs cause tumour formation and growth and the potential role of CSC-specific differentiation plasticity in tumourigenicity are currently unknown. We recently identified a subpopulation of CSC based on expression of the chemoresistance mediator ABCB5 (ATP-binding cassette, sub-family B (MDR/TAP), member 5) (N. Y. Frank, A et al., Cancer Res 65 (10), 4320 (2005); Y. Huang, et al., Cancer Res 64 (12), 4294 (2004)) within human malignant melanoma (T. Schatton, et al., Nature 451 (7176), 345 (2008)), a highly aggressive and drug-resistant cancer. (T. Schatton and M. H. Frank, Pigment cell & melanoma research 21 (1), 39 (2008); L. Chin, L. A. Garraway, and D. E. Fisher, Genes Dev 20 (16), 2149 (2006).) ABCB5$^+$ Malignant Melanoma Initiating Cells (MMIC) correlate with clinical disease progression and can be specifically targeted to abrogate tumour growth. (T. Schatton, et al., Nature 451 (7176), 345 (2008)). Consistent with these findings, the ABCB5 gene is also preferentially expressed by in vitro self-renewing melanoma minority populations (G. I. Keshet, et al., Biochem Biophys Res Commun 368 (4), 930 (2008)) and by melanoma cell lines of metastatic as opposed to primary, radial growth phase tumour origin (J. F. Sousa and E. M. Espreafico, BMC cancer 8, 19 (2008)).

SUMMARY OF INVENTION

The present invention relates in part to the discovery that a number of genes (referred to herein as CSC-associated genes) are deregulated in cancer stem cells. In some aspects, the invention relates to diagnostic arrays and methods for detecting cancer in an individual based on the expression of CSC-associated genes. In other aspects, the invention relates to methods useful for treating individuals having melanoma based on modulating the expression and/or activity of CSC-associated genes. Compositions and kits that are useful for the foregoing methods are also disclosed.

The invention, in some aspects, provides methods for diagnosing cancer in an individual. In some aspects, the methods involve determining an expression level of a cancer stem cell (CSC)-associated gene in Table 5 in a test sample from the individual and comparing the expression level of the CSC-associated gene to a reference value, wherein results of the comparison are diagnostic of cancer. In some embodiments, the cancer is melanoma, breast cancer, prostate cancer, colon cancer or renal cancer. In some embodiments, the test sample is a tissue biopsy. In some embodiments, the test sample is a skin biopsy. In some embodiments, the test sample is a sample of the cancer, such as a tumor biopsy. In some embodiments, the methods involve updating a patient record for the individual to indicate the diagnostic result of the comparison. In some embodiments, determining comprises detecting in the test sample a mRNA that is encoded by the CSC-associated gene. In some embodiments, determining comprises detecting in the test sample a polypeptide that is encoded by the CSC-associated gene. In certain embodiments, detecting comprises nucleic acid hybridization or nucleic acid amplification. In specific embodiments, the nucleic acid amplification is real-time RT-PCR or RT-PCR. In one embodiment, the nucleic acid hybridization is performed using a nucleic acid array. In certain other embodiments, detecting comprises immunodetection of the polypeptide. In one embodiment, the immunodetection comprises an Enzyme-Linked Immunosorbent Assay (ELISA). In one embodiment, the immunodetection comprises an antibody array. In one embodiment, the immunodetection comprises immunohistochemistry.

In some embodiments of the methods, the reference value is the expression level of the CSC-associated gene in a non-cancer reference sample, and if the expression level of the CSC-associated gene in the test sample is about equal to the expression level of the CSC-associated gene in the non-cancer reference sample, then the comparison does not indicate cancer.

In some embodiments of the methods, the reference value is the expression level of the CSC-associated gene in a cancer reference sample, and if the expression level of the CSC-associated gene is about equal to the expression level of the CSC-associated gene in the cancer reference sample, then the comparison indicates cancer.

In some embodiments of the methods, the CSC-associated gene is in Table 1 or 8 and the reference value is the expression level of the CSC-associated gene in a non-cancer reference sample, and if the expression level of the CSC-associated gene in the test sample is significantly higher than the expression level of the CSC-associated gene in the non-cancer reference sample, the comparison indicates cancer.

In some embodiments of the methods, the CSC-associated gene is in Table 1 or 8 and the reference value is the expression level of the CSC-associated gene in a cancer reference sample, and if the expression level of the CSC-associated gene in the test sample is significantly lower than the expression level of the CSC-associated gene in the cancer reference sample, the comparison does not indicate cancer.

In some embodiments of the methods, the CSC-associated gene is in Table 1 or 8 and the reference value is the expression level of the CSC-associated gene in a non-cancer reference sample, and if the expression level of the CSC-associated gene in the test sample is at least 10% higher than the expression level of the CSC-associated gene in the non-cancer reference sample, the comparison indicates cancer.

In some embodiments of the methods, the CSC-associated gene is in Table 2 or 7 and the reference value is the expression level of the CSC-associated gene in a non-cancer reference sample, and if the expression level of the CSC-associated gene in the test sample is significantly lower than the expression level of the CSC-associated gene in the non-cancer reference sample, the comparison indicates cancer.

In some embodiments of the methods, the CSC-associated gene is in Table 2 or 7 and the reference value is the expression level of the CSC-associated gene in a cancer reference sample, and if the expression level of the CSC-associated gene in the test sample is significantly higher than the expression level of the CSC-associated gene in the cancer reference sample, the comparison does not indicate cancer.

In some embodiments of the methods, the CSC-associated gene is in Table 2 or 7 and the reference value is the expression level of the CSC-associated gene in a non-cancer reference sample, and if the expression level of the CSC-associated gene in the test sample is at least 10% lower than the expression level of the CSC-associated gene in the non-cancer reference sample, the comparison indicates cancer.

The invention, in some aspects, provides methods for isolating a cancer stem cell. In some aspects, the methods involve contacting a sample with an agent that binds a polypeptide, which is encoded by a CSC-associated gene in Table 4 and expressed on the surface of the cancer stem cell, and isolating the agent from the sample. If the sample contains the cancer stem cell, the agent binds to the polypeptide on the surface of the cancer stem cell such that isolation of the agent from the sample results in isolation of the cancer stem cell. In some embodiments, the CSC-associated gene is selected from the group consisting of: ANK2, NCKAP1L, PTPRE, PTPRS, SBF1, SCN3A, SGCA, SGCB, SLC2A11, SLC2A8, SLC4A1, STX3, and TBC1D8. In some embodiments, the agent is an isolated peptide that specifically binds the polypeptide on the surface of the cancer stem cell. In certain embodiments, the isolated peptide is an antibody or antigen-binding fragment. In specific embodiments, the antibody or antigen-binding fragment is a monoclonal antibody, polyclonal antibody, human antibody, chimeric antibody, humanized antibody, single-chain antibody, F(ab')$_2$, Fab, Fd, Fv, or single-chain Fv fragment. In some embodiments, the isolated peptide is bound to a solid support. In some embodiments, the isolated peptide is conjugated to a detectable label. In some embodiments, the detectable label is a fluorophore which may be selected from: FITC, TRITC, Cy3, Cy5, Alexa Fluorescent Dyes, and Quantum Dots. In some embodiments, the isolating comprises performing fluorescent activated cell sorting to isolate a cancer stem cell bound to a detectable label. In some embodiments, the cancer stem cell is from a melanoma, breast cancer, prostate cancer, colon cancer or renal cancer.

The invention, in some aspects, provides methods for treating an individual having, or at risk of having, cancer. In some aspects, the methods involve administering a therapeutically effective amount of a composition that induces the expression of a CSC-associated gene selected from the group set forth in Table 2 or 7. In some embodiments, the cancer is melanoma, breast cancer, prostate cancer, colon cancer or renal cancer.

In some embodiments, the composition that induces the expression of a CSC-associated gene comprises an isolated plasmid that expresses the CSC-associated gene. In some embodiments, the isolated plasmid is in a virus capable of infecting the individual. In certain embodiments, the virus is selected from adenovirus, retrovirus, lentivirus, and adeno-associated virus. In some embodiments, the isolated plasmid comprises a cancer specific promoter operably linked to the CSC-associated gene.

The invention, in other aspects, provides methods for treating an individual having, or at risk of having, cancer that involve administering a therapeutically effective amount of a composition that targets a product of a CSC-associated gene selected from the group set forth in Table 1 or 8. In some embodiments, the cancer is melanoma, breast cancer, prostate cancer, colon cancer or renal cancer. In some embodiments, the CSC-associated gene is selected from the group set forth in Table 4. In certain embodiments, the CSC-associated gene is selected from the group consisting of: ANK2, NCKAP1L, PTPRE, PTPRS, SBF1, SCN3A, SGCA, SGCB, SLC2A11, SLC2A8, SLC4A1, STX3, and TBC1D8.

In some embodiments, the composition that targets a product of a CSC-associated gene comprises a small interfering nucleic acid that inhibits expression of the CSC-associated gene. In some embodiments, the composition comprises an isolated plasmid that expresses the small interfering nucleic acid. In certain embodiments, the plasmid is in a virus. In specific embodiments, the virus is selected from adenovirus, retrovirus, lentivirus, and adeno-associated virus. In certain embodiments, the isolated plasmid comprises a cancer-specific promoter operably linked to a gene encoding the small interfering nucleic acid.

In some embodiments, the composition that targets a product (e.g., protein or RNA) of a CSC-associated gene comprises an isolated molecule that selectively binds to a polypeptide encoded by the CSC-associated gene. In certain embodiments, the isolated molecule is conjugated to a therapeutic agent. In specific embodiments, the isolated molecule is an antibody or antigen-binding fragment. In particular embodiments, the antibody or antigen-binding fragment is a monoclonal antibody, polyclonal antibody, human antibody, chimeric antibody, humanized antibody, a single-chain antibody, F(ab')$_2$, Fab, Fd, Fv, or single-chain Fv fragment. In specific embodiments, the therapeutic agent is selected from: a toxin, a small-interfering nucleic acid, and a chemotherapeutic agent. In one embodiment, the toxin is a radioisotope. In particular embodiments, the radioisotope is selected from the group consisting of: $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Bo, $^{64}$Cu, $^{212}$Pb, $^{224}$Ra and $^{223}$Ra. In some embodiments, the therapeutic agent is a small interfering nucleic acid that inhibits expression of a CSC-associated gene. In some embodiments, the isolated molecule binds to the polypeptide and enters an intracellular compartment of a cancer stem cell of the cancer.

In some embodiments, the treatment methods involve determining the expression level of the CSC-associated gene in the individual. In certain embodiments, the methods involve comparing the expression level of the CSC-associated gene to a reference value, wherein results of the comparison are diagnostic of cancer in the individual. In specific embodiments, if the comparison results in a diagnosis of cancer in the individual, the administering is performed. In one embodiment, the determining and the comparing are repeated at one or more intervals after the administering. In some embodiments, the administering is orally, intravenously, intrapleurally, intranasally, intramuscularly, subcutaneously, intraperitoneally, or as an aerosol.

The invention, in some aspects, provides methods of delivering a therapeutic agent to a cancer stem cell that involve contacting a cancer stem cell with an isolated molecule, which selectively binds to a polypeptide encoded by a CSC-associated gene selected from the group set forth in Table 4 and which is conjugated to a therapeutic agent, in an effective amount to deliver the therapeutic agent to the cancer stem cell. In some embodiments, the CSC-associated gene is selected from the group consisting of: ANK2, NCKAP1L, PTPRE, PTPRS, SBF1, SCN3A, SGCA, SGCB, SLC2A11, SLC2A8, SLC4A1, STX3, and TBC1D8. In some embodiments, the isolated molecule is an antibody or antigen-binding fragment that selectively binds the polypeptide. In some embodiments, the therapeutic agent is selected from: a toxin, a small-interfering nucleic acid, and a chemotherapeutic agent. In one embodiment, the toxin is a radioisotope. In particular embodiments, the radioisotope is selected from the group consisting of: $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Bo, $^{64}$Cu, $^{212}$Pb, $^{224}$Ra and $^{223}$Ra. In some embodiments, the therapeutic agent is a small interfering nucleic acid that inhibits expression of a CSC-associated gene. In some embodiments, the cancer stem cell is in vitro. In other embodiments, the cancer stem cell is in vivo.

In some aspects, the invention provides nucleic acid arrays consisting essentially of at least 2, at least 5, at least 10, at least 20, at least 50, at least 100, at least 200, at least 300, or more CSC-associated genes set forth in Table 5.

In some aspects, the invention provides polypeptide arrays consisting essentially of at least 2, at least 5, at least 10, at least 20, at least 50, at least 100, or more polypeptides or immunogenic fragments thereof encoded by CSC-associated genes set forth in Table 1 or 8. In some aspects, the invention provides antibody arrays consisting essentially of at least 2 or more different antibodies or antigen-binding fragments that selectively bind polypeptides encoded by CSC-associated genes set forth in Table 1 or 8.

In some aspects, the invention provides methods for stratifying a population comprising individuals having cancer. The methods involve determining expression levels of at least 2, at least 5, at least 10, at least 20, at least 50, at least 100, at least 200, at least 300, or more CSC-associated genes set forth in Table 5 and stratifying the population based on the expression levels.

In some aspects, the invention provides an isolated molecule that selectively binds to a polypeptide encoded by a CSC-associated gene set forth in Table 4, and that is conjugated to a therapeutic agent. In some embodiments, the CSC-associated gene is selected from the group consisting of: ANK2, NCKAP1L, PTPRE, PTPRS, SBF1, SCN3A, SGCA, SGCB, SLC2A11, SLC2A8, SLC4A1, STX3, and TBC1D8. In some embodiments, the therapeutic agent is selected from: a toxin, a small-interfering nucleic acid, and a chemotherapeutic agent.

In certain embodiments, the isolated molecule is an antibody or antigen-binding fragment. In certain embodiments, the antibody or antigen-binding fragment is a monoclonal antibody, polyclonal antibody, human antibody, chimeric antibody, humanized antibody, single-chain antibody, a F(ab')$_2$, Fab, Fd, or Fv fragment. In certain embodiments, the isolated molecule is an isolated receptor ligand of the polypeptide.

The invention, in some aspects, provides compositions comprising any of the foregoing isolated molecules. In some embodiments, the compositions include a pharmaceutically acceptable carrier.

The invention, in some aspects, provides pharmaceutical kits that include a container housing any of the foregoing compositions and instructions for administering the composition to an individual having cancer.

Use of a composition of the invention for treating cancer is also provided as an aspect of the invention.

A method for manufacturing a medicament of a composition of the invention for treating cancer is also provided.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

BRIEF DESCRIPTION OF DRAWINGS

FIGS. 1A-1I depict an analysis of vasculogenic/angiogenic pathways in human melanoma. FIG. 1a. is a graphical representation of pathway activation across ABCB5$^+$ MMIC. Genes represented by nodes (dark gray circles, TRIO, MET, FLT1, PSEN1, NRP2, RHOA, PTK2, PIP5K3, KIAA1267, MLL, GABPA, ETS1, and CHD8) are overexpressed in ABCB5$^+$ relative to ABCB5$^-$ human melanoma cells and those represented by black nodes are expressed at lower levels, respectively. Black lines between genes show known interactions. Known gene functions in vasculogenesis and angiogenesis, and genes known as relevant drug targets are annotated (dark gray lines). Gene relationships and figure layout are based on Ingenuity Pathway Analysis and references are provided elsewhere in the text. FIG. 1b. shows detection of vasculogenic/angiogenic pathway members by RT-PCR in ABCB5$^+$ MMIC. FIG. 1c. shows FLT1 (VEGFR-1) protein expression on ABCB5$^+$ MMIC (top) and ABCB5$^-$ melanoma cells (bottom) as determined by dual color flow cytometry using ABCB5 phenotype-specific cell gating, with mean percentages (mean±s.e.m., n=6 replicate experiments) shown on the right. FIG. 1d. depicts representative immunofluorescence staining for CD144 expression (Texas red staining) by ABCB5$^+$ MMIC or ABCB5⁻ melanoma cell subpopulations prior to (t=0 h) and upon 48 h of culture (t=48 h) in the presence of 100 ng/ml VEGF[11], with nuclei counterstained with DAPI. Mean percentages (mean±s.e.m., n=3 replicate experiments) of cells staining positively for CD144 in each sample are shown on the right. FIG. 1e. shows representative immunofluorescence staining for CD144 expression (Texas red staining) by melanoma cells cultured for 48 h (t=48 h) in the presence of 100 ng/ml VEGF as in above, but in the presence or absence of anti-FLT1 (VEGFR-1) blocking mAb or isotype control mAb. Nuclei are counterstained with DAPI. Mean percentages (mean±s.e.m., n=3 replicate experiments) of cells staining positively for CD144 in each sample are shown in the far right panel. FIG. 1f. shows tube formation detected by phase contrast light microscopy of melanoma cells cultured for 24 h (t=24 h) in the presence of 100 ng/ml VEGF and the presence or absence of anti-FLT1 (VEGFR-1) blocking mAb or isotype control mAb. Number of tubes/microscopy field (mean±s.e.m., n=3 replicate experiments) and tube length (μm) (mean±s.e.m., n=3 replicate experiments) are illustrated for the different experimental conditions on the far right panels, respectively. FIG. 1g. shows the adipogenic differentiation potential of ABCB5⁺ and ABCB5⁻ human melanoma cells (Oil Red O staining, nuclei are counterstained with hematoxylin). FIG. 1h. shows the osteogenic differentiation potential of ABCB5⁺ and ABCB5⁻ human melanoma cells (Alizarin Red staining). FIG. 1i shows the myogenic differentiation potential of ABCB5⁺ and ABCB5⁻ human melanoma cells. Absence of myogenin staining (FITC, green) is detected in ABCB5⁺ or ABCB5⁻ human melanoma cells (nuclei are counterstained with DAPI).

FIGS. 2A-2K depict an analysis of MMIC-driven in vivo vasculogenesis. FIG. 2a. shows conventionally-stained (H&E) sections of human melanoma growing at melanoma cell injection site within human dermis of skin xenograft to NOD/SCID mouse. FIG. 2b. shows immunohistochemistry for human CD31 indicating angiogenic response at perimeter of melanoma within human xenograft; broken line represents interface of tumour nodule with dermal connective tissue. FIG. 2c. shows PAS (with diastase) immunochemical staining of CD31-negative interior regions of melanoma xenograft revealing numerous anastomosing channels (inset is laminin immunohistochemistry indicating identical pattern). FIG. 2d. shows transmission electron micrographs of interior regions of melanoma xenograft; lumenal spaces containing blood products (erythrocytes) are lined by melanoma cells and associated basement membrane-like extracellular matrix. FIG. 2e. shows the interior zone of melanoma xenograft derived from cells expressing GFP transgene and immunohistochemically stained for endothelial marker CD144 (FAST RED Chromogen (SIGNET) from Covance Research Products, Inc); CD144 expression is confined to cells forming lumen-like spaces lined by cells that co-express GFP and CD144 (indicated by dual staining). FIGS. 2f and g. show low (f) and high (g) magnifications of immunohistochemistry for ABCB5 protein; reactivity is restricted to anastomosing channels identical to those seen in panel c. The inset in panel f depicts similar formation of ABCB5-reactive channels in a patient-derived melanoma biopsy. FIG. 2h. depicts in situ hybridization for ABCB5 mRNA revealing a channel pattern corresponding to that of ABCB5 protein expression (compare with panel f; inset is sense control). FIG. 2i. shows the detection of anti-ABCB5 mAb using anti-mouse Ig immunohistochemistry in melanoma xenografts after intravenous administration in vivo; note localization to channels (inset represents anti-mouse Ig staining after intravenous administration of irrelevant isotype-matched control mAb). FIG. 2j. shows dual-labeling immunofluorescence microscopy for ABCB5 (left panel), CD144 (middle panel), and ABCB5 & CD144 (right panel). FIG. 2k shows dual-labeling immunofluorescence microscopy for ABCB5 (left panel), TIE-1 (middle panel), and ABCB5 & TIE-1 (right panel).

FIGS. 3A-3F depict the interdependency of MMIC-driven vasculogenesis and tumourigenesis. FIG. 3a. shows representative flow cytometric ABCB5 expression or control staining (FITC, F11) plotted against forward scatter (FSC) for human A375, MUM-2B, and MUM-2C melanoma cell inocula. FIG. 3b. shows representative histologic sections of melanomas that developed from three unsegregated and ABCB5-depleted melanoma cell lines injected intradermally into human skin xenografts. FIG. 3c. shows histologically determined tumour formation rate (%) 3 weeks following intradermal transplantation of unsegregated vs. ABCB5⁺-depleted human A375, MUM-2B or MUM-2C melanoma cells (2×10⁶/inoculum) into human skin/Rag2⁻/⁻ chimeric mice (n=5, respectively). FIG. 2d. shows histological tumour volumes (mean±s.e.m.) 3 weeks following intradermal transplantation of unsegregated vs. ABCB5⁺-depleted human A375, MUM-2B or MUM-2C melanoma cells (2×10⁶/inoculum) into human skin/Rag2⁻/⁻ chimeric mice. FIG. 3e shows immunohistochemistry for laminin revealing extent of channel formation in melanomas that developed from unsegregated or ABCB5⁺-depleted melanoma cell inocula derived from A375, MUM-2B or MUM-2C lines injected intradermally into human skin xenografts (arrows=necrosis). FIG. 3f depicts image analysis of laminin immunoreactivity for melanomas derived from unsegregated and ABCB5⁺-depleted cell inocula; y-axis is percent of pixelated area with reactivity (mean±s.e.m.); solid bar represents tumours derived from unsegregated melanoma cells, open bars represent tumours derived from ABCB5⁺-depleted cells (A375, P<0.0032; MUM-2B, P<0.0005; MUM-2C, P<0.0059).

FIG. 4a. shows western blots of ABCB5 and tubulin expression of a panel of human melanoma cell lines. FIG. 4b shows relative ABCB5 mRNA expression (log 2) in a panel of human melanoma cell lines plotted against ABCB5 protein expression as determined by ratios of ABCB5 89 kD western blot band intensity and tubulin western blot band intensity for each human melanoma cell line. Data points in FIG. 4b are: 1, SK-MEL-2; 2, SK-MEL-5; 3, SK-MEL-28; 4, MDA-MB-435; 5, UACC-62; 6, UACC-257; 7, M14; 8, MALME-3M. r, Spearman Rank Correlation r (corrected for ties).

DETAILED DESCRIPTION

Figure 4:
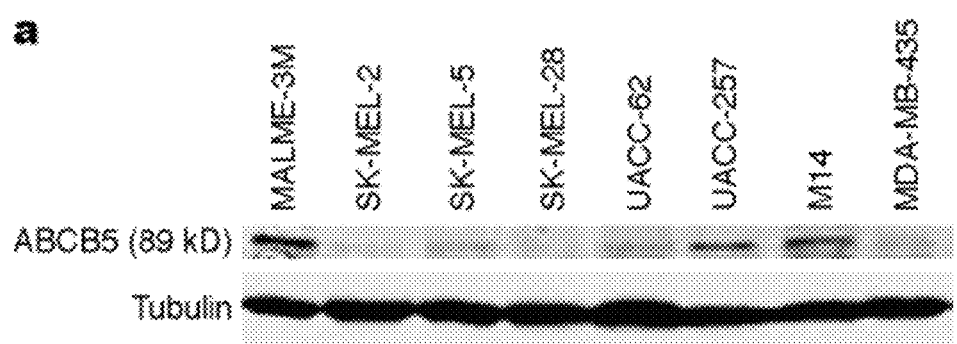
FIGS. 4A and 4B depict an analysis of the correlation of ABCB5 protein and mRNA expression across human melanoma cell lines.
Figure 4:
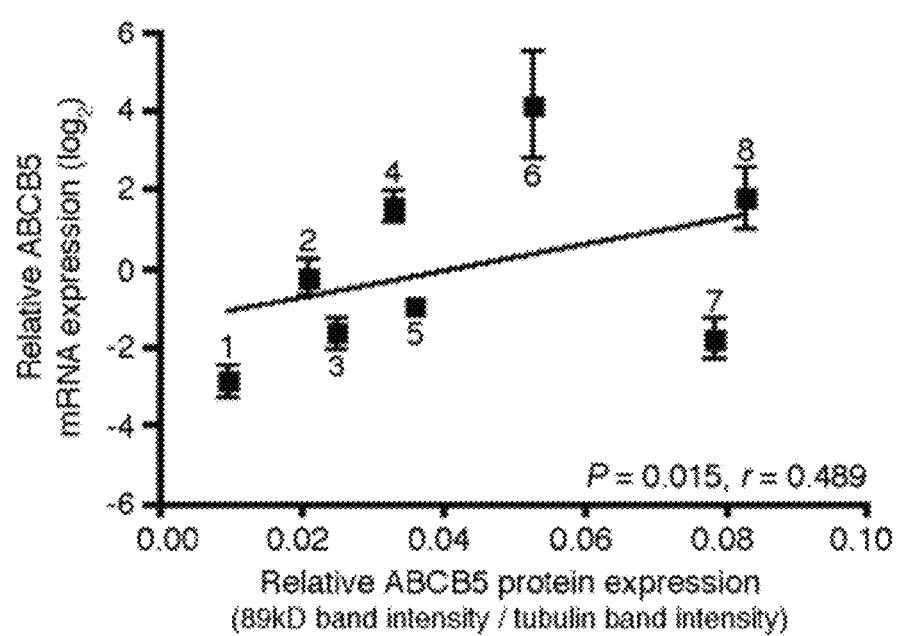

The present invention relates in part to the discovery that numerous CSC-associated genes have altered expression or function in cancer stem cells, e.g., melanoma stem cells. In some aspects, the invention relates to diagnostic arrays and methods for detecting cancer, e.g., melanoma, in an individual based on the expression of CSC-associated genes. In other aspects, the invention relates to compositions, kits, and methods useful for treating individuals having cancer. In some embodiments, the treatment methods involve modulating e.g., inducing or inhibiting, the activity of CSC-associated genes. The CSC-associated genes can be modulated by any one of a number of ways known in the art and described herein e.g., overexpression, RNAi-based inhibition, etc. In some cases, the CSC-associated genes encode cell surface proteins which, when upregulated in cancer stem cells, may be selectively targeted for isolating, e.g., by flow cytometry, identifying, e.g., by immunolabeling, and killing of cancer stem cells, e.g., melanoma stem cells.

The mechanism by which CSCs cause tumor formation and growth and the potential role of CSC-specific differentiation plasticity in tumorigenicity are currently unknown. It has been demonstrated according to the invention that CSC play an important role in providing nutritional support to growing tumors. For instance we have shown herein (Examples) a selective capacity of ABCB5+ malignant melanoma initiating cells (MMIC)[3] to undergo vasculogenic differentiation and to generate blood-perfused vessel-like channels in vivo. A repertoire of genes differentially expressed in MMIC compared to tumour bulk populations were identified by microarray analyses on purified ABCB5+ and ABCB5− cell subsets derived from the established human melanoma cell lines and from three separate patient-derived melanoma specimens. Using this approach, 399 genes were identified that were differentially expressed between ABCB5+ MMIC and ABCB5− melanoma bulk populations. The genes, which are outlined in Tables 1-8, are referred to herein as CSC-associated genes. Of the CSC-associated genes, 265 were upregulated (Table 1; Table 1 includes Table 1.1 and Table 1.2) and 150 were downregulated (Table 2). For certain CSC-associated genes, subcellular location, e.g., plasma membrane, nucleus, etc., gene type, e.g., enzyme, complex, transporter, etc., and drugs that affect, e.g., target, their activity are identified (Table 3). A summary of those annotations and networks is provide in Table 3. Genes that function share a common pathway have a common "network") designation in Table 3. Some CSC-associated genes, e.g., those which have "plasma membrane" annotations, encode proteins that are associated with the cell surface. Such cell surface proteins are useful in a variety ways. For example, cell surface proteins that are upregulated in cancer stem cells, may be selectively targeted, e.g., using the methods disclosed herein, for isolating, identifying, and killing of cancer stem cells. A listing of exemplary cell surface proteins encoded by CSC-associated genes is provided in Table 4.

TABLE 1.1

Upregulated CSC-associated genes (p < 0.05)

| GENESYMBOL | ID | Fold Change |
|---|---|---|
| HECW1 | 237295_at | 11.843 |
| RP11-139H14.4 | 1569124_at | 11.472 |
| CDC16 | 242359_at | 6.261 |
| ANK2 | 202921_s_at | 4.162 |
| LOC146325 | 1553826_a_at | 3.943 |
| UGT1A6 | 206094_x_at | 3.86 |
| C12ORF51 | 1557529_at | 3.632 |
| SNRPA1 | 242146_at | 3.54 |
| PDE4B | 215671_at | 3.457 |
| PAPD4 | 222282_at | 3.39 |
| ZNF536 | 233890_at | 3.303 |
| KSR2 | 230551_at | 3.211 |
| BUB1 | 233445_at | 3.209 |
| ZNF292 | 236435_at | 3.201 |
| CABIN1 | 1557581_x_at | 3.052 |
| SDAD1 | 242190_at | 3.009 |
| ASCC3L1 | 214982_at | 3.009 |
| ZNF224 | 216983_s_at | 2.986 |
| KIDINS220 | 1557246_at | 2.97 |
| WIPF2 | 216006_at | 2.916 |
| C12ORF51 | 230216_at | 2.874 |
| VPS37B | 236889_at | 2.85 |
| NARG1 | 1556381_at | 2.827 |

TABLE 1.1-continued

Upregulated CSC-associated genes (p < 0.05)

| GENESYMBOL | ID | Fold Change |
|---|---|---|
| LOC145757 | 1558649_at | 2.779 |
| SDCCAG8 | 243963_at | 2.67 |
| ZNF154 | 242170_at | 2.667 |
| ZFR | 238970_at | 2.655 |
| TRPV1 | 1556229_at | 2.636 |
| ANAPC5 | 235926_at | 2.631 |
| CUL4A | 232466_at | 2.607 |
| TRIO | 240773_at | 2.607 |
| LOC283888 | 1559443_s_at | 2.56 |
| RAB11FIP3 | 228613_at | 2.546 |
| PTK2 | 234211_at | 2.539 |
| MYO10 | 243159_x_at | 2.528 |
| NAT8B | 206964_at | 2.513 |
| CDC14B | 234605_at | 2.512 |
| TRIM33 | 239716_at | 2.496 |
| SF1 | 210172_at | 2.452 |
| SGCA | 1562729_at | 2.395 |
| LOC285147 | 236166_at | 2.377 |
| N4BP2L2 | 242576_x_at | 2.349 |
| HNRPH1 | 213472_at | 2.332 |
| FLJ10357 | 241627_x_at | 2.31 |
| PHF20L1 | 219606_at | 2.3 |
| ANKRD28 | 241063_at | 2.297 |
| TRNT1 | 243236_at | 2.295 |
| GOLGA8A | 213650_at | 2.289 |
| KIAA1618 | 231956_at | 2.27 |
| RBM5 | 209936_at | 2.249 |
| LOC645513 | 239556_at | 2.24 |
| LOC729397 | 236899_at | 2.231 |
| PABPN1 | 213046_at | 2.228 |
| SVIL | 215279_at | 2.228 |
| PIP5K3 | 1557719_at | 2.227 |
| STRAP | 1558002_at | 2.189 |
| KIAA2013 | 1555933_at | 2.18 |
| NUPL1 | 241425_at | 2.179 |
| IFNGR1 | 242903_at | 2.171 |
| AKAP9 | 215483_at | 2.168 |
| LOC254128 | 1557059_at | 2.164 |
| IRS2 | 236338_at | 2.162 |
| RHOA | 240337_at | 2.143 |
| JARID2 | 232835_at | 2.139 |
| GPD2 | 243598_at | 2.13 |
| RADIL | 223693_s_at | 2.126 |
| CROP | 242389_at | 2.121 |
| EXT1 | 242126_at | 2.116 |
| XRCC5 | 232633_at | 2.106 |
| PDXDC1 | 1560014_s_at | 2.105 |
| MEF2C | 236395_at | 2.104 |
| ZNF567 | 242429_at | 2.103 |
| ZNF337 | 1565614_at | 2.096 |
| TTLL4 | 1557611_at | 2.092 |
| FUBP1 | 240307_at | 2.087 |
| NPTN | 228723_at | 2.086 |
| TPM4 | 235094_at | 2.079 |
| NCKAP1L | 209734_at | 2.071 |
| KRTAP19-1 | 1556410_a_at | 2.07 |
| SLC30A9 | 237051_at | 2.063 |
| HDAC3 | 240482_at | 2.062 |
| C10ORF18 | 244165_at | 2.046 |
| SMA4 | 238446_at | 2.035 |
| GBF1 | 233114_at | 2.03 |
| GABPA | 243498_at | 2.03 |
| SFRS15 | 243759_at | 2.028 |
| CREB3L2 | 237952_at | 2.013 |
| SLC2A8 | 239426_at | 2.012 |
| N4BP2L1 | 213375_s_at | 2.01 |
| IDS | 1559136_s_at | 2.001 |
| COBRA1 | 1556434_at | 1.985 |
| TXNL1 | 243664_at | 1.98 |
| LOC388135 | 230475_at | 1.979 |
| MTUS1 | 239576_at | 1.975 |
| TAF15 | 227891_s_at | 1.971 |
| HNRPD | 241702_at | 1.962 |
| TRIM46 | 238147_at | 1.96 |
| NBR1 | 1568856_at | 1.957 |
| WDR68 | 233782_at | 1.924 |

TABLE 1.1-continued

Upregulated CSC-associated genes (p < 0.05)

| GENESYMBOL | ID | Fold Change |
|---|---|---|
| HNRPD | 235999_at | 1.92 |
| BLID | 239672_at | 1.91 |
| LOC145786 | 229178_at | 1.907 |
| HOXD3 | 206601_s_at | 1.897 |
| AOC3 | 204894_s_at | 1.894 |
| PRPF38B | 230270_at | 1.888 |
| SLC20A1 | 230494_at | 1.884 |
| SEC16B | 1552880_at | 1.877 |
| FLT1 | 232809_at | 1.861 |
| HUWE1 | 214673_s_at | 1.858 |
| BUB1 | 216277_at | 1.856 |
| GPR135 | 241085_at | 1.851 |
| PSEN1 | 242875_at | 1.851 |
| KIAA0907 | 230028_at | 1.83 |
| POLR2J2 | 1552622_s_at | 1.828 |
| SFRS15 | 222311_s_at | 1.818 |
| CBS | 240517_at | 1.818 |
| ETS1 | 241435_at | 1.797 |
| LRRFIP1 | 239379_at | 1.796 |
| OCIAD1 | 235537_at | 1.794 |
| LRCH3 | 229387_at | 1.793 |
| CCDC14 | 240884_at | 1.771 |
| HNRNPC | 235500_at | 1.769 |
| DCUN1D2 | 240478_at | 1.76 |
| NPAS2 | 1557690_x_at | 1.76 |
| POFUT2 | 207448_at | 1.759 |
| CHD2 | 244443_at | 1.757 |
| TMEM165 | 1560622_at | 1.756 |
| FLJ31306 | 239432_at | 1.753 |
| HPS1 | 239382_at | 1.749 |
| WTAP | 1560274_at | 1.747 |
| TNPO1 | 1556116_s_at | 1.739 |
| ZFHX3 | 215828_at | 1.737 |
| AKR1CL2 | 1559982_s_at | 1.732 |
| C20ORF4 | 234654_at | 1.731 |
| CCDC57 | 214818_at | 1.703 |
| MALAT1 | 224568_x_at | 1.699 |
| EWSR1 | 229966_at | 1.686 |
| MYO10 | 244350_at | 1.677 |
| MALAT1 | 223940_x_at | 1.659 |
| ATXN2L | 207798_s_at | 1.656 |
| PDK1 | 239798_at | 1.654 |
| POLR2J2 | 1552621_at | 1.652 |
| CENPJ | 220885_s_at | 1.64 |
| PDSS1 | 236298_at | 1.64 |
| UNK | 1562434_at | 1.637 |
| BDP1 | 224227_s_at | 1.632 |
| N4BP2L2 | 235547_at | 1.631 |
| MDM4 | 235589_s_at | 1.629 |
| SNORA28 | 241843_at | 1.628 |
| ZFX | 207920_x_at | 1.625 |
| NAPA | 239362_at | 1.624 |
| PRO1073 | 228582_x_at | 1.607 |
| MLL | 212079_s_at | 1.599 |
| SGOL2 | 235425_at | 1.591 |
| RBM25 | 1557081_at | 1.57 |
| BARD1 | 205345_at | 1.559 |
| LOC388969 | 232145_at | 1.555 |
| GGT1 | 211417_x_at | 1.555 |
| FAM62C | 239770_at | 1.551 |
| TTC9C | 1569189_at | 1.55 |
| TCAG7.907 | 238678_at | 1.546 |
| OSGEP | 242930_at | 1.541 |
| RHOBTB2 | 1556645_s_at | 1.538 |
| C5ORF24 | 229098_s_at | 1.531 |
| RBM4 | 213718_at | 1.53 |
| SLC2A11 | 232167_at | 1.529 |
| DDX17 | 213998_s_at | 1.528 |
| C22ORF30 | 216555_at | 1.521 |
| C9ORF85 | 244160_at | 1.52 |
| DNM1L | 236032_at | 1.503 |
| SQLE | 213577_at | 1.502 |
| CRIPAK | 228318_s_at | 1.486 |
| ZNF800 | 227101_at | 1.484 |
| RAD54L | 204558_at | 1.483 |
| TAF1B | 239046_at | 1.468 |
| THRAP3 | 217847_s_at | 1.464 |
| CNIH3 | 232758_s_at | 1.451 |
| UQCC | 229672_at | 1.451 |
| HOXA2 | 228642_at | 1.44 |
| RBM26 | 229433_at | 1.43 |
| RFT1 | 240281_at | 1.426 |
| MTERFD3 | 225341_at | 1.422 |
| LOC641298 | 208118_x_at | 1.419 |
| ZNF326 | 241720_at | 1.418 |
| NBPF16 | 201104_x_at | 1.411 |
| ASPM | 232238_at | 1.411 |
| RNF43 | 228826_at | 1.401 |
| IPW | 213447_at | 1.399 |
| TTC3 | 208664_s_at | 1.396 |
| USP36 | 224979_s_at | 1.393 |
| KIAA0841 | 36888_at | 1.389 |
| NEK1 | 213328_at | 1.381 |
| AMZ2 | 227567_at | 1.377 |
| TBC1D8 | 204526_s_at | 1.373 |
| STK36 | 231806_s_at | 1.362 |
| SF3B1 | 214305_s_at | 1.359 |
| HELLS | 242890_at | 1.359 |
| SYNE2 | 202761_s_at | 1.356 |
| KIAA1267 | 224489_at | 1.355 |
| C14ORF135 | 1563259_at | 1.353 |
| SF3B1 | 201070_x_at | 1.35 |
| CLN8 | 229958_at | 1.344 |
| STK36 | 234005_x_at | 1.335 |
| ZNF226 | 219603_s_at | 1.332 |
| COQ4 | 218328_at | 1.328 |
| DTX3 | 49051_g_at | 1.32 |
| WFS1 | 1555270_a_at | 1.315 |
| ZNF251 | 226754_at | 1.313 |
| ARS2 | 201679_at | 1.307 |
| ATAD2 | 235266_at | 1.304 |
| CCDC73 | 239848_at | 1.294 |
| BCL9L | 227616_at | 1.291 |
| MET | 213816_s_at | 1.283 |
| NFATC2IP | 217527_s_at | 1.272 |
| CHD8 | 212571_at | 1.27 |
| TNRC6A | 234734_s_at | 1.268 |
| OSBPL5 | 233734_s_at | 1.261 |
| COIL | 203653_s_at | 1.259 |
| CPEB2 | 226939_at | 1.251 |
| TBC1D8 | 221592_at | 1.246 |
| RUNX3 | 204198_s_at | 1.233 |
| LBA1 | 213261_at | 1.225 |
| CENPJ | 234023_s_at | 1.22 |
| MARCH6 | 201737_s_at | 1.219 |
| ANKRD44 | 226641_at | 1.218 |
| NAPE-PLD | 242635_s_at | 1.216 |
| C12ORF48 | 220060_s_at | 1.216 |
| CCDC93 | 219774_at | 1.208 |
| ZUFSP | 228330_at | 1.205 |
| SMC6 | 218781_at | 1.203 |
| TAOK3 | 220761_s_at | 1.195 |
| JARID1A | 226367_at | 1.192 |
| DCLRE1C | 242927_at | 1.187 |
| TTC26 | 233999_at | 1.184 |
| EIF4G3 | 201935_s_at | 1.174 |
| ORMDL1 | 223187_s_at | 1.171 |
| TCOF1 | 202385_s_at | 1.169 |
| CCDC52 | 234995_at | 1.166 |
| PMS2L3 | 214473_x_at | 1.159 |
| HERC5 | 219863_at | 1.156 |
| CASC5 | 228323_at | 1.144 |
| SON | 201085_s_at | 1.144 |
| APBB2 | 40148_at | 1.139 |
| LOC338799 | 226369_at | 1.137 |
| PHC1 | 218338_at | 1.123 |
| DEPDC1 | 232278_s_at | 1.119 |
| NRP2 | 210841_s_at | 1.106 |
| ZMYND8 | 209049_s_at | 1.102 |
| CEP55 | 218542_at | 1.096 |

TABLE 1.2

Highly upregulated genes as detected by RT-PCR

| Description | Gname | ABCB5+/ABCB5− Fold change |
|---|---|---|
| Angiopoietin-like 3 | ANGPT5 | 3.0596 |
| Brain-specific angiogenesis inhibitor 1 | FLJ41988 | 3.0596 |
| Cadherin 5, type 2, VE-cadherin (vascular epithelium) | 7B4/CD144 | 3.0596 |
| Epidermal growth factor (beta-urogastrone) | HOMG4/URG | 187.8365 |
| C-fos induced growth factor (vascular endothelial growth factor D) | VEGF-D/VEGFD | 3.5884 |
| Hepatocyte growth factor (hepapoietin A; scatter factor) | F-TCF/HGFB | 4.542 |
| Heparanase | HPA/HPR1 | 286.6871 |
| Insulin-like growth factor 1 (somatomedin C) | IGFI | 4.7022 |
| Jagged 1 (Alagille syndrome) | AGS/AHD | 1566.5046 |
| Laminin, alpha 5 | KIAA1907 | 3.8727 |
| Platelet/endothelial cell adhesion molecule (CD31 antigen) | CD31/PECAM-1 | 11.9037 |
| Plexin domain containing 1 | DKFZp686F0937/TEM3 | 3.4184 |
| Stabilin 1 | CLEVER-1/FEEL-1 | 4.357 |
| Transforming growth factor, alpha | TFGA | 3549.3357 |
| Tumor necrosis factor (TNF superfamily, member 2) | DIF/TNF-alpha | 4.0652 |
| Vascular endothelial growth factor C | Flt4-L/VRP | 446.7529 |

TABLE 2

Downregulated CSC-associated genes (p < 0.05)

| GENESYMBOL | ID | Fold Change |
|---|---|---|
| ECHDC1 | 233124_s_at | 0.943 |
| DARS | 201624_at | 0.928 |
| GALNT1 | 201722_s_at | 0.926 |
| CGGBP1 | 224600_at | 0.913 |
| CSE1L | 201112_s_at | 0.911 |
| GMFB | 202544_at | 0.904 |
| RPL7L1 | 225515_s_at | 0.899 |
| SKP1 | 200718_s_at | 0.898 |
| IGHMBP2 | 215980_s_at | 0.893 |
| LOC137886 | 212934_at | 0.886 |
| CSE1L | 210766_s_at | 0.885 |
| ERRFI1 | 224657_at | 0.881 |
| MAP2K4 | 203266_s_at | 0.881 |
| TNFAIP1 | 201207_at | 0.88 |
| TBXA2R | 207554_x_at | 0.877 |
| SEPHS1 | 208940_at | 0.875 |
| IPO7 | 200993_at | 0.875 |
| C16ORF63 | 225087_at | 0.872 |
| INSIG2 | 209566_at | 0.872 |
| TFB1M | 228075_x_at | 0.87 |
| PAK1 | 226507_at | 0.869 |
| C14ORF156 | 221434_s_at | 0.867 |
| SMYD2 | 212922_s_at | 0.867 |
| ENTPD5 | 231676_s_at | 0.867 |
| PPP3CA | 202457_s_at | 0.867 |
| MBNL1 | 201152_s_at | 0.867 |
| MRPL42 | 217919_s_at | 0.866 |
| SUPT7L | 201838_s_at | 0.865 |
| PMP22 | 210139_s_at | 0.865 |
| GABARAPL2 | 209046_s_at | 0.863 |
| PITPNA | 201190_s_at | 0.863 |
| C2ORF30 | 224630_at | 0.851 |
| TXNDC12 | 223017_at | 0.849 |
| POP4 | 202868_s_at | 0.847 |
| MRPL51 | 224334_s_at | 0.846 |
| AK3 | 224655_at | 0.845 |
| GPR107 | 211979_at | 0.843 |
| TMEM126B | 221622_s_at | 0.843 |
| PSMA2 | 201316_at | 0.839 |
| KIAA1737 | 225623_at | 0.837 |
| TRAPPC2L | 218354_at | 0.837 |
| RLBP1L1 | 224996_at | 0.835 |
| CCDC127 | 226515_at | 0.835 |
| CPNE3 | 202119_s_at | 0.833 |
| HIAT1 | 225222_at | 0.832 |
| MECR | 218664_at | 0.832 |
| ACBD6 | 225317_at | 0.83 |
| SLC16A1 | 202235_at | 0.83 |
| ANXA4 | 201302_at | 0.83 |
| DNAJC21 | 230893_at | 0.829 |
| C22ORF28 | 200042_at | 0.829 |
| SPOPL | 225659_at | 0.828 |
| PDHB | 211023_at | 0.827 |
| EIF2S1 | 201144_s_at | 0.824 |
| LOC645166 | 228158_at | 0.823 |
| CAMK2D | 225019_at | 0.823 |
| LIMS1 | 212687_at | 0.822 |
| VTI1B | 209452_s_at | 0.821 |
| YY1 | 224711_at | 0.821 |
| TRAPPC2 | 219351_at | 0.821 |
| LOC126917 | 225615_at | 0.819 |
| STX8 | 204690_at | 0.819 |
| NANP | 228073_at | 0.817 |
| NDFIP1 | 217800_s_at | 0.815 |
| UBE3C | 1560739_a_at | 0.815 |
| KPNA6 | 226976_at | 0.814 |
| C19ORF42 | 219097_x_at | 0.813 |
| DHX40 | 218277_s_at | 0.812 |
| NUCB2 | 203675_at | 0.812 |
| RAB1A | 213440_at | 0.81 |
| USP8 | 229501_s_at | 0.808 |
| MAP1LC3B | 208785_s_at | 0.808 |
| PDHB | 208911_s_at | 0.807 |
| SH2B3 | 203320_at | 0.806 |
| PPP1R3D | 204554_at | 0.805 |
| DEGS1 | 209250_at | 0.804 |
| HSDL2 | 209513_s_at | 0.803 |
| LOC203547 | 225556_at | 0.802 |
| CANX | 238034_at | 0.8 |
| PSMA3 | 201532_at | 0.798 |
| PIGY | 224660_at | 0.793 |
| CYB5R3 | 1554574_a_at | 0.793 |
| BRI3 | 223376_s_at | 0.792 |
| CREB1 | 204313_s_at | 0.791 |
| LOC389203 | 225014_at | 0.79 |
| WDR41 | 218055_s_at | 0.789 |
| C9ORF78 | 218116_at | 0.789 |
| GNPDA1 | 202382_s_at | 0.787 |
| RPE | 225039_at | 0.787 |
| HSPA4L | 205543_at | 0.786 |
| SEPT11 | 201307_at | 0.784 |
| HEATR2 | 241352_at | 0.784 |
| ENAH | 222433_at | 0.783 |
| MED19 | 226300_at | 0.782 |
| TBC1D5 | 201814_at | 0.782 |
| EMP2 | 225079_at | 0.781 |
| STX11 | 235670_at | 0.778 |
| ANKH | 229176_at | 0.776 |
| ENDOD1 | 212573_at | 0.775 |
| IL13RA1 | 201887_at | 0.775 |
| RAB14 | 200927_s_at | 0.772 |
| TMEM30A | 232591_s_at | 0.771 |
| DDX52 | 212834_at | 0.771 |
| PTPMT1 | 229535_at | 0.769 |
| SRPRB | 218140_x_at | 0.767 |
| FAM98A | 212333_at | 0.767 |
| SRP72 | 208803_s_at | 0.766 |
| RPE | 221770_at | 0.766 |
| HOXB9 | 216417_x_at | 0.766 |
| MAEA | 207922_s_at | 0.765 |
| GHITM | 1554510_s_at | 0.764 |
| CAPZB | 201949_x_at | 0.764 |
| ANKRD52 | 228257_at | 0.762 |
| MOBKL1B | 214812_s_at | 0.762 |

TABLE 2-continued

Downregulated CSC-associated genes (p < 0.05)

| GENESYMBOL | ID | Fold Change |
|---|---|---|
| MIA3 | 1569057_s_at | 0.759 |
| UBE2E3 | 210024_s_at | 0.758 |
| CAMK2D | 228555_at | 0.758 |
| UBXD7 | 212840_at | 0.754 |
| C18ORF10 | 213617_s_at | 0.754 |
| HSD17B1 | 228595_at | 0.753 |
| PDLIM5 | 212412_at | 0.752 |
| SRP72 | 208801_at | 0.751 |
| ZNF618 | 226590_at | 0.75 |
| TSPAN31 | 203227_s_at | 0.744 |
| MAP3K15 | 200979_at | 0.741 |
| C18ORF10 | 212055_at | 0.737 |
| ATP5I | 207335_x_at | 0.737 |
| TOX4 | 201685_s_at | 0.73 |
| TBXA2R | 336_at | 0.73 |
| COL4A2 | 211966_at | 0.729 |
| TIMM23 | 218119_at | 0.723 |
| NDUFAF2 | 228355_s_at | 0.722 |
| FOXN3 | 218031_s_at | 0.721 |
| EIF2S1 | 201142_at | 0.717 |
| NDUFB6 | 203613_s_at | 0.712 |
| TM6SF1 | 1558102_at | 0.704 |
| ELOVL2 | 213712_at | 0.699 |
| PPP1R7 | 201213_at | 0.698 |
| BAT3 | 230513_at | 0.697 |
| ZNF668 | 219047_s_at | 0.691 |
| ERBB3 | 1563253_s_at | 0.691 |
| C12ORF45 | 226349_at | 0.688 |
| PGRMC2 | 213227_at | 0.686 |
| NUDT4 | 212183_at | 0.685 |
| AABHD7 | 239579_at | 0.661 |
| CEP27 | 228744_at | 0.651 |
| RAB11FIP3 | 216043_x_at | 0.551 |
| FHL3 | 218818_at | 0.546 |
| NAALAD2 | 1554506_x_at | 0.464 |
| LOC219731 | 1557208_at | 0.419 |

TABLE 3

CSC-genes annotations

| Name | Entrez Gene ID for Human | Affymetrix | Fold Change | Networks | Location | Type | Drugs |
|---|---|---|---|---|---|---|---|
| Actin | | — | | 1 | Unknown | group | |
| ADA | 100 | — | | 8 | Cytoplasm | enzyme | pentostatin, vidarabine |
| Adaptor protein 2 | | — | | 8 | Unknown | complex | |
| AFP | 174 | — | | 5 | Extracellular Space | transporter | |
| AGT | 183 | — | | 8 | Extracellular Space | other | |
| AHR | 196 | — | | 7 | Nucleus | ligand-dependent nuclear receptor | |
| AKAP9 | 10142 | 215483_at | 2.168 | 1 | Cytoplasm | other | |
| Akt | | — | | 2 | Unknown | group | |
| amino acids | | — | | 6 | Unknown | chemical - endogenous mammalian | |
| AMPH | 273 | — | | 8 | Plasma Membrane | other | |
| AMZ2 | 51321 | 227567_at | 1.377 | 8 | Unknown | other | |
| ANAPC1 | 64682 | — | | 4 | Nucleus | other | |
| ANAPC10 | 10393 | — | | 4 | Nucleus | enzyme | |
| ANAPC11 | 51529 | — | | 4 | Unknown | enzyme | |
| ANAPC13 | 25847 | — | | 4 | Unknown | other | |
| ANAPC2 | 29882 | — | | 4 | Nucleus | enzyme | |
| ANAPC4 | 29945 | — | | 4 | Unknown | enzyme | |
| ANAPC5 | 51433 | 235926_at | 2.631 | 4 | Nucleus | enzyme | |
| ANAPC7 | 51434 | — | | 4 | Unknown | other | |
| ANK2 | 287 | 202921_s_at | 4.162 | 4 | Plasma Membrane | other | |
| ANKRD28 | 23243 | 241063_at | 2.297 | 13 | Unknown | other | |
| AOC3 | 8639 | 204894_s_at | 1.894 | 2 | Plasma Membrane | enzyme | |
| AP2A2 | 161 | — | | 8 | Cytoplasm | transporter | |
| APBB2 | 323 | 40148_at | 1.139 | 9 | Cytoplasm | other | |
| APP | 351 | — | | 9 | Plasma Membrane | other | AAB-001 |
| ARD1A | 8260 | — | | 8 | Nucleus | enzyme | |
| Arf | | — | | 8 | Unknown | group | |
| ARF5 | 381 | — | | 8 | Cytoplasm | transporter | |
| ARHGDIB | 397 | — | | 7 | Cytoplasm | other | |
| ASCC3L1 (includes EG: 23020) | 23020 | 214982_at | 3.009 | 9 | Nucleus | enzyme | |

TABLE 3-continued

CSC-genes annotations

| Name | Entrez Gene ID for Human | Affymetrix | Fold Change | Networks | Location | Type | Drugs |
|---|---|---|---|---|---|---|---|
| ASCL1 | 429 | — | | 9 | Nucleus | transcription regulator | |
| ASPM | 259266 | 232238_at | 1.411 | 3 | Nucleus | other | |
| ATAD2 | 29028 | 235266_at | 1.304 | 7 | Unknown | other | |
| ATP | | — | | 9 | Unknown | chemical - endogenous mammalian | |
| ATXN2L | 11273 | 207798_s_at | 1.656 | 9 | Unknown | other | |
| BARD1 | 580 | 205345_at | 1.559 | 1 | Nucleus | transcription regulator | |
| BCL2 | 596 | — | | 6 | Cytoplasm | other | oblimersen, (−)-gossypol |
| BCL9L | 283149 | 227616_at | 1.291 | 6 | Cytoplasm | other | |
| BDP1 | 55814 | 224227_s_at | 1.632 | 9 | Nucleus | transcription regulator | |
| beta-estradiol | | — | | 3 | Unknown | chemical - endogenous mammalian | |
| BRF1 | 2972 | — | | 9 | Nucleus | transcription regulator | |
| BUB1 (includes EG: 699) | 699 | 233445_at | 3.209 | 5 | Nucleus | kinase | |
| BUB1B | 701 | — | | 4 | Nucleus | kinase | |
| C12ORF48 | 55010 | 220060_s_at | 1.216 | | Unknown | other | |
| C12ORF51 | 283450 | 1557529_at | 3.632 | 4 | Unknown | other | |
| CABIN1 | 23523 | 1557581_x_at | 3.052 | 1 | Nucleus | other | |
| Calmodulin | | — | | 1 | Unknown | group | |
| CASC5 | 57082 | 228323_at | 1.144 | 3 | Nucleus | other | |
| CASP3 | 836 | — | | 4 | Cytoplasm | peptidase | IDN-6556 |
| CASP6 | 839 | — | | 9 | Cytoplasm | peptidase | |
| CBS | 875 | 240517_at | 1.818 | 1 | Cytoplasm | enzyme | |
| CD151 | 977 | — | | 7 | Plasma Membrane | other | |
| CDC14B | 8555 | 234605_at | 2.512 | 5 | Nucleus | phosphatase | |
| CDC16 | 8881 | 242359_at | 6.261 | 4 | Nucleus | other | |
| CDC20 | 991 | — | | 3 | Nucleus | other | |
| CDC23 (includes EG: 8697) | 8697 | — | | 4 | Nucleus | enzyme | |
| CDC26 | 246184 | — | | 4 | Nucleus | other | |
| CDC27 | 996 | — | | 4 | Nucleus | other | |
| CDC5L | 988 | 222179_at | 1.292 | 9 | Nucleus | other | |
| CDK2 | 1017 | — | | 7 | Nucleus | kinase | BMS-387032, flavopiridol |
| CDKN1A | 1026 | — | | 7 | Nucleus | kinase | |
| CDT1 | 81620 | — | | 7 | Nucleus | other | |
| CDX1 | 1044 | — | | 9 | Nucleus | transcription regulator | |
| CENPJ | 55835 | 220885_s_at | 1.64 | 4 | Nucleus | transcription regulator | |
| CEP55 | 55165 | 218542_at | 1.096 | 5 | Unknown | other | |
| CHD8 | 57680 | 212571_at | 1.27 | 1 | Nucleus | enzyme | |
| CHEK2 | 11200 | — | | 5 | Nucleus | kinase | |
| CHRM3 | 1131 | — | | 8 | Plasma Membrane | G-protein coupled receptor | fesoterodine, ABT-089, atropine/edrophonium, cyclopentolate/ phenylephrine, ipratropium/albuterol, trihexyphenidyl, carbamylcholine, darifenacin, methacholine, diphenhydramine, quinidine, procyclidine, trospium, atropine sulfate/benzoic acid/hyoscyamine/ methenamine/methylene blue/phenyl salicylate, homatropine, dicyclomine, |

TABLE 3-continued

CSC-genes annotations

| Name | Entrez Gene ID for Human | Affymetrix | Fold Change | Networks | Location | Type | Drugs |
|---|---|---|---|---|---|---|---|
| | | | | | | | methantheline, orphenadrine, fluoxetine/olanzapine, doxacurium, aspirin/caffeine/ orphenadrine, propantheline, tridihexethyl, biperiden, anisotropine methylbromide, glycopyrrolate, diphenhydramine/8-chlorotheophylline, atropine/ hyoscyamine/ phenobarbital/ scopolamine, atropine sulfate/diphenoxylate hydrochloride, pipecuronium, flavoxate, chlorpheniramine/ methscopolamine/ phenylephrine, mepenzolic acid, atropine sulfate/difenoxin hydrochloride, homatropine methylbromide, hydroxyamphetamine/ tropicamide, cisatracurium, hyoscyamine/ phenobarbital, bethanechol, olanzapine, oxybutynin, tropicamide, solifenacin, cyclopentolate, tolterodine, cevimeline, acetylcholine, ipratropium, atropine, pilocarpine, benztropine, hyoscyamine, arecoline, scopolamine, N-methylscopolamine, tiotropium, carbinoxamine, buclizine, diphenhydramine/ phenylephrine, brompheniramine |
| CIB1 | 10519 | — | | 7 | Nucleus | other | |
| Ck2 | | — | | 1 | Unknown | complex | |
| CKM | 1158 | — | | 5 | Cytoplasm | kinase | |
| CLIC1 | 1192 | — | | 9 | Nucleus | ion channel | |
| CLIC4 | 25932 | — | | 6 | Cytoplasm | ion channel | |
| CLIC5 | 53405 | — | | 1 | Cytoplasm | ion channel | |
| CLN8 | 2055 | 229958_at | 1.344 | | Cytoplasm | other | |
| COIL | 8161 | 203653_s_at | 1.259 | 6 | Nucleus | other | |
| COL4A1 | 1282 | — | | 5 | Extracellular Space | other | collagenase |
| COPB1 | 1315 | — | | 8 | Cytoplasm | transporter | |
| Creb | | | | 2 | Unknown | group | |
| CREB3L2 | 64764 | 237952_at | 2.013 | 3 | Unknown | other | |
| CRIPAK | 285464 | 228318_s_at | 1.486 | | Cytoplasm | other | |
| CROP | 51747 | 242389_at | 2.121 | 7 | Nucleus | other | |

TABLE 3-continued

CSC-genes annotations

| Name | Entrez Gene ID for Human | Affymetrix | Fold Change | Networks | Location | Type | Drugs |
|---|---|---|---|---|---|---|---|
| CRY1 | 1407 | — | | 7 | Nucleus | enzyme | |
| CTNNA1 | 1495 | — | | 6 | Plasma Membrane | other | |
| CTNNAL1 | 8727 | — | | 6 | Plasma Membrane | other | |
| CTNNB1 | 1499 | — | | 6 | Nucleus | transcription regulator | |
| CUL4A | 8451 | 232466_at | 2.607 | 1 | Nucleus | other | |
| DAPK1 | 1612 | — | | 6 | Cytoplasm | kinase | |
| DCLRE1C | 64421 | 242927_at | 1.187 | | Nucleus | enzyme | |
| DDX17 | 10521 | 213998_s_at | 1.528 | 6 | Nucleus | enzyme | |
| DENND4A | 10260 | 230607_at | 2.368 | 1 | Nucleus | other | |
| DMD | 1756 | — | | 8 | Plasma Membrane | other | |
| DNM1L | 10059 | 236032_at | 1.503 | 2 | Cytoplasm | enzyme | |
| DSN1 | 79980 | — | | 3 | Nucleus | other | |
| DTX | | — | | 3 | Unknown | group | |
| DTX1 | 1840 | — | | 3 | Nucleus | transcription regulator | |
| DTX2 | 113878 | — | | 3 | Nucleus | other | |
| DTX3 | 196403 | 49051_g_at | 1.32 | 3 | Cytoplasm | other | |
| DUB | | — | | 18 | Unknown | group | |
| DVL1 | 1855 | — | | 6 | Cytoplasm | other | |
| DVL2 | 1856 | — | | 6 | Cytoplasm | other | |
| Dynamin | | — | | 2 | Unknown | group | |
| EGFR | 1956 | — | | 7 | Plasma Membrane | kinase | cetuximab, AEE 788, panitumumab, BMS-599626, ARRY-334543, XL647, canertinib, gefitinib, HKI-272, PD 153035, lapatinib, vandetanib, erlotinib |
| EIF4G3 | 8672 | 201935_s_at | 1.174 | 4 | Cytoplasm | translation regulator | |
| EPOR | 2057 | — | | 9 | Plasma Membrane | transmembrane receptor | erythropoietin, darbepoetin alfa, continuous erythropoietin receptor activator |
| ERBB2 | 2064 | — | | 3 | Plasma Membrane | kinase | trastuzumab, BMS-599626, ARRY-334543, XL647, CP-724, 714, HKI-272, lapatinib, erlotinib |
| ETS1 | 2113 | 241435_at | 1.797 | 2 | Nucleus | transcription regulator | |
| EWSR1 | 2130 | 229966_at | 1.686 | 1 | Nucleus | other | |
| EXT1 | 2131 | 242126_at | 2.116 | 4 | Cytoplasm | enzyme | |
| FLOT1 | 10211 | — | | 3 | Plasma Membrane | other | |
| FLT1 | 2321 | 232809_s_at | 1.861 | 2 | Plasma Membrane | kinase | sunitinib, axitinib, CEP 7055 |
| FMR1 | 2332 | — | | 7 | Nucleus | other | |
| FRK | 2444 | — | | 9 | Nucleus | kinase | |
| FUBP1 | 8880 | 240307_at | 2.087 | 1 | Nucleus | transcription regulator | |
| FZR1 | 51343 | — | | 4 | Nucleus | other | |
| GABPA | 2551 | 243498_at | 2.03 | 2 | Nucleus | transcription regulator | |
| GBF1 | 8729 | 233114_at | 2.03 | 8 | Cytoplasm | other | |
| GGT1 | 2678 | 211417_x_at | 1.555 | 6 | Cytoplasm | enzyme | |
| GPD2 | 2820 | 243598_at | 2.13 | 3 | Cytoplasm | enzyme | |
| HDAC3 | 8841 | 240482_at | 2.062 | 1 | Nucleus | transcription regulator | tributyrin, PXD101, pyroxamide, MGCD0103, vorinostat, FR 901228 |
| HECW1 | 23072 | 237295_at | 11.843 | 6 | Cytoplasm | enzyme | |
| HELLS | 3070 | 242890_at | 1.359 | 3 | Nucleus | enzyme | |
| HERC5 | 51191 | 219863_at | 1.156 | 6 | Cytoplasm | enzyme | |
| Histone h3 | | — | | 1 | Unknown | group | |
| HNRNPC | 3183 | 235500_at | 1.769 | 1 | Nucleus | other | |

TABLE 3-continued

CSC-genes annotations

| Name | Entrez Gene ID for Human | Affymetrix | Fold Change | Networks | Location | Type | Drugs |
|---|---|---|---|---|---|---|---|
| HNRPD | 3184 | 241702_at | 1.962 | 4 | Nucleus | transcription regulator | |
| HNRPH1 | 3187 | 213472_at | 2.332 | 8 | Nucleus | other | |
| HOXA2 | 3199 | 228642_at | 1.44 | 8 | Nucleus | transcription regulator | |
| HOXD3 | 3232 | 206601_s_at | 1.897 | 7 | Nucleus | transcription regulator | |
| HPS1 | 3257 | 239382_at | 1.749 | 14 | Cytoplasm | other | |
| HPS4 | 89781 | — | | 14 | Cytoplasm | other | |
| HSPA5 | 3309 | — | | 3 | Cytoplasm | other | |
| HUWE1 | 10075 | 214673_s_at | 1.858 | 6 | Nucleus | transcription regulator | |
| IFNG | 3458 | — | | 9 | Extracellular Space | cytokine | |
| IFNGR1 | 3459 | 242903_at | 2.171 | 4 | Plasma Membrane | transmembrane receptor | interferon gamma-1b |
| IL1B | 3553 | — | | 4 | Extracellular Space | cytokine | IL-1 trap |
| Insulin | | — | | 2 | Unknown | group | |
| IRS2 | 8660 | 236338_at | 2.162 | 2 | Cytoplasm | other | |
| ITGB3 | 3690 | — | | 7 | Plasma Membrane | transmembrane receptor | TP 9201, EMD121974, tirofiban |
| ITPR1 | 3708 | — | | 4 | Cytoplasm | ion channel | |
| JARID1A | 5927 | 226367_at | 1.192 | 9 | Nucleus | transcription regulator | |
| JARID2 | 3720 | 232835_at | 2.139 | 4 | Nucleus | transcription regulator | |
| Jnk | | — | | 2 | Unknown | group | |
| KIAA1267 | 284058 | 224489_at | 1.355 | 1 | Nucleus | other | |
| KIDINS220 | 57498 | 1557246_at | 2.97 | 6 | Nucleus | transcription regulator | |
| KIR2DL3 | 3804 | — | | 9 | Plasma Membrane | other | |
| KITLG (includes EG: 4254) | 4254 | — | | 9 | Extracellular Space | growth factor | |
| KLF6 | 1316 | — | | 5, 9 | Nucleus | transcription regulator | |
| LCN2 | 3934 | — | | 9 | Extracellular Space | transporter | |
| LMO2 | 4005 | — | | 9 | Nucleus | other | |
| LOC388135 | 388135 | 230475_at | 1.979 | 5 | Unknown | other | |
| LRRFIP1 | 9208 | 239379_at | 1.796 | 3 | Nucleus | transcription regulator | |
| MALAT1 | 378938 | 224568_x_at | 1.699 | | Unknown | other | |
| Mapk | | — | | 2 | Unknown | group | |
| MEF2C | 4208 | 236395_at | 2.104 | 2 | Nucleus | transcription regulator | |
| MET | 4233 | 213816_s_at | 1.283 | 2 | Plasma Membrane | kinase | |
| mGluR | | — | | 8 | Unknown | group | |
| MIS12 | 79003 | — | | 3 | Nucleus | other | |
| MLL | 4297 | 212079_s_at | 1.599 | 1 | Nucleus | transcription regulator | |
| MPL | 4352 | — | | 9 | Plasma Membrane | transmembrane receptor | SB-497115 |
| MTUS1 | 57509 | 239576_at | 1.975 | 1 | Unknown | other | |
| MYC | 4609 | — | | 6 | Nucleus | transcription regulator | |
| MYF6 | 4618 | — | | 5 | Nucleus | transcription regulator | |
| MYO10 | 4651 | 243159_x_at | 2.528 | 3 | Cytoplasm | other | |
| MYOD1 | 4654 | — | | 5 | Nucleus | transcription regulator | |
| N4BP2L1 | 90634 | 213375_s_at | 2.01 | | Unknown | other | |
| Nap125 | | — | | 16 | Unknown | group | |
| NAPA | 8775 | 239362_at | 1.624 | 2 | Cytoplasm | transporter | |
| NAPE-PLD | 222236 | 242635_s_at | 1.216 | 8 | Cytoplasm | enzyme | |
| NARG1 | 80155 | 1556381_at | 2.827 | 8 | Nucleus | transcription regulator | |
| NAT13 | 80218 | — | | 8 | Cytoplasm | enzyme | |
| NBPF15 | 284565 | 201104_x_at | 1.411 | 1 | Unknown | other | |
| NBR1 | 4077 | 1568856_at | 1.957 | 5 | Unknown | other | |

TABLE 3-continued

CSC-genes annotations

| Name | Entrez Gene ID for Human | Affymetrix | Fold Change | Networks | Location | Type | Drugs |
|---|---|---|---|---|---|---|---|
| NCKAP1L | 3071 | 209734_at | 2.071 | 16 | Plasma Membrane | other | |
| NCOA3 | 8202 | — | | 7 | Nucleus | transcription regulator | |
| NEK1 | 4750 | 213328_at | 1.381 | 6 | Nucleus | kinase | |
| NES | 10763 | — | | 5 | Cytoplasm | other | |
| NFATC2IP | 84901 | 217527_s_at | 1.272 | 1 | Nucleus | other | |
| NFkB | | — | | 2 | Unknown | complex | |
| NFKBIE (includes EG: 4794) | 4794 | — | | 13 | Nucleus | transcription regulator | |
| NMB | 4828 | — | | 8 | Extracellular Space | other | |
| NPAS2 | 4862 | 1557690_x_at | 1.76 | 7 | Nucleus | transcription regulator | |
| NPTN | 27020 | 228723_at | 2.086 | 1 | Plasma Membrane | other | |
| NRP2 | 8828 | 210841_s_at | 1.106 | 2, 3 | Plasma Membrane | kinase | |
| NUPL1 | 9818 | 241425_at | 2.179 | 17 | Nucleus | transporter | |
| OGG1 | 4968 | — | | 9 | Nucleus | enzyme | |
| OSBPL5 | 114879 | 233734_s_at | 1.261 | 3 | Cytoplasm | other | |
| OSGEP | 55644 | 242930_at | 1.541 | 3 | Unknown | peptidase | |
| P38 MAPK | | — | | 2 | Unknown | group | |
| PABPN1 | 8106 | 213046_at | 2.228 | 5 | Nucleus | other | |
| PAX3 | 5077 | — | | 7 | Nucleus | transcription regulator | |
| PCBP1 (includes EG: 5093) | 5093 | — | | 6 | Nucleus | translation regulator | |
| PDE4B | 5142 | 215671_at | 3.457 | 2 | Cytoplasm | enzyme | dyphylline, nitroglycerin, arofylline, tetomilast, L 869298, aminophylline, anagrelide, cilomilast, milrinone, rolipram, dipyridamole, L-826, 141, roflumilast, tolbutamide, theophylline, pentoxifylline, caffeine |
| PDE5A | 8654 | 239556_at | 2.24 | 4 | Cytoplasm | enzyme | dyphylline, nitroglycerin, DA-8159, aminophylline, sildenafil, dipyridamole, aspirin/dipyridamole, vardenafil, tolbutamide, tadalafil, theophylline, pentoxifylline |
| PDGF BB | | — | | 2 | Unknown | complex | |
| PDK1 | 5163 | 239798_at | 1.654 | 1 | Cytoplasm | kinase | |
| PDSS1 | 23590 | 236298_at | 1.64 | 15 | Unknown | enzyme | |
| PDXDC1 | 23042 | 1560014_s_at | 2.105 | 8 | Unknown | other | |
| PHC1 | 1911 | 218338_at | 1.123 | 5 | Nucleus | other | |
| PI3K | | — | | 2 | Unknown | complex | |
| PIP5K1C | 23396 | — | | 7 | Plasma Membrane | kinase | |
| PIP5K3 | 200576 | 1557719_at | 2.227 | 2 | Cytoplasm | kinase | |
| Pka | | — | | 1 | Unknown | complex | |
| Pkc(s) | | — | | 2 | Unknown | group | |
| PLAA | 9373 | — | | 4 | Cytoplasm | other | |
| PLC gamma | | — | | 2 | Unknown | group | |
| Pld | | — | | 8 | Unknown | group | |
| PLK1 | 5347 | — | | 7 | Nucleus | kinase | BI 2536 |
| PMS2L3 | 5387 | 214473_x_at | 1.159 | 3 | Unknown | other | |
| POLR2J2 | 246721 | 1552622_s_at | 1.828 | 1 | Nucleus | transcription regulator | |
| POU4F2 | 5458 | — | | 6 | Nucleus | transcription regulator | |

TABLE 3-continued

CSC-genes annotations

| Name | Entrez Gene ID for Human | Affymetrix | Fold Change | Networks | Location | Type | Drugs |
|---|---|---|---|---|---|---|---|
| PP2A | | — | | 6 | Unknown | complex | |
| PRDM5 | 11107 | — | | 5 | Nucleus | other | |
| PRKCB1 | 5579 | — | | 7 | Cytoplasm | kinase | enzastaurin, ruboxistaurin |
| progesterone | | — | | 8 | Unknown | chemical - endogenous mammalian | |
| PSEN1 | 5663 | 242875_at | 1.851 | 2 | Plasma Membrane | peptidase | (R)-flurbiprofen |
| PTEN | 5728 | — | | 3 | Cytoplasm | phosphatase | |
| PTK2 | 5747 | 234211_at | 2.539 | 2 | Cytoplasm | kinase | |
| PTPN12 | 5782 | — | | 7 | Cytoplasm | phosphatase | |
| PTPN14 | 5784 | — | | 6 | Cytoplasm | phosphatase | |
| PTPRA | 5786 | — | | 7 | Plasma Membrane | phosphatase | |
| PTPRD | 5789 | — | | 6 | Plasma Membrane | phosphatase | |
| PTPRE | 5791 | — | | 7 | Plasma Membrane | phosphatase | |
| PTPRS (includes EG: 5802) | 5802 | 1556116_s_at | 1.739 | 7 | Plasma Membrane | phosphatase | |
| RAB11FIP3 | 9727 | 228613_at | 2.546 | 8 | Cytoplasm | other | |
| RAB11FIP4 | 84440 | — | | 8 | Cytoplasm | other | |
| Rac | | — | | 2 | Unknown | group | |
| RAD50 | 10111 | — | | 5 | Nucleus | enzyme | |
| RAD54L | 8438 | 204558_at | 1.483 | 5 | Nucleus | enzyme | |
| RB1 | 5925 | — | | 9 | Nucleus | transcription regulator | |
| RBM25 | 58517 | 1557081_at | 1.57 | 7 | Nucleus | other | |
| RBM4 | 5936 | 213718_at | 1.53 | 7 | Nucleus | other | |
| RBM5 | 10181 | 209936_at | 2.249 | 6 | Nucleus | other | |
| RDBP | 7936 | — | | 3 | Nucleus | other | |
| RHOA | 387 | 240337_at | 2.143 | 2 | Cytoplasm | enzyme | |
| RHOBTB2 | 23221 | 1556645_s_at | 1.538 | | Unknown | enzyme | |
| RNA polymerase II | | — | | 1 | Unknown | complex | |
| RNU1A | 6060 | — | | 1 | Unknown | other | |
| RP13-122B23.3 | 25920 | 1556434_at | 1.985 | 3 | Nucleus | other | |
| RPL10 | 6134 | — | | 6 | Cytoplasm | other | |
| RUNX3 | 864 | 204198_s_at | 1.233 | 7 | Nucleus | transcription regulator | |
| SBF1 | 6305 | — | | 3 | Plasma Membrane | phosphatase | |
| SCMH1 | 22955 | — | | 5 | Nucleus | transcription regulator | |
| SCN3A | 6328 | — | | 4 | Plasma Membrane | ion channel | riluzole |
| SEC16A | 9919 | — | | 10 | Cytoplasm | phosphatase | |
| SEC16B | 89866 | 1552880_at | 1.877 | 10 | Nucleus | other | |
| Secretase gamma | | — | | 9 | Unknown | complex | |
| SF1 | 7536 | 210172_at | 2.452 | 1, 4 | Nucleus | transcription regulator | |
| SF3B1 | 23451 | 214305_s_at | 1.359 | 1 | Nucleus | other | |
| SFRS15 | 57466 | 243759_at | 2.028 | | Nucleus | other | |
| SGCA | 6442 | 1562729_at | 2.395 | 8 | Plasma Membrane | other | |
| SGCB | 6443 | — | | 8 | Plasma Membrane | other | |
| SGCD | 6444 | — | | 8 | Cytoplasm | other | |
| SGCG | 6445 | — | | 8 | Plasma Membrane | other | |
| SH2D1A (includes EG: 4068) | 4068 | — | | 5 | Cytoplasm | other | |
| SKIL | 6498 | — | | 4 | Nucleus | transcription regulator | |
| SLC29A1 | 2030 | — | | 9 | Plasma Membrane | transporter | |
| SLC2A11 | 66035 | 232167_at | 1.529 | 9 | Plasma Membrane | other | |
| SLC2A8 | 29988 | 239426_at | 2.012 | | Plasma Membrane | transporter | |
| SLC30A9 | 10463 | 237051_at | 2.063 | 7 | Nucleus | transporter | |
| SLC4A1 | 6521 | — | | 9 | Plasma Membrane | transporter | |

TABLE 3-continued

CSC-genes annotations

| Name | Entrez Gene ID for Human | Affymetrix | Fold Change | Networks | Location | Type | Drugs |
|---|---|---|---|---|---|---|---|
| SMAD4 | 4089 | — | | 6 | Nucleus | transcription regulator | |
| SMARCA5 | 8467 | — | | 9 | Nucleus | transcription regulator | |
| SMC5 | 23137 | — | | 12 | Nucleus | other | |
| SMC6 | 79677 | 218781_at | 1.203 | 12 | Nucleus | other | |
| SMN1 | 6606 | — | | 6 | Nucleus | other | |
| SNRPA1 | 6627 | 242146_at | 3.54 | 8 | Nucleus | other | |
| SNW1 | 22938 | — | | 5 | Nucleus | transcription regulator | |
| SON | 6651 | 201085_s_at | 1.144 | 5 | Nucleus | other | |
| SP4 | 6671 | — | | 3 | Nucleus | transcription regulator | |
| sphingomyelin | | — | | 9 | Unknown | chemical - endogenous mammalian | |
| SPN | 6693 | — | | 3 | Plasma Membrane | transmembrane receptor | |
| SPTBN1 | 6711 | — | | 4, 6, 8 | Plasma Membrane | other | |
| SQLE | 6713 | 213577_at | 1.502 | 3 | Cytoplasm | enzyme | |
| SQSTM1 | 8878 | — | | 5 | Cytoplasm | transcription regulator | |
| SRC | 6714 | — | | 6 | Cytoplasm | kinase | dasatinib, AZM-475271 |
| STK36 | 27148 | 231806_s_at | 1.362 | 6 | Unknown | kinase | |
| STRAP | 11171 | 1558002_at | 2.189 | 2 | Plasma Membrane | other | |
| STX3 | 6809 | — | | 7 | Plasma Membrane | transporter | |
| SUMO1 | 7341 | — | | 8 | Nucleus | enzyme | |
| SUMO2 | 6613 | — | | 9 | Nucleus | other | |
| SVIL | 6840 | 215279_at | 2.228 | 4 | Plasma Membrane | other | |
| SYNE2 | 23224 | 202761_s_at | 1.356 | 1 | Nucleus | other | |
| TAF15 | 8148 | 227891_s_at | 1.971 | 1 | Nucleus | transcription regulator | |
| TAF1A | 9015 | — | | 5 | Nucleus | transcription regulator | |
| TAF1B | 9014 | 239046_at | 1.468 | 5 | Nucleus | transcription regulator | |
| TAF1C | 9013 | — | | 5 | Nucleus | transcription regulator | |
| TAOK3 | 51347 | 220761_s_at | 1.195 | 2 | Cytoplasm | kinase | |
| Tap | | — | | 17 | Unknown | complex | |
| TBC1D8 | 11138 | 204526_s_at | 1.373 | 3 | Plasma Membrane | other | |
| TCERG1 | 10915 | — | | 8 | Nucleus | transcription regulator | |
| TCF7L2 | 6934 | — | | 6 | Nucleus | transcription regulator | |
| TCOF1 (includes EG: 6949) | 6949 | 202385_s_at | 1.169 | 1 | Nucleus | transporter | |
| TCR | | — | | 2 | Unknown | complex | |
| TERF2 | 7014 | — | | 5 | Nucleus | other | |
| TH1L | 51497 | — | | 3 | Nucleus | other | |
| THAP7 | 80764 | — | | 1 | Nucleus | other | |
| THRAP3 | 9967 | 217847_s_at | 1.464 | 1 | Nucleus | transcription regulator | |
| TIMP1 | 7076 | — | | 9 | Extracellular Space | other | |
| TNF | 7124 | — | | 4 | Extracellular Space | cytokine | adalimumab, etanercept, infliximab, CDP870, golimumab, thalidomide |
| TNRC6A | 27327 | 234734_s_at | 1.268 | 9 | Nucleus | other | |
| TP53 | 7157 | — | | 5 | Nucleus | transcription regulator | |
| TP53BP1 | 7158 | — | | 5 | Nucleus | transcription regulator | |

TABLE 3-continued

CSC-genes annotations

| Name | Entrez Gene ID for Human | Affymetrix | Fold Change | Networks | Location | Type | Drugs |
|---|---|---|---|---|---|---|---|
| TPM4 | 7171 | 235094_at | 2.079 | 8 | Cytoplasm | other | |
| Trans-hexaprenyl-transtransferase | | — | | 15 | Unknown | group | |
| TRIM33 | 51592 | 239716_at | 2.496 | 6 | Nucleus | transcription regulator | |
| TRIO | 7204 | 240773_at | 2.607 | 2 | Plasma Membrane | kinase | |
| tRNA adenylyl-transferase | | — | | 19 | Unknown | group | |
| tRNA cytidylyl-transferase | | — | | 19 | Unknown | group | |
| TRNT1 | 51095 | 243236_at | 2.295 | 19 | Cytoplasm | enzyme | |
| TRPV1 | 7442 | 1556229_at | 2.636 | 2 | Plasma Membrane | ion channel | SB-705498, capsaicin |
| TSG101 | 7251 | — | | 5, 7 | Nucleus | transcription regulator | |
| TSPAN7 | 7102 | — | | 7 | Plasma Membrane | other | |
| TTC3 | 7267 | 208664_s_at | 1.396 | 7 | Cytoplasm | other | |
| TXNL1 | 9352 | 243664_at | 1.98 | 9 | Cytoplasm | enzyme | |
| Ubiquitin | | — | | 1 | Unknown | group | |
| UGT | | — | | 7 | Unknown | group | |
| UGT1A6 | 54578 | 206094_x_at | 3.86 | 7 | Cytoplasm | enzyme | |
| USP36 | 57602 | 224979_s_at | 1.393 | 18 | Nucleus | peptidase | |
| Vegf | | — | | 2 | Unknown | group | |
| VEGFA | 7422 | — | | 3 | Extracellular Space | growth factor | bevacizumab, ranibizumab, pegaptanib |
| VEGFB (includes EG: 7423) | 7423 | — | | 3 | Extracellular Space | growth factor | |
| VPS28 | 51160 | — | | 5 | Cytoplasm | transporter | |
| VPS37B | 79720 | 236889_at | 2.85 | 5 | Nucleus | other | |
| WAS | 7454 | — | | 11 | Cytoplasm | other | |
| WDR68 | 10238 | 233782_at | 1.924 | 4 | Cytoplasm | other | |
| WFS1 | 7466 | 1555270_a_at | 1.315 | 3 | Cytoplasm | enzyme | |
| WIPF2 | 147179 | 216006_at | 2.916 | 11 | Unknown | other | |
| WT1 | 7490 | — | | 6 | Nucleus | transcription regulator | |
| WTAP | 9589 | 1560274_at | 1.747 | 2 | Nucleus | other | |
| XRCC5 | 7520 | 232633_at | 2.106 | 5 | Nucleus | enzyme | |
| YWHAG | 7532 | — | | 4 | Cytoplasm | other | |
| ZEB1 | 6935 | — | | 5 | Nucleus | transcription regulator | |
| ZFHX3 | 463 | 215828_at | 1.737 | 5 | Nucleus | transcription regulator | |
| ZFR | 51663 | 238970_at | 2.655 | | Nucleus | other | |
| ZFX | 7543 | 207920_x_at | 1.625 | 9 | Nucleus | transcription regulator | |
| ZMYND8 | 23613 | 209049_s_at | 1.102 | 7 | Nucleus | transcription regulator | |
| ZNF224 | 7767 | 216983_s_at | 2.986 | 6 | Nucleus | other | |
| ZNF226 | 7769 | 219603_s_at | 1.332 | 8 | Nucleus | transcription regulator | |
| ZNF326 | 284695 | 241720_at | 1.418 | | Nucleus | transcription regulator | |
| ZNF536 | 9745 | 233890_at | 3.303 | | Unknown | other | |
| ZWINT (includes EG: 11130) | 11130 | — | | 3 | Nucleus | other | |

TABLE 4

Cell Surface Genes

| Entrez Gene ID for Human | Name | Location |
|---|---|---|
| 7204 | TRIO | Plasma Membrane |
| 1956 | EGFR | Plasma Membrane |
| 7102 | TSPAN7 | Plasma Membrane |
| 977 | CD151 | Plasma Membrane |
| 2064 | ERBB2 | Plasma Membrane |
| 2321 | FLT1 | Plasma Membrane |
| 2030 | SLC29A1 | Plasma Membrane |
| 11171 | STRAP | Plasma Membrane |
| 8828 | NRP2 | Plasma Membrane |
| 4233 | MET | Plasma Membrane |
| 273 | AMPH | Plasma Membrane |
| 351 | APP | Plasma Membrane |
| 1756 | DMD | Plasma Membrane |
| 1495 | CTNNA1 | Plasma Membrane |
| 8727 | CTNNAL1 | Plasma Membrane |
| 10211 | FLOT1 | Plasma Membrane |
| 3459 | IFNGR1 | Plasma Membrane |
| 23396 | PIP5K1C | Plasma Membrane |
| 5663 | PSEN1 | Plasma Membrane |
| 6445 | SGCG | Plasma Membrane |
| 6693 | SPN | Plasma Membrane |
| 6711 | SPTBN1 | Plasma Membrane |
| 6840 | SVIL | Plasma Membrane |
| 2057 | EPOR | Plasma Membrane |
| 5789 | PTPRD | Plasma Membrane |
| 4352 | MPL | Plasma Membrane |
| 5786 | PTPRA | Plasma Membrane |
| 27020 | NPTN | Plasma Membrane |
| 3690 | ITGB3 | Plasma Membrane |
| 7442 | TRPV1 | Plasma Membrane |
| 8639 | AOC3 | Plasma Membrane |
| 1131 | CHRM3 | Plasma Membrane |
| 3804 | KIR2DL3 | Plasma Membrane |
| 287 | ANK2 | Plasma Membrane |
| 3071 | NCKAP1L | Plasma Membrane |
| 5791 | PTPRE | Plasma Membrane |
| 5802 | PTPRS | Plasma Membrane |
| 6305 | SBF1 | Plasma Membrane |
| 6328 | SCN3A | Plasma Membrane |
| 6442 | SGCA | Plasma Membrane |
| 6443 | SGCB | Plasma Membrane |
| 66035 | SLC2A11 | Plasma Membrane |
| 29988 | SLC2A8 | Plasma Membrane |
| 6521 | SLC4A1 | Plasma Membrane |
| 6809 | STX3 | Plasma Membrane |
| 11138 | TBC1D8 | Plasma Membrane |

A used herein "CSC-associated gene" refers to a gene whose expression or function is altered in cancer stem cells. CSC-associated genes include genes whose expression is signficantly altered, e.g., significantly upregulated or significantly downregulated, in cancer stem cells compared with non-cancer stem cells, e.g., cancer cells that are not stem cells, normal cells, etc. In some embodiments, genes that have significantly altered expression levels in cancer stem cells are identified by using an appropriate statistical test for establishing the significance of differences between expression levels in a cancer stem cell and a non-cancer stem cell. Tests for statistical significance are well known in the art and are exemplified in *Applied Statistics for Engineers and Scientists* by Petruccelli, Chen and Nandram 1999 Reprint Ed. The magnitude of up-, or down-, regulated expression of a CSC-associated gene in a cancer stem cell compared with a non-cancer stem cell may vary. In some embodiments, the expression level of a CSC-associated gene is at least 10%, at least 25%, at least 50%, at least 100%, at least 250%, at least 500%, or at least 1000% higher, or lower, than its expression level in a non-cancer stem cell. In other embodiments, the expression level of a CSC-associated gene is at least 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher, or lower, than its expression level a non-cancer stem cell.

CSC-associated genes are not limited to genes which are upregulated or downregulated in cancer stem cells. In some embodiments, a CSC-associated gene is a gene that may or may not have altered expression in a cancer stem cell, but that nevertheless functions in a pathway that is deregulated in cancer stem cells. Typically, deregulated pathways in cancer stem cells involve the product(s) of one or more genes whose expression is upregulated or downregulated and/or the product(s) of one or more genes with altered functionality, e.g., due to a mutation, thereby resulting in altered function of the pathway, e.g., overactivity or underactivity of the pathway.

In some embodiments, CSC-associated genes are identified in cancer stem cells of a breast cancer, prostate cancer, colon cancer, lung cancer, renal cancer or melanoma. In some instances, CSC-associated genes are identified in cancer stem cells of a melanoma, which are also referred to as malignant melanoma initiating cells (MMIC). Other cancer stem cells (e.g., non-ABCB5 CSCs) are known in the art.

Exemplary CSC-associated genes are disclosed in Tables 1-8. In some embodiments, a CSC-associated gene is selected from the group consisting of: ANK2, NCKAP1L, PTPRE, PTPRS, SBF1, SCN3A, SGCA, SGCB, SLC2A11, SLC2A8, SLC4A1, STX3, and TBC1D8. In some embodiments, the CSC-associated gene is one that is not a gene of the group consisting of EGFR, CD151, ERBB2, FLT1, SLC29A1, NRP2, MET, AMPH, APP, DMD, and ITGB3. In some embodiments, the CSC-associated gene is one that is not a gene of the group consisting of: TRIO, TSPAN7, STRAP, CTNNA1, CTNNAL1, FLOT1, IFNGR1, PIP5K1C, PSEN1, SGCG, SPN, SPTBN1, SVIL, EPOR, PTPRD, MPL, PTPRA, NPTN, TRPV1, AOC3, CHRM3, and KIR2DL3. In some embodiments, the CSC-associated gene is one that is not a gene that has previously been indicated as a tumor suppressor or oncogene. In some embodiments, the CSC-associated gene is one that is not a gene of the group consisting of: EWSR1, TP53, EGFR, ITPR1, NBR1, MLL, PTK2, PTPN14, RB1, JARID1A, SKIL, TNF, TP53BP1, TRIO, SF1, TAF15, NCOA3, RAD54L, CUL4A, SMARCA5, RAD50, AKAP9, DENND4A, DDX17, HECW1, ZMYND8, ANAPC13, ANAPC5, TH1L, TRIM33, and CHD8. In some embodiments, the CSC-associated gene is one that is not a gene of the group consisting of: BARD1, BCL2, CBS, CTNNB1, ERBB2, EWSR1, HPS1, IFNG, IL1B, PTEN, TP53, VEGFA, CHEK2, and HPS4.

In part, the disclosure relates to CSC-associated genes as well as the RNAs and polypeptides (CSC-associated RNA and polypeptides) that they encode and antibodies and antigen-binding fragments that specifically bind them. The CSC-associated genes, RNAs and polypeptides, encompass variants, homologues, and fragments. Variants may result from alternative splicing or allelic variation of certain genes provided in Tables 5. In general, homologues and alleles typically will share at least 90% nucleotide identity and/or at least 95% amino acid identity to the sequences of the cancer antigen nucleic acids and polypeptides, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. Homology can be calculated using various, publicly available software tools known in the art, such as those developed by NCBI (Bethesda, Md.) that are available through the internet. Exemplary tools include the BLAST system (e.g., using the default nucleic acid (Blastn) or protein (Blastp) search parameters) available from the website of the National Center for Biotechnology Information (NCBI) at the National Institutes of Health.

The CSC-associated genes are, among other things, useful for diagnosing cancer, such as breast cancer, prostate cancer, colon cancer, lung cancer, renal cancer or melanoma. Because CSC-associated gene expression is altered in cancer (e.g., upregulated or downregulated), the expression level of CSC-associated gene(s), e.g., a gene listed in Table 5 or 7, in an individual is diagnostic of cancer in that individual. Accordingly, the diagnostic methods disclosed herein can involve determining the CSC-associated RNA or protein (polypeptide) levels.

The term "individual" as used herein means any mammalian individual or subject, including, e.g., humans and non-human mammals, such as primates, rodents, and dogs. Individuals specifically intended for diagnosis and treatment using the methods described herein are preferably humans.

The expression level of CSC-associated gene(s) may be determined by using any of a number of methods known in the art. In some embodiments, the expression levels are determined from a biological sample (e.g., a test sample) obtained from a individual (e.g., a human). Exemplary, biological samples include an isolated cell, an isolated tissue, saliva, gingival secretions, cerebrospinal fluid (spinal fluid), gastrointestinal fluid, mucus, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, vitreal fluid, and nasal secretions. However, biological samples are not so limited and other exemplary biological specimens will be readily apparent to one of ordinary skill in the art. For the purposes of diagnosing melanoma, for example, the biological sample is preferably a skin tissue sample, e.g., a skin biopsy containing a suspicious lesion.

Expression levels of CSC-associated genes may be determined for diagnostic purposes using nucleic acid hybridization or nucleic acid amplification to detect the mRNAs that they encode. Methods for nucleic acid hybridization or amplification are well known in the art. In some embodiments, the nucleic acid amplification is real-time RT-PCR or RT-PCR. Other methods known to one of ordinary skill in the art could be employed to analyze mRNA levels, for example nucleic acid arrays, cDNA analysis, Northern analysis, and RNase Protection Assays. Nucleic acid arrays may be used to assay (e.g., for diagnostic purposes) the expression levels of multiple CSC-associated genes in parallel. Other suitable nucleic acid detection methods will be apparent to the skilled artisan.

Expression levels of CSC-associated genes may be determined for diagnostic purposes by detecting the polypeptides that they encode. Methods for detecting polypeptides are well known in the art. Exemplary polypeptide detection methods include, but are not limited to, Enzyme Linked Immunosorbent Assays (ELISA), radioimmunoassays (RIA), sandwich immunometric assays, flow cytometry, western blot assays, immunoprecipitation assays, immunohistochemistry, immunomicroscopy, lateral flow immunochromatographic assays, BIACORE technology, and proteomics methods, such as mass spectroscopy. Antibody arrays may be used to assay (e.g., for diagnostic purposes) the expression levels of multiple CSC-associated genes in parallel. Other suitable polypeptide detection methods will be apparent to the skilled artisan.

In some embodiments, e.g., where polypeptide, antibody or nucleic acid arrays are used, expression levels of up to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or more CSC-associated genes may be tested in parallel.

The diagnostic methods of the invention involve a comparison between expression levels of CSC-associated genes in a test sample and a reference value. The results of the comparison are diagnostic of cancer, e.g., melanoma. In some embodiments, the reference value is the expression level of the gene in a reference sample. A reference value may be a predetermined value and may also be determined from reference samples (e.g., control biological samples) tested in parallel with the test samples. A reference value may be a positive or negative control level. A reference value can be a single cut-off value, such as a median or mean or a range of values, such as a confidence interval. Reference values can be established for various subgroups of individuals, such as individuals predisposed to cancer, individuals having early or late stage cancer, male and/or female individuals, or individuals undergoing cancer therapy. The level of the reference value will depend upon the particular population or subgroup selected. For example, an apparently healthy population will have a different "normal" value than will a population which has cancer, or a population that has a predisposition for cancer. Appropriate ranges and categories for reference values can be selected with no more than routine experimentation by those of ordinary skill in the art.

The reference sample can be any of a variety of biological samples against which a diagnostic assessment may be made. Examples of reference samples include biological samples from control populations or control samples. Reference samples may be generated through manufacture to be supplied for testing in parallel with the test samples, e.g., reference sample may be supplied in diagnostic kits. When the reference sample is from a cancer, e.g., tumor tissue, the expression level of the reference sample (the reference value) is the expression level of the CSC-associated gene in the cancer. Similarly, when the reference sample is a normal sample, e.g., non-tumor tissue, the expression level of the reference sample (the reference value) is the expression level of the CSC-associated gene in the non-tumor tissue. Similarly, when the reference sample is a cancer stem cell sample, the expression level of the reference sample (the reference value) is the expression level of the CSC-associated gene in the cancer stem cell sample. In some embodiments, the reference sample is of a melanoma and the expression level of the reference sample is the expression level of the CSC-associated gene in melanoma. In some embodiments, the reference sample is of a non-melanoma tissue and the expression level of the reference sample is the expression level of the CSC-associated gene in non-melanoma tissue. Other appropriate reference samples will be apparent to the skilled artisan.

The diagnostic methods are based in part on a comparison of expression levels of CSC-associated genes between test samples and reference sample. In some embodiments, if the expression level of the CSC-associated gene in the test sample is about equal to the expression level of the CSC-associated gene in the reference sample, then the test sample and reference sample are likely of a similar origin, category or class. For example, if expression levels in a test sample and reference sample are about the same (e.g., not statistically significantly different), and the reference sample is from a normal tissue, then the test sample is likely a normal tissue sample, and a normal diagnosis could be indicated. Alternatively, if expression levels in a test sample and reference sample are about the same, and the reference sample is from a cancer tissue, then the test sample is likely a cancer sample, and a diagnosis of cancer could be indicated. In certain embodiments, if the expression level in a test sample and reference sample are about the same, and the reference sample is from a melanoma, then the test sample is likely a melanoma sample, and a diagnosis of melanoma could be indicated.

In some cases, depending on factors such as the particular CSC-associated gene(s) being evaluated, the condition being diagnosed, and the type of reference sample, an expression level of a CSC-associated gene in a test sample that is statistically significantly higher or statistically significantly lower than its expression level in a reference sample indicates a diagnosis. For example, when the CSC-associated gene is among those listed in Table 1 or 8 and the reference value is the expression level of the CSC-associated gene in a normal (e.g., non-cancerous) reference sample, if the expression level of the CSC-associated gene in the test sample is significantly higher than the expression level of the CSC-associated gene in the normal reference sample, the comparison indicates cancer, e.g., melanoma. Similarly, when the CSC-associated gene is among those listed in Table 1 or 8 and the reference value is the expression level of the CSC-associated gene in a cancer, e.g., melanoma, reference sample, if the expression level of the CSC-associated gene in the test sample is significantly lower than the expression level of the CSC-associated gene in the cancer reference sample, the comparison does not indicate cancer. Alternatively, when the CSC-associated gene is among those listed in Table 2 or 7 and the reference value is the expression level of the CSC-associated gene in a normal reference sample, if the expression level of the CSC-associated gene in the test sample is significantly lower than the expression level of the CSC-associated gene in the normal reference sample, the comparison indicates cancer. Similarly, when the CSC-associated gene is in Table 2 or 7 and the reference value is the expression level of the CSC-associated gene in a cancer, e.g., melanoma, reference sample, if the expression level of the CSC-associated gene in the test sample is significantly higher than the expression level of the CSC-associated gene in the cancer reference sample, the comparison does not indicate melanoma. Appropriate combinations of particular CSC-associated gene(s), conditions to be diagnosed, and types of reference samples, can be selected with no more than routine experimentation by those of ordinary skill in the art for use in the diagnostic methods disclosed herein.

The magnitude of the difference between the test sample and reference sample that is sufficient to indicate a diagnosis will depend on a variety of factors such as the particular CSC-associated gene(s) being evaluated, the condition being diagnosed, heterogeneity in healthy or disease populations from which samples are drawn, the type of reference sample, the magnitude of expression level of a CSC-associated gene, the assay being used, etc. It is well within the purview of the skilled artisan to determine the appropriate magnitude of difference between the test sample and reference sample that is sufficient to indicate a diagnosis. In some embodiments, the expression level of the CSC-associated gene in the test sample is at least 10%, at least 20%, at least 50%, at least 100%, at least 200%, at least 500%, at least 1000% or more higher than the expression level of the gene in the reference sample. In other embodiments, the expression level of the CSC-associated gene in the test sample is at least 10%, at least 20%, at least 50%, at least 100%, at least 200%, at least 500%, at least 1000% or more lower than the expression level of the gene in the reference sample.

Some CSC-associated genes that are normally produced in very low quantities but whose production is dramatically increased in tumor cells, e.g., a CSC-associated gene in Table 1 or 8, can trigger an immune response. Thus, in some instances, specific immunoreactivity against a CSC-associated polypeptide, e.g., a polypeptide encoded by a gene listed in Table 1 or 8, in a individual may be diagnostic of cancer in the individual. Immunoreactivity against CSC-associated polypeptides may be humoral or cellular, and is associated with a specific immune response to a CSC-associated polypeptide that is upregulated in a cancer stem cell in an individual. In the case of a humoral response the diagnostic methods may involve detecting the presence of one or more antibodies in an individual that specifically bind CSC-associated polypeptides. Methods for detecting antibodies are disclosed herein (e.g., ELISA, peptide arrays, etc.) and are well known in the art. In some cases, the presence of CSC-polypeptide specific effector cells is diagnostic of an immune response specific to that CSC-polypeptide.

T Lymphocytes recognize complexes of peptide ligands (e.g., CSC-associated polypeptides) and Major Histocompatibility Complex (MHC) molecules presented at the surface of Antigen Presenting Cells (APC). Class I tetramers bind to a distinct set of T cell receptors (TCRs) on a subset of CD8+ T cells, and Class II tetramers bind to a distinct population of CD4+ T cells. Methods for detecting antigen-specific T cells using MHC tetramers are well known in the art (e.g., New Microarray Detects Antigen-Specific T Cells and Immune Responses. PLoS Biol 1(3): e76 2003) and can be used to detect CSC-polypeptide specific T cells which may be diagnostic of cancer in an individual. ITAG reagents, for example, from Beckman Coulter provide a convenient way to measure the cellular response directed toward a single CSC-associated peptide using MHC tetramers.

The methods for evaluating expression of CSC-associated genes, e.g., diagnostic methods, disclosed herein may be combined with methods for treating an individual having or suspected of having cancer. The treatment may comprise a step of determining the expression level of the CSC-associated gene in the individual. The treatment may also comprise a step of comparing the expression level of the CSC-associated gene to a reference value, such that the results of the comparison are diagnostic of cancer in the individual. In certain cases, if the comparison results in a diagnosis of cancer in the individual, the administering step is performed. In some cases, after a diagnosis is made using the methods disclosed herein, a treatment plan is selected. For example, if a diagnostic assay reveals that the expression of a particular CSC-associated gene is altered, e.g., increased or decreased, compared to a normal reference sample, then a treatment directed at that particular CSC-associated gene may be implemented. The diagnostic methods can also be used to evaluate the response to a treatment. For example, the determining and the comparing may be repeated at one or more intervals after the administering step to evaluate the response to the treatment.

CSC-associated polypeptide arrays and arrays of antibodies that bind CSC-associated polypeptides may be constructed by immobilizing large numbers of isolated CSC associated polypeptides or antibodies, or antigen binding fragments, to a solid support. Methods for producing polypeptide and antibody arrays are well known in the art. The methods typically involve production of proteins (CSC-associated polypeptides or antibodies) from an expression library, cloned into E. coli, yeast, or mammalian cells, or similar system, e.g., hybridomas etc., from which the expressed proteins are then purified, for example via His, GST tag, or Protein A/G affinity purification. Cell free protein transcription/translation is an alternative for synthesis of proteins which do not express well in bacterial or other in vivo systems. The purified isolated CSC associated polypeptides or antibodies are immobilized on the array surface (solid support surface) using art known methods. For example, proteins can be immobilized by adsorption, covalent (e.g., aldehydes) and non-covalent (e.g., biotin-streptavidin) interactions. Other methods of conjugation will be readily apparent to one of ordinary skill in the art. In some embodiments, the polypeptide arrays of the invention consist essentially of at least 2, at least 5, at least 10, at least 20, at least 50, at least 100, or more polypeptides or immunogenic fragments thereof encoded by a CSC-associated gene set forth in Table 1, 5, 7, or 8. In some embodiments, the antibody arrays of the invention consist essentially of at least 2, at least 5, at least 10, at least 20, at least 50, at least 100, or more different antibodies or antigen-binding fragments that specifically bind polypeptides (CSC-associated polypeptides) encoded by a CSC-associated gene set forth in Table 1, 5, 7, or 8.

Methods for producing nucleic acid arrays are well known in the art. Nucleic acid arrays may be constructed by, e.g., immobilizing to a solid support large numbers oligonucleotides, polynucleotides, or cDNAs having sequences complementary to CSC-associated mRNAs. The skilled artisan is also referred to Chapter 22 "Nucleic Acid Arrays" of Current Protocols In Molecular Biology (Eds. Ausubel et al. John Wiley and #38; Sons NY, 2000), International Publication WO00/58516, U.S. Pat. Nos. 5,677,195 and 5,445,934 which provide exemplary methods relating to nucleic acid array construction and use in detection of nucleic acids of interest. In some embodiments, the nucleic acid arrays consist essentially of at least 2, at least 5, at least 10, at least 20, at least 50, at least 100, at least 200, at least 300, or more of the CSC-associated genes set forth in Table 1, 5, 7, or 8.

In some embodiments, the expression levels of multiple CSC-associated genes may be combined to produce an expression profile. As used herein, "expression profile" refers to a set of expression levels of a plurality (e.g., 2 or more) of CSC-associated genes. Expression profiles have a variety of uses. For example, expression profiles may be used to classify (or sub-classify) a sample, preferably a clinical sample. In some embodiments, reference samples, for which a classification, e.g., a disease category, e.g., breast cancer, prostate cancer, melanoma, etc., has already been ascertained, are used to produce known expression profiles. In some embodiments, the similarity of an expression profile of a test sample and a known expression profile, is assessed by comparing the level of the same CSC-associated gene in the test and known expression profiles (i.e., expression level pairs). In some cases, a test expression profile is compared with one or more members of a plurality of known expression profiles, and a known expression profile that most closely resembles (i.e., is most similar to) the test profile is identified. In certain cases, the classification of a known expression profile that is identified as similar to a test expression profile is assigned to the test expression profile, thereby classifying the clinical sample associated with the test expression profile. The methods are useful for classifying samples across a range of phenotypes, e.g., disease status, risk status, etc., based on expression profiles. In some embodiments, a classification model (e.g., discriminant function, naïve bayes, support vector machine, logistic regression, and others known in the art) may be built based on the reference expression profiles from various samples from individuals known to have different disorders (e.g., cancers) and/or from healthy individuals, and used to classify subsequently obtained samples (e.g., clinical samples).

The invention also provides methods for stratifying a population comprising individuals having cancer. In some embodiments, methods involve determining expression levels of at least 2, at least 5, at least 10, at least 20, at least 50, at least 100, at least 200, at least 300, or more of the CSC-associated genes set forth in Table 5, 7, or 8, for example, by using the arrays of the invention, and stratifying the population based on the expression levels. The stratification methods are useful in epidemiological studies, for example, to identify subpopulations of individuals at risk of cancer. The methods are also useful in clinical studies to identify patient subpopulations that respond better or worse to a particular treatment.

In some aspects, CSC-associated genes provide a basis for identifying, isolating, cloning, propagating, and expanding CSC populations in vitro. The present invention contemplates any suitable method of employing agents, e.g., isolated peptides, e.g., antibodies, that bind to CSC-associated polypeptides to separate CSCs from other cells. Accordingly, included in the present invention is a method of producing a population of isolated CSCs. The methods involve contacting a sample, e.g., a cell suspension, with one or a combination of agents, e.g., antibodies or antigen binding fragments or ligands, which recognize and bind to an epitope, e.g., a cell surface protein, including CSC-associated polypeptides (e.g., polypeptides encoded by the genes listed in Table 4), on the CSC and separating and recovering from the sample the cells bound by the agents. The CSC-associated polypeptide may be encoded by a CSC-associated gene that is selected from the group consisting of: ANK2, NCKAP1L, PTPRE, PTPRS, SBF1, SCN3A, SGCA, SGCB, SLC2A11, SLC2A8, SLC4A1, STX3, and TBC1D8.

In some instances, commerically available antibodies or antibody fragments that bind CSC-associated polypeptides may be used in the methods disclosed herein. For example, antibodies against ANK2 include, e.g., rabbit anti-human Ankyrin brain polyclonal antibody from Abcam; mouse anti-human ANK2 monoclonal antibody clone 2.2 from Genway Biotech, Inc.; and mouse anti-human Ankyrin, brain variant 2 (ANK2) monoclonal, clone 2.20 and rabbit anti-human ankyrin, brain variant 2 (ank2) polyclonal from Lifespan Biosciences. Antibodies against NCKAP1L include, e.g., rabbit anti-human HEM1 polyclonal antibody from Proteintech Group, Inc. and are described in Weiner O D, et al., (2006) Hem-1 Complexes Are Essential for Rac Activation, Actin Polymerization, and Myosin Regulation during Neutrophil Chemotaxis. PLoS Biol 4(2): e38. Antibodies against PTPRE include, e.g., rabbit anti-PTPepsilon C-term RB0551-0552 polyclonal antibody from Abgent, mouse anti-human PTPRE polyclonal antibody from Abnova Corporation; mouse anti-PTPRE monoclonal antibody Clone 2D10 from Abnova Corporation; chicken anti-human PTPRE polyclonal antibody from Thermo Scientific; and Rabbit Anti-Protein Tyrosine phosphatase epsilon (PTPRE) antibody from Acris Antibodies GmbH. Antibodies against PTPRS include, e.g., mouse anti-PTPRS monoclonal antibody from Abcam; mouse anti-human PTPRS monoclonal antibody Clone 1H6 from Abnova Corporation; chicken anti-human PTPRS polyclonal antibody from ABR-Affinity Bioreagents, now sold as Thermo Scientific; chicken anti-human PTPRS polyclonal antibody from GeneTex; and mouse anti-human PTPRS monoclonal antibody, Clone 1H6 from GeneTex. Antibodies against SCN3A include, e.g., rabbit anti-SCN3A polyclonal antibody from Abcam; mouse anti-human SCN3A monoclonal antibody Clone 3F3 from Abnova Corporation; and mouse Anti-human SCN3A monoclonal antibody Clone 3F3 from GeneTex. Antibodies against SCNB include, e.g., mouse anti-beta Sarcoglycan Monoclonal Antibody from Abcam; mouse anti-human SGCB monoclonal antibody Clone 1C10 from Abnova Corporation; mouse anti-human SGCB monoclonal antibody Clone 1C10 from GeneTex; and rabbit anti-human Beta-sarcoglycan (SGCB) Polyclonal from Lifespan Biosciences. Antibodies against SLC2A8 include, e.g., rabbit anti-human Glucose Transporter 8 Polyclonal Antibody from Abcam; goat anti-GLUT8/SLC2A8 polyclonal antibody from Everest Biotech; rabbit anti-GLUCOSE TRANSPORTER 8 Polyclonal Antibody from GenWay Biotech, Inc.; rabbit Anti-Human GLUCOSE TRANSPORTER 5, C Terminus Polyclonal Antibody from GenWay Biotech, Inc.; goat anti-SLC2A8 polyclonal antibody from IMGENEX; and rabbit anti-Human Solute Carrier Family 2 (Facilitated Glucose Transporter) Member 8 (Slc2a8) polyclonal from Lifespan Biosciences. Antibodies against SBF1 include, e.g., rabbit Anti-MTMR5 C-term RB0717 polyclonal antibody from Abgent. Antibodies against SGCA include, e.g., mouse Anti-SGCA monoclonal antibody Clone 3C4 from Abnova Corporation; rabbit Anti-Human SGCA polyclonal antibody from Atlas Antibodies; mouse Anti-SGCA monoclonal antibody clone 3C4 from Novus Biologicals; rabbit Anti-Human SGCA PRESTIGE ANTIBODIES from Sigma-Aldrich. Antibodies against SLC2A11 include, e.g., rabbit anti-human Solute Carrier Family 2 (Facilitated Glucose Transporter), Member 11 (Slc2a11) polyclonal from Lifespan Biosciences. Antibodies against SLC4A1 include, e.g., rabbit anti-human Band 3, N Terminus polyclonal antibody from Abcam; mouse anti-human SLC4A1 Max-Pab® polyclonal antibody from Abnova Corporation; rabbit anti-human SLC4A1 polyclonal antibody from Aviva Systems Biology; mouse anti-Band 3 Monoclonal Antibody Clone BIII 136 from GenWay Biotech, Inc.; and mouse anti-human Solute Carrier Family 4, Anion Exchanger, Member 1 (SLC4A1) monoclonal Clone 3 h3 from Lifespan Biosciences. Antibodies against STX3 include, e.g., rabbit anti-human STX3 Polyclonal Antibody from Atlas Antibodies and rabbit anti-human STX3 from Sigma-Aldrich. Antibodies against TBC1D8 include, e.g., mouse anti-human TBC1D8 monoclonal antibody Clone 1A12 from Abnova Corporation; mouse anti-human TBC1D8 monoclonal antibody Clone 1A12 from GeneTex; mouse anti-human TBC1D8 monoclonal antibody Clone SS-18 from Santa Cruz Biotechnology, Inc.; and rabbit anti-human TBC1D8, aa 132-231 polyclonal antibody from Strategic Diagnostics, Inc.

Agents may be linked to a solid-phase and utilized to capture CSCs from a sample. The bound cells may then be separated from the solid phase by known methods depending on the nature of the agent, e.g., antibody, and solid phase. Alternatively, the agents may be conjugated to a detectable label, e.g., a fluorophore, that can be utilized to separate cells in a liquid phase, such as by fluorescent activated cell sorting. Exemplary fluorophores are well known in the art (e.g., Invitrogen's MOLECULAR PROBES technologies) and include FITC, TRITC, Cy3, Cy5, Alexa Fluorescent Dyes, and Quantum Dots.

Systems appropriate for preparing the desired cell population include magnetic bead/paramagnetic particle column utilizing isolated peptides that bind CSC-associated polypeptides for either positive or negative selection; separation based on biotin or streptavidin affinity; and high speed flow cytometric sorting of immunofluorescent-stained CSCs mixed in a suspension of other cells. Thus, the methods of the present invention include the isolation of a population of CSCs.

Isolated CSCs may be prepared as substantially pure preparations. The term "substantially pure" means that a preparation is substantially free of other cells. For example, an isolated CSC should constitute at least 70 percent of the total cells present with greater percentages, e.g., at least 85, 90, 95 or 99 percent, being preferred. The cells may be packaged in a finished container such as a cryovial along with any other components that may be desired, e.g., agents for preserving cells, or reducing bacterial growth. The CSCs are useful for a variety of purposes. The isolated cells may be used in basic research setting and in screening assays to identify compounds or compositions that affect growth of CSCs.

Isolated CSCs, prepared according to the methods disclosed herein, may be useful in a drug discovery context for lead compound identification and optimization in cell-based screens. For example, the effect of a compound on the growth and/or survival of a CSC may be determined in a cell-based screen that uses an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Other exemplary assays include BrdU, EdU, or H3-Thymidine incorporation assays; DNA content assays using a nucleic acid dye, such as Hoechst Dye, DAPI, Actinomycin D, 7-aminoactinomycin D or Propidium Iodide; Cellular metabolism assays such as AlamarBlue, MTT, XTT, and CellTitre Glo; Nuclear Fragmentation Assays; Cytoplasmic Histone Associated DNA Fragmentation Assay; PARP Cleavage Assay; TUNEL staining; and Annexin staining.

In some aspects, the agents for isolating CSCs are antibody or antigen-binding fragments. The antibodies and antigen binding fragments of the invention include monoclonal antibodies, polyclonal antibodies, human antibodies, chimeric antibodies, humanized antibodies, single-chain antibodies, $F(ab')_2$, Fab, Fd, Fv, or single-chain Fv fragments.

Other aspects of the invention relate to treatment methods. In some embodiments, the methods involve modulating, e.g., inducing or inhibiting, the activity of CSC-associated genes (RNA or protein) and, thereby, inhibiting the growth and survival of cancer stem cells. In some embodiments, the treatment methods involve selective delivery, e.g., by antibodies or antigen-binding fragments, of therapeutic agents to cancer stem cells. The methods are useful for inhibiting the proliferation and/or survival of cancer stem cells and, therefore, are useful for treating cancer, e.g., melanoma. The level of modulation, e.g., inducing or inhibiting, of the activity of a CSC-associated gene that is sufficient to affect the growth and/or survival of a cancer stem cell compared with a control level depends on a variety of factors, including the particular CSC-associated gene being modulated, the cancer stem cell within which the modulation occurs, and the level of expression in the control sample. It is well within the purview of the skilled artisan to determine the appropriate level of modulation that is sufficient to sufficient to inhibit the growth and/or survival of a cancer stem cell.

The term "inhibiting" refers to any decrease in expression level or activity. As used herein, "inhibit", "suppress", or "reduce" may, or may not, be complete. For example, cell proliferation, may, or may not, be decreased to a state of complete arrest for an effect to be considered one of suppression, inhibition or reduction of cell proliferation. Moreover, "suppress", "inhibit", or "reduce" may comprise the maintenance of an existing state and the process of effecting a change in state. For example, inhibition of cell proliferation may refer to the prevention of proliferation of a non-proliferating cell (maintenance of a non-proliferating state) and the process of inhibiting the proliferation of a proliferating cell (process of affecting a proliferation state change). Similarly, inhibition of cell survival may refer to killing of a cell, or cells, such as by necrosis or apoptosis, and the process of rendering a cell susceptible to death, such as by inhibiting the expression or activity of an anti-apoptotic regulatory factor. The suppression, inhibition, or reduction may be at least about 5%, 10%, 15%, 20%, 25%, 30%, 35%, 40%, 45%, 50%, 55%, 60%, 65%, 70%, 75%, 80%, 85%, 90%, 95%, 99% of control level (e.g., an untreated state). In some cases, the level of modulation (e.g., suppression, inhibition, or reduction) compared with a control level is statistically significant. "Statistically signficant" is a term well known in the art and, for example, may refer to a p-value of less than 0.05, e.g., a p-value of less than 0.025 or a p-value of less than 0.01, using an appropriate statistical test (e.g., ANOVA, MANOVA, t-test, multiple comparison test, etc.).

The methods involve treating an individual having, or at risk of having, cancer. As used herein an "individual at risk of having cancer" is an individual, e.g., a human, with an increased likelihood of having cancer compared with a control population, e.g., a general population. Any one of a number of risk factors known in the art may be evaluated to determine whether or not an individual is at risk of having cancer. For example, factors that render an individual at risk of having melanoma include, for example, UV exposure, family history of melanoma, personal history of melanoma, fair skin, freckles, high numbers of nevi (moles), light hair, age, gender, and Xeroderma pigmento sum.

The treatment methods disclosed herein may involve administering a therapeutically effective amount of a composition that induces the expression of a CSC-associated gene which is downregulated in cancer (e.g., a gene in Table 2 or 7). In some instances, the composition that induces expression of a CSC-associated gene comprises a vector, such as an isolated plasmid, that expresses the CSC-associated gene.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes or portions thereof.

An expression vector is one into which a desired sequence may be inserted, e.g., by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, hosts, colonies or plaques (e.g., green fluorescent protein).

Methods for identifying and obtaining coding sequences for use in the methods disclosed herein are routine in the art. For example, the skilled artisan may search Entrez Gene database using a GeneID or GeneAlias of a CSC-associated gene, e.g., a GeneID listed in Table 5, 7 or 8, to identify transcripts associated with CSC-associated genes. In most cases, links to commercial suppliers (e.g., Open Biosystems) of cDNA's containing the transcripts are provided in the Entrez Gene webinterface, which can be utilized to procure a copy cDNA clone. In other cases, commerical sources (e.g., Sigma Aldrich) can be contacted directly.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. It will be appreciated that a coding sequence need not encode a protein but may instead, for example, encode a functional RNA such as an shRNA.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art. One of skill in the art will be aware of appropriate regulatory sequences for expression of interfering RNA, e.g., shRNA, miRNA, etc.

In some embodiments, a virus vector for delivering a nucleic acid molecule, an isolated plasmid, is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220-227, 1996; Eloit et al., *J. Virol.* 7:5375-5381, 1997; Chengalvala et al., *Vaccine* 15:335-339, 1997), a modified retrovirus (Townsend et al., *J. Virol.* 71:3365-3374, 1997), a nonreplicating retrovirus (Irwin et al., *J. Virol.* 68:5036-5044, 1994), a replication defective Semliki Forest virus (Zhao et al., *Proc. Natl. Acad. Sci. USA* 92:3009-3013, 1995), canarypox virus and highly attenuated vaccinia virus derivative (Paoletti, *Proc. Natl. Acad. Sci. USA* 93:11349-11353, 1996), non-replicative vaccinia virus (Moss, *Proc. Natl. Acad. Sci. USA* 93:11341-11348, 1996), replicative vaccinia virus (Moss, *Dev. Biol. Stand.* 82:55-63, 1994), Venzuelan equine encephalitis virus (Davis et al., *J. Virol.* 70:3781-3787, 1996), Sindbis virus (Pugachev et al., *Virology* 212:587-594, 1995), lentiviral vectors (Naldini L, et al., *Proc Natl Acad Sci USA.* 1996 Oct. 15; 93(21):11382-8) and Ty virus-like particle (Allsopp et al., *Eur. J. Immunol* 26:1951-1959, 1996).

Another virus useful for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other useful viral vectors are based on non-cytopathic eukaryotic viruses in which non-essential genes have been replaced with the gene of interest. Non-cytopathic viruses include certain retroviruses, the life cycle of which involves reverse transcription of genomic viral RNA into DNA with subsequent proviral integration into host cellular DNA. In general, the retroviruses are replication-deficient (i.e., capable of directing synthesis of the desired transcripts, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991).

In some embodiments, isolated plasmid vectors comprises a tumor-specific, e.g., melanoma-specific, e.g., a tyrosinase promoter, operably linked to the CSC-associated gene (See, e.g., Lillehammer, T. et al., Cancer Gene Therapy (2005) 12, 864-872). Other exemplary tumor-specific promoters are known in the art and will be apparent to the skilled artisan.

The treatment methods may involve administering a therapeutically effective amount of a composition that targets a product of a CSC-associated gene (i.e., Table 1), which are CSC-associated genes that upregulated in cancer stem cells. The composition may target a product of a CSC-associated gene selected from the group set forth in Table 4, which are upregulated in cancer stem cells and are associated with the cell surface.

The product, e.g., mRNA or protein, of a CSC-associated gene can be targeted by any one of a number of methods known in the art. For example, the composition may comprise a gene knockdown reagent, e.g., siRNA, that is complementary to a CSC-associated mRNA and inhibits its expression. In other embodiments, the composition may comprise an isolated molecule, e.g., antibody or antigen binding fragment, that is conjugated to a siRNA and that specifically binds to a CSC-associated polypeptide. Such antibody conjugated siRNAs (or similar gene suppression agents) may target a CSC-associated mRNA such as any of those encoded by the genes set forth in Table 1.

The CSC-associated gene may be selected from the following group ANK2, NCKAP1L, PTPRE, PTPRS, SBF1, SCN3A, SGCA, SGCB, SLC2A11, SLC2A8, SLC4A1, STX3, and TBC1D8 which are upregulated in cancer stem cells and associated with the cell surface. The siRNA may target another gene in the cell that is useful for inhibiting the growth and/or survival of the cell, for example an oncogene. For example, oncogenes that may be targeted include FOS, JUN, MYB, RAS, and ABL. Other exemplary oncogenes are well known in the art and several such examples are described in, for example. The Genetic Basis of Human Cancer (Vogelstein, B. and Kinzler, K. W. eds. McGraw-Hill, New York. N. Y., 1998). Other upregulated genes include Epidermal growth factor (beta-urogastrone, HOMG4/URG); Heparanase (HPA/HPR1); Jagged 1 (Alagille syndrome, AGS/AHD); Platelet/endothelial cell adhesion molecule (CD31 antigen, CD31/PECAM-1); Transforming growth factor, alpha (TFGA); and Vascular endothelial growth factor C (Flt4-L/VRP). Homologues of such genes can also be used.

Various strategies for gene knockdown known in the art can be used to inhibit gene expression (e.g., expression of CSC-associated genes). For example, gene knockdown strategies may be used that make use of RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. In one embodiment, vector-based RNAi modalities (e.g., shRNA or shRNA-mir expression constructs) are used to reduce expression of a gene (e.g., a CSC-associated) in a cell. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a tumor-specific, e.g., melanoma-specific, promoter operably linked to a gene encoding the small interfering nucleic acid, e.g., an shRNA. In some cases, the isolated plasmid vector is packaged in a virus capable of infecting the individual. Exemplary viruses include adenovirus, retrovirus, lentivirus, adeno-associated virus, and others that are known in the art and disclosed herein.

A broad range of RNAi-based modalities could be employed to inhibit expression of a gene in a cell, such as siRNA-based oligonucleotides and/or altered siRNA-based oligonucleotides. Altered siRNA based oligonucleotides are those modified to alter potency, target affinity, safety profile and/or stability, for example, to render them resistant or partially resistant to intracellular degradation. Modifications, such as phosphorothioates, for example, can be made to oligonucleotides to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluyl nucleotides maintain gene silencing activity (Xia et al., ASC Chem. Biol. 1(3): 176-83, (2006)). siRNAs with amide-linked oligoribonucleosides have been generated that are more resistant to S1 nuclease degradation than unmodified siRNAs (Iwase R et al. 2006 Nucleic Acids Symp Ser 50: 175-176). In addition, modification of siRNAs at the 2'-sugar position and phosphodiester linkage confers improved serum stability without loss of efficacy (Choung et al., Biochem. Biophys. Res. Commun. 342(3):919-26, 2006). Other molecules that can be used to inhibit expression of a gene (e.g., a CSC-associated gene) include sense and antisense nucleic acids (single or double stranded), ribozymes, peptides, DNAzymes, peptide nucleic acids (PNAs), triple helix forming oligonucleotides, antibodies, and aptamers and modified form(s) thereof directed to sequences in gene(s), RNA transcripts, or proteins. Antisense and ribozyme suppression strategies have led to the reversal of a tumor phenotype by reducing expression of a gene product or by cleaving a mutant transcript at the site of the mutation (Carter and Lemoine Br. J. Cancer. 67(5):869-76, 1993; Lange et al., Leukemia. 6(11):1786-94, 1993; Valera et al., J. Biol. Chem. 269(46):28543-6, 1994; Dosaka-Akita et al., Am. J. Clin. Pathol. 102(5):660-4, 1994; Feng et al., Cancer Res. 55(10): 2024-8, 1995; Quattrone et al., Cancer Res. 55(1):90-5, 1995; Lewin et al., Nat Med. 4(8):967-71, 1998). Ribozymes have also been proposed as a means of both inhibiting gene expression of a mutant gene and of correcting the mutant by targeted trans-splicing (Sullenger and Cech Nature 371(6498):619-22, 1994; Jones et al., Nat. Med. 2(6):643-8, 1996). Ribozyme activity may be augmented by the use of, for example, non-specific nucleic acid binding proteins or facilitator oligonucleotides (Herschlag et al., Embo J. 13(12):2913-24, 1994; Jankowsky and Schwenzer Nucleic Acids Res. 24(3):423-9, 1996). Multitarget ribozymes (connected or shotgun) have been suggested as a means of improving efficiency of ribozymes for gene suppression (Ohkawa et al., Nucleic Acids Symp Ser. (29):121-2, 1993).

Triple helix approaches have also been investigated for sequence-specific gene suppression. Triple helix forming oligonucleotides have been found in some cases to bind in a sequence-specific manner (Postel et al., Proc. Natl. Acad. Sci. U.S.A. 88(18):8227-31, 1991; Duval-Valentin et al., Proc. Natl. Acad. Sci. U.S.A. 89(2):504-8, 1992; Hardenbol and Van Dyke Proc. Natl. Acad. Sci. U.S.A. 93(7):2811-6, 1996; Porumb et al., Cancer Res. 56(3):515-22, 1996). Similarly, peptide nucleic acids have been shown to inhibit gene expression (Hanvey et al., Antisense Res. Dev. 1(4): 307-17, 1991; Knudsen and Nielson Nucleic Acids Res. 24(3):494-500, 1996; Taylor et al., Arch. Surg. 132(11): 1177-83, 1997). Minor-groove binding polyamides can bind in a sequence-specific manner to DNA targets and hence may represent useful small molecules for suppression at the DNA level (Trauger et al., Chem. Biol. 3(5):369-77, 1996). In addition, suppression has been obtained by interference at the protein level using dominant negative mutant peptides and antibodies (Herskowitz Nature 329(6136):219-22, 1987; Rimsky et al., Nature 341(6241):453-6, 1989; Wright et al., Proc. Natl. Acad. Sci. U.S.A. 86(9):3199-203, 1989). In some cases suppression strategies have led to a reduction in RNA levels without a concomitant reduction in proteins, whereas in others, reductions in RNA have been mirrored by reductions in protein. The diverse array of suppression strategies that can be employed includes the use of DNA and/or RNA aptamers that can be selected to target a protein of interest (e.g, a CSC-associated polypeptide).

Methods of delivering a therapeutic agent to a cancer stem cell are also provided. The methods involve a step of contacting a cancer stem cell with an isolated molecule that selectively binds to a cell surface polypeptide encoded by a CSC-associated gene, such as those selected from the group set forth in Table 4. The CSC-associated gene may be selected from the group consisting of: ANK2, NCKAP1L, PTPRE, PTPRS, SBF1, SCN3A, SGCA, SGCB, SLC2A11, SLC2A8, SLC4A1, STX3, and TBC1D8. The cancer stem cell may be in vivo or in vitro. Isolated molecules that bind to CSC-associated polypeptides on the surface of a cancer stem cell may be taken up into an intracellular compartment of the cancer stem cell.

Cancer stem cells include stem cells of a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cancer, e.g., renal cell carcinoma, a hepatocellular carcinoma, a bile duct carcinoma, a choriocarcinoma, a seminoma, a embryonal carcinoma, a Wilms' tumor, or a testicular tumor. In specific embodiments, the cancer stem cells are stem cells of melanoma. Cancer stem cells include $ABCB5^+$ cells and $ABCB5^-$ cells. Stem cells of other cancers will be known to one of ordinary skill in the art.

The treatment methods of the invention involve administering compositions that comprise isolated molecules, or combinations of different isolated molecules, that specifically bind to CSC-associated polypeptides (polypeptides encoded by the CSC-associated gene) to treat cancer, e.g., melanoma, in an individual. When the CSC-associated polypeptide is associated with the extracellular surface of a cell, e.g., a cancer stem cell, e.g., a melanoma stem cell, the isolated molecule can bind the CSC-associated polypeptide and, for example, serve as an vehicle for specifically targeting therapeutic agents (therapeutic molecules) to the cell. In some embodiments, isolated molecules that binds to a CSC-associated polypeptide on the surface of a cell are taken up into an intracellular compartment of the cell bind to a secreted molecule, such as a growth factor that may assist the tumor (such as those listed in Table 1.2). The isolated molecules that interact with unregulated proteins may be used alone as therapeutics or in combination with other therapeutics.

As used herein treatment of or treating cancer includes preventing the development of a cancer, reducing the symptoms of a cancer and/or inhibiting, slowing the growth of or preventing further growth of an existing cancer. Treatment may include amelioration, cure, and/or maintenance of a cure (i.e., prevention or delay of relapse) of a disorder, e.g., cancer. Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse).

Cancers include for instance a colon carcinoma, a pancreatic cancer, a breast cancer, an ovarian cancer, a prostate cancer, a squamous cell carcinoma, a cervical cancer, a lung carcinoma, a small cell lung carcinoma, a bladder carcinoma, a squamous cell carcinoma, a basal cell carcinoma, an adenocarcinoma, a sweat gland carcinoma, a sebaceous gland carcinoma, a papillary carcinoma, a papillary adenocarcinoma, a cystadenocarcinoma, a medullary carcinoma, a bronchogenic carcinoma, a renal cell carcinoma, a hepatocellular carcinoma, a bile duct carcinoma, a choriocarcinoma, a seminoma, an embryonal carcinoma, a Wilms' tumor, or a testicular tumor. In certain embodiments, the cancer is melanoma.

The invention, in some aspects, relates to an isolated molecule that selectively binds to a polypeptide encoded by a CSC-associated gene set forth in Table 4 and that is conjugated to a therapeutic agent. In some instances, the CSC-associated gene is selected from the group consisting of: ANK2, NCKAP1L, PTPRE, PTPRS, SBF1, SCN3A, SGCA, SGCB, SLC2A11, SLC2A8, SLC4A1, STX3, and TBC1D8. Compositions comprising the foregoing isolated molecules are also disclosed.

As used herein an "isolated molecule" is a molecule such as a polypeptide, nucleic acid, polysaccharide, drug, nucleoprotein, lipoprotein, glycoprotein, steroid, and lipid that is isolated from its natural environment or produced synthetically. In some embodiments, the isolated molecule is a ligand of a CSC-associated polypeptide. In other embodiments, the isolated molecule is an antibody or antigen-binding fragment. As disclosed herein, antibody or antigen-binding fragments include monoclonal antibodies, polyclonal antibodies, human antibodies, chimeric antibodies, humanized antibodies, single-chain antibodies, F(ab')$_2$, Fab, Fd, Fv, or single-chain Fv fragments. In some embodiments, an isolated molecule may have therapeutic utility alone and need not be conjugated to a therapeutic agent. For example, an isolated molecule may bind to a cell surface receptor that is a CSC-associated polypeptide and function as an antagonist or competitive inhibitor of the receptor (e.g., to inhibit a signaling pathway).

In some embodiments, isolated molecules are conjugated to therapeutic agents. As used herein, a "therapeutic agent" is a molecule such as a polypeptide, nucleic acid, polysaccharide, drug, nucleoprotein, lipoprotein, glycoprotein, steroid, and lipid that is capable of altering the state of a cell (e.g., killing a cell, inhibiting growth of a cell) for therapeutic purposes. A therapeutic agent may be, for instance, a toxin, a small-interfering nucleic acid, or a chemotherapeutic agent. Alternatively the therapeutic may be administered in conjunction with the molecule. In conjunction refers to delivery to the same subject. The actual administration may be at the same or a different time or in the same or a different delivery vehicle.

Toxins include for example, radioisotopes such as $^{225}$Ac, $^{211}$At, $^{212}$Bi, $^{213}$Bi, $^{186}$Rh, $^{188}$Rh, $^{177}$Lu, $^{90}$Y, $^{131}$I, $^{67}$Cu, $^{125}$I, $^{123}$I, $^{77}$Br, $^{153}$Sm, $^{166}$Bo, $^{64}$Cu, $^{212}$Pb, $^{224}$Ra and $^{223}$Ra, and others known in the art. Suitable chemical toxins include members of the enediyne family of molecules, such as calicheamicin and esperamicin as well as poisonous lectins, plant toxins such as ricin, abrin, modeccin, botulina and diphtheria toxins. Of course, combinations of the various toxins could also be coupled to one isolated molecule, e.g., an antibody, thereby accommodating variable cytotoxicity. The coupling of one or more toxin molecules to the isolated molecule, e.g., antibody, is envisioned to include many chemical mechanisms, for instance covalent binding, affinity binding, intercalation, coordinate binding, and complexation.

Chemotherapeutic agents include the following compounds or classes of compounds: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Buniodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorombucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Ifesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin;

Mitomycin, Mitosper; Mitotane; Mitoxantrone Hydrochloride; Mycophenolic Acid; Nocodazole; Nogalamycin; Ormaplatin; Oxisuran; Paclitaxel Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate, Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid, 2-chloro-2'-arabino-fluoro-2'-deoxyadenosine; 2-chloro-2'-deoxyadenosine; anisomycin; trichostatin A; hPRL-G129R; CEP-751; linomide; Piritrexim Isethionate; Sitogluside; Tamsulosin Hydrochloride and Pentomone.

The invention, in some aspects, provides kits comprising one or more containers housing one or more of the compositions of the invention. The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. The kits may also include reference samples. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a individual. The kit may include a container housing agents described herein. The agents may be in the form of a liquid, gel or solid (powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to an animal, such as a syringe, topical application devices, or iv needle tubing and bag, particularly in the case of the kits for treating individuals with cancer.

The compositions and therapeutic agents may be administered simultaneously or sequentially. When the other therapeutic agents are administered simultaneously they can be administered in the same or separate formulations, but are administered at the same time. The other therapeutic agents are administered sequentially with one another and with the modulators, when the administration of the other therapeutic agents and the modulators is temporally separated. The separation in time between the administration of these compounds may be a matter of minutes or it may be longer.

The compositions of the present invention preferably contain a pharmaceutically acceptable carrier or excipient suitable for rendering the compound or mixture administrable orally as a tablet, capsule or pill, or parenterally, intravenously, intradermally, intramuscularly or subcutaneously, or transdermally. The active ingredients may be admixed or compounded with any conventional, pharmaceutically acceptable carrier or excipient. The compositions may be sterile.

As used herein, the term "pharmaceutically acceptable carrier" includes any and all solvents, dispersion media, coatings, antibacterial and antifungal agents, isotonic agents, absorption delaying agents, and the like. The use of such media and agents for pharmaceutically active substances is well known in the art. Except insofar as any conventional media or agent is incompatible with the compositions of this invention, its use in the therapeutic formulation is contemplated. Supplementary active ingredients can also be incorporated into the pharmaceutical formulations. A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art.

It will be understood by those skilled in the art that any mode of administration, vehicle or carrier conventionally employed and which is inert with respect to the active agent may be utilized for preparing and administering the pharmaceutical compositions of the present invention. Illustrative of such methods, vehicles and carriers are those described, for example, in Remington's Pharmaceutical Sciences, 18th ed. (1990), the disclosure of which is incorporated herein by reference. Those skilled in the art, having been exposed to the principles of the invention, will experience no difficulty in determining suitable and appropriate vehicles, excipients and carriers or in compounding the active ingredients therewith to form the pharmaceutical compositions of the invention.

An effective amount, also referred to as a therapeutically effective amount is an amount sufficient to ameliorate at least one adverse effect associated with expression, or reduced expression, of a CSC-associated gene in a cell or in an individual in need of such inhibition or supplementation. The therapeutically effective amount to be included in pharmaceutical compositions depends, in each case, upon several factors, e.g., the type, size and condition of the patient to be treated, the intended mode of administration, the capacity of the patient to incorporate the intended dosage form, etc. Generally, an amount of active agent is included in each dosage form to provide from about 0.1 to about 250 mg/kg, and preferably from about 0.1 to about 100 mg/kg. One of ordinary skill in the art would be able to determine empirically an appropriate therapeutically effective amount.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the particular individual. The effective amount for any particular application can vary depending on such factors as the disease or condition being treated, the particular therapeutic agent being administered, the size of the individual, or the severity of the disease or condition. One of ordinary skill in the art can empirically determine the effective amount of a particular nucleic acid and/or other therapeutic agent without necessitating undue experimentation.

The pharmaceutical compositions can be administered by any suitable route for administering medications. A variety of administration routes are available. The particular mode selected will depend, of course, upon the particular agent or agents selected, the particular condition being treated, and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are discussed herein. For use in therapy, an effective amount of the nucleic acid and/or other therapeutic agent can be administered to an individual by any mode that delivers the agent to the desired surface, e.g., mucosal, systemic.

Administering the pharmaceutical composition of the present invention may be accomplished by any means known to the skilled artisan. Routes of administration include but are not limited to oral, parenteral, intravenous, intramuscular, intraperitoneal, intranasal, sublingual, intratracheal, inhalation, subcutaneous, ocular, vaginal, and rectal. Systemic routes include oral and parenteral. Several types of devices are regularly used for administration by inhalation. These types of devices include metered dose inhalers (MDI), breath-actuated MDI, dry powder inhaler (DPI), spacer/holding chambers in combination with MDI, and nebulizers.

In some cases, compounds of the invention are prepared in a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vesicles (LUVs), which range in size from 0.2-4.0 μm can encapsulate large macromolecules. RNA, DNA and intact virions can be encapsulated within the aqueous interior and be delivered to cells in a biologically active form. Fraley et al. (1981) Trends Biochem Sci 6:77.

Liposomes may be targeted to a particular tissue by coupling the liposome to a specific binding molecule such as one that binds to a CSC-associated polypeptide. Binding molecules which may be useful for targeting a liposome to, for example, a cancer stem cell include, but are not limited to intact or fragments of molecules, e.g., antibodies or antigen binding fragments, which interact with CSC-associated polypeptides on the surface of cancer stem cells. Such binding molecules may easily be identified by binding assays well known to those of skill in the art.

Lipid formulations for transfection are commercially available from QIAGEN, for example, as EFFECTENE™ (a non-liposomal lipid with a special DNA condensing enhancer) and SUPERFECT™ (a novel acting dendrimeric technology).

Liposomes are commercially available from Gibco BRL, for example, as LIPOFECTIN™ and LIPOFECTACE™, which are formed of cationic lipids such as N-[1-(2,3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis G (1985) Trends Biotechnol 3:235-241.

Certain cationic lipids, including in particular N-[1-(2,3 dioleoyloxy)-propyl]-N,N,N-trimethylammonium methylsulfate (DOTAP), appear to be especially advantageous when combined with the modified oligonucleotide analogs of the invention.

In one embodiment, the vehicle is a biocompatible microparticle or implant that is suitable for implantation or administration to the mammalian recipient. Exemplary bioerodible implants that are useful in accordance with this method are described in PCT International application no. PCT/US/03307 (Publication No. WO95/24929, entitled "Polymeric Gene Delivery System". PCT/US/0307 describes a biocompatible, preferably biodegradable polymeric matrix for containing an exogenous gene under the control of an appropriate promoter. The polymeric matrix can be used to achieve sustained release of the therapeutic agent in the individual.

The polymeric matrix preferably is in the form of a microparticle such as a microsphere (e.g., wherein a therapeutic agent is dispersed throughout a solid polymeric matrix) or a microcapsule (e.g., wherein a therapeutic agent is stored in the core of a polymeric shell). Other forms of the polymeric matrix for containing the therapeutic agent include films, coatings, gels, implants, and stents. The size and composition of the polymeric matrix device is selected to result in favorable release kinetics in the tissue into which the matrix is introduced. The size of the polymeric matrix further is selected according to the method of delivery which is to be used, typically injection into a tissue or administration of a suspension by aerosol into the nasal and/or pulmonary areas. Preferably when an aerosol route is used the polymeric matrix and the therapeutic agent are encompassed in a surfactant vehicle. The polymeric matrix composition can be selected to have both favorable degradation rates and also to be formed of a material which is bioadhesive, to further increase the effectiveness of transfer when the matrix is administered to a nasal and/or pulmonary surface that has sustained an injury. The matrix composition also can be selected not to degrade, but rather, to release by diffusion over an extended period of time. Biocompatible microspheres that are suitable for delivery, such as oral or mucosal delivery, are disclosed in Chickering et al. (1996) Biotech Bioeng 52:96-101 and Mathiowitz E et al. (1997) Nature 386:410-414 and PCT Pat. Application WO97/03702.

Both non-biodegradable and biodegradable polymeric matrices can be used to deliver the therapeutic agentsto an individual. Biodegradable matrices are preferred. Such polymers may be natural or synthetic polymers. The polymer is selected based on the period of time over which release is desired, generally in the order of a few hours to a year or longer. Typically, release over a period ranging from between a few hours and three to twelve months is most desirable, particularly for the nucleic acid agents. The polymer optionally is in the form of a hydrogel that can absorb up to about 90% of its weight in water and further, optionally is cross-linked with multi-valent ions or other polymers.

Bioadhesive polymers of particular interest include bioerodible hydrogels described by H. S. Sawhney, C. P. Pathak and J. A. Hubell in Macromolecules, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

If the therapeutic agent is a nucleic acid, the use of compaction agents may also be desirable. Compaction agents also can be used alone, or in combination with, a biological or chemical/physical vector. A "compaction agent", as used herein, refers to an agent, such as a histone, that neutralizes the negative charges on the nucleic acid and thereby permits compaction of the nucleic acid into a fine granule. Compaction of the nucleic acid facilitates the uptake of the nucleic acid by the target cell. The compaction agents can be used alone, i.e., to deliver a nucleic acid in a form that is more efficiently taken up by the cell or, more preferably, in combination with one or more of the above-described vectors.

Other exemplary compositions that can be used to facilitate uptake of a nucleic acid include calcium phosphate and other chemical mediators of intracellular transport, microinjection compositions, electroporation and homologous recombination compositions (e.g., for integrating a nucleic acid into a preselected location within the target cell chromosome).

The compounds may be administered alone (e.g., in saline or buffer) or using any delivery vehicle known in the art. For instance the following delivery vehicles have been described: cochleates; Emulsomes; ISCOMs; liposomes; live bacterial vectors (e.g., *Salmonella, Escherichia coli, Bacillus* Calmette-Guérin, *Shigella, Lactobacillus*); live viral vectors (e.g., Vaccinia, adenovirus, Herpes Simplex); microspheres; nucleic acid vaccines; polymers (e.g. carboxymethylcellulose, chitosan); polymer rings; proteosomes; sodium fluoride; transgenic plants; virosomes; and, virus-like particles.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by an individual to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long-acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R (1990) Science 249:1527-1533, which is incorporated herein by reference.

The compounds may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product. Liquid dose units are vials or ampoules. Solid dose units are tablets, capsules and suppositories.

Other delivery systems can include time-release, delayed release or sustained release delivery systems. Such systems can avoid repeated administrations of the compounds, increasing convenience to the individual and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

EXAMPLES

Among the numerous CSC-associated genes are genes involved in vasculogenesis and angiogenesis. For example, global gene expression analyses validated by mRNA and protein determinations revealed preferential display of genes for vascular endothelial growth factor receptor-1 (VEGFR-1) and related members of signaling cascades involved in vasculogenesis and angiogenesis in ABCB5$^+$ MMIC. In vitro, vascular endothelial growth factor (VEGF) induced expression of the endothelial-associated marker CD144 (VE-cadherin) in VEGFR-1-expressing ABCB5$^+$ MMIC but not VEGFR-1-negative ABCB5$^-$ melanoma bulk populations, indicating a unique capacity of CSC for VEGF/VEGFR-1 signaling-dependent vasculogenic differentiation. In vivo, tumors initiated from patient-derived melanoma cells or established melanoma cultures by xenotransplantation into the murine subcutis or by intradermal injection into human skin in chimeric murine recipients formed perfused ABCB5 mRNA- and protein-expressing vessel-like channels also detected in clinical melanoma specimens that co-expressed CD144 and the vasculogenic mimicry marker TIE-1[4]. Tumour initiation in human skin by fluorescent transgene-expressing human melanoma cells confirmed CD144$^+$ channels to be of melanoma origin. Moreover, MMIC depletion in tumour grafts to human skin significantly reduced channel formation and resulted in attenuated tumour growth. Our results identify melanoma vasculogenesis driven by ABCB5+ MMIC as a novel mechanism by which CSC may promote tumor growth. Furthermore, they suggest that MMIC-dependent vasculogenesis represents a novel CSC target for VEGF/VEGFR-1-directed inhibitors of angiogenesis.

Example 1 Materials and Methods

Melanoma Cells and Culture Methods.

The established human cutaneous melanoma cell lines G3361, A375, MALME-3M, SK-MEL-2, SK-MEL-5, SK-MEL-28, UACC-62, UACC-257, M14 and MDA-MB-435 were cultured as described[3,5,23]. Clinical cutaneous melanoma cells were derived from surgical specimen according to human subjects research protocols approved by the IRBs of the University of Würzburg Medical School or the Wistar Institute, Philadelphia, Pa. as described previously[3]. The established human uveal melanoma cell lines MUM-2B and MUM-2C were a gift of Dr. Mary J. Hendrix, Northwestern University, and were cultured as described[16].

Cell Isolation.

ABCB5+-purified (ABCB5+) cells were isolated by positive selection and ABCB5+-depleted (ABCB5−) cell populations were generated by removing ABCB5+ cells using anti-ABCB5 mAb (clone 3C2-1D12[23]) labeling and magnetic bead cell sorting as described[3]. Briefly, human G3361, A375, MUM-2B or MUM-2C melanoma cells or single cell suspensions derived from clinical melanoma samples were labeled with anti-ABCB5 mAb for 30 min at 4° C., washed twice for excess antibody removal, followed by incubation with secondary anti-mouse IgG mAb-coated magnetic microbeads for 30 min at 4° C. Subsequently, cells were washed twice for excess magnetic microbead removal and then sorted into ABCB5+ and ABCB5− cell fractions by dual-passage cell separation in MidiMACS or MiniMACS separation columns (depending on cell number) according to the manufacturer's recommendations (Miltenyi Biotec, Auburn, Calif.). Assessment of purity of ABCB5+ and ABCB5− (ABCB5+ cell-depleted) melanoma cell isolates and determination of cell viability following magnetic cell sorting were performed and yielded similar results as described previously[3].

Global Gene Expression Microarray Analyses.

Microarray analyses were performed on purified ABCB5+ (n=5) and ABCB5− (n=5) cell subsets derived from the established human melanoma cell lines G3361 and A375 and from three distinct clinical melanoma specimen previously characterized in our laboratory with regards to ABCB5 expression and MMIC phenotype in human melanoma xenotransplantation assays[3]. Total RNA was extracted, processed and hybridized as described previously[10] onto Affymetrix human HG-U133Plus2 GeneChip microarrays (Affymetrix, Santa Clara, Calif.). Statistical analysis of microarray results was performed as described previously[10]. The expression data set in its entirety will be made available through GEO (gene expression omnibus). Functional gene networks were generated using Ingenuity Pathways Analysis (Ingenuity® Systems, ingenuity.com), by mapping each gene identifier to its corresponding gene object in the Ingenuity Pathways Knowledge Base. These focus genes were overlaid onto a global molecular network developed from information contained in the Ingenuity Pathways Knowledge Base. Focus gene networks were then algorithmically generated based on their connectivity and subsequently analyzed to identify the biological functions that were most significant to the genes in the network.

RNA Extraction and Reverse Transcriptase-PCR.

Total RNA was isolated from ABCB5+ and ABCB5− human melanoma cells using RNeasy columns (QIAGEN, Valencia, Calif.). Standard cDNA synthesis reactions were performed using 5 μg RNA and the SuperScript First-Strand Synthesis System for reverse transcriptase-PCR (Invitrogen, Carlsbad, Calif.) as per the manufacturer's instructions. For PCR analysis, 5 μl of diluted first strand product (~100 ng of cDNA) was added to 45 μl of PCR reaction mixture containing 5 units of Superscript II (Invitrogen) according to the manufacturer's protocol. The following PCR program was performed: denaturation at 95° C. for 5 min, then cycled 35 times at 94° C. for 1 min, 53° C. for 30 s, and 72° C. for 30 s, and subsequently extended at 72° C. for 10 min. The primer sequences were as follows: PTK2 forward primer, 5'-TGCCTTTTACTTTCGTGTGG-3'(SEQ ID NO:1); PTK2 reverse primer 5'-CCAAATTCCTGTTTTGCTTCA-3'(SEQ ID NO:2); MET forward primer 5'-CCCCACCT-TATCCTGACGTA-3'(SEQ ID NO:3); MET reverse primer 5'-CGTGTGTCCACCTCATCATC-3'(SEQ ID NO:4); NRP2 forward primer 5'-GAGGCAGGG-GAAAATAGAGG-3'(SEQ ID NO:5); NRP2 reverse primer 5'-TCTCCCGAAAGGTTGAAATG-3'(SEQ ID NO:6); ETS1 forward primer 5'-CGCTTACTCTGTTGGGGTCT-3' (SEQ ID NO:7); ETS1 reverse primer 5'-TCTCCAGCAAAATGATGTGC-3'(SEQ ID NO:8); FLT1 forward primer 5'-TGGCAACTGCTTT-TATGTTCTG-3'(SEQ ID NO:9); FLT1 reverse primer 5'-TCCATAGGGTGATGGTCAAA-3'(SEQ ID NO: 10). The reaction products were resolved on a 1% LE agarose gel (Ambion, Austin, Tex.) and photographed. β-Actin primers were used as controls to ensure RNA integrity.

RNA Extraction and Real Time Quantitative PCR.

Total RNA was isolated from unsegregated or sorted human melanoma cells using the RT² qPCR Grade RNA isolation kit (SABiosciences, Frederick, Md.). Standard cDNA synthesis reactions were performed using 1 μg RNA and the RT² First Strand Kit for reverse transcriptase-PCR (SABiosciences) as per the manufacturer's instructions. The reverse transcriptase product (1 μl) was amplified by primer pairs specific for ABCB5[5]. β-actin was used as a normalizing control. The primers for ABCB5 (Genebank accession no. AY234788) detection were 5'-GCTGAGGAATCCACC-CAATCT-3' (forward) (SEQ ID NO:11) and 5'-AGCCT-GAATGGCCTTTTGTG-3' (reverse) (SEQ ID NO:12). The primers for β-actin detection were 5'-CCTGGCACCCAGCACAAT-3' (SEQ ID NO:13) (forward) and 5'-AGTACTCCGTGTGGATCGGC-3' (reverse) (SEQ ID NO: 14). Samples were assayed using Sybergreen chemistry and kinetic PCR (ABI 7300 Sequence Detector; Applied Biosystems, Foster City, Calif.). Samples were amplified using the Sybergreen PCR reagent kit (Applied Biosystems) according to the manufacturer's protocol. Sense and antisense primers were used at a final concentration of 10 nM. The cDNA samples were amplified under following conditions: 50° C. for 2 min and 95° C. for 10 min, followed by 40 cycles of amplification at 94° C. for 15 s and 60° C. for 1 min. All samples were run in triplicate. The relative amounts of transcripts were analyzed using the 2(−Delta Delta C(T)) method as described previously[3,5,10]. Statistical differences between mRNA expression levels were determined using the nonparametric Mann-Whitney test. A two-sided P value of P<0.05 was considered significant.

Western Analysis.

Total cell lysates were harvested from logarithmically growing cultures of the human melanoma cell lines MALME-3M, SK-MEL-2, SK-MEL-5, SK-MEL-28, UACC-62, UACC-257, M14, and MDA-MB-435 and analyzed by 8% SDS-PAGE and Western assay to detect relative levels of ABCB5 (mAb 3C2-1D12[23]) and alpha-tubulin (mAb clone DM1A, Sigma-Aldrich, St. Louis, Mo.), using LI-COR Odyssey IR imaging system densitometry.

Flow Cytometry.

G3361, A375, MUM-2B, or MUM-2C melanoma cells were analyzed for surface ABCB5 expression by incubation with anti-ABCB5 mAb or isotype control mAb for 30 min at 4° C., followed by counterstaining with FITC-conjugated goat anti-mouse Ig or with APC-conjugated donkey anti-mouse IgG secondary Abs and single color flow cytometry at the Fl1 (FITC) or F14 (APC) emission spectrum on a Becton Dickinson FACScan as described[3,5,23]. Washing was performed twice between each step. Analysis of coexpression of ABCB5 with the VEGFR-1 surface marker in G3361 melanoma cells was performed by dual-color flow cytometry as described[3]. Briefly, melanoma cells were incubated for 30 min at 4° C. with anti-ABCB5 mAb or isotype control mAb, followed by counterstaining with APC-conjugated donkey anti-mouse IgG secondary Ab as above. Subsequently, cells were fixed at 4° C. and then incubated for 30 min at 4° C. with PE-conjugated anti-VEGFR-1 mAb (R&D Systems, Minneapolis, Minn.) or PE-conjugated isotype control mAb (BD PharMingen, San Diego, Calif.). Dual color flow cytometry was subsequently performed with acquisition of fluorescence emission at the F14 (APC) and F12 (PE) spectra on a Becton Dickinson FACScan. Washing was performed twice between each step. Statistical differences between expression levels of markers were determined using the nonparametric Mann-Whitney test. A two-sided P value of P<0.05 was considered significant.

In Vitro Vasculogenic Differentiation and Tube Formation Assays.

VEGF-dependent induction of CD144 expression and formation of capillary-like tube structures by human G3361 melanoma cells was assayed on growth factor reduced Matrigel, a basement membrane matrix preparation (BD Biosciences, San Jose, Calif.). Growth factor reduced Matrigel was added to eight-chamber polystyrene vessel tissue culture-treated glass slides and allowed to gelatinize for 20 min at 37° C. Purified ABCB5+ or ABCB5- or unsegregated human melanoma cells were seeded into culture slide wells at densities of $5 \times 10^4$ cells/cm$^2$ in medium 199 containing 5% FCS[11] in the presence or absence of VEGF (100 ng/ml). After 48-hour incubation, cells were fixed with 4% paraformaldehyde/PBS for 20 min at room temperature, and after extensive washing with PBS the cells were blocked in 5% donkey serum/0.01% Tween 20/PBS for 1 hr at room temperature. Cells were then incubated with rabbit anti-CD144 polyclonal Ab (diluted 1:100; Bethyl Laboratories, Montgomery, Tex.) overnight at 4° C. After extensive washing with 0.01% Tween 20/PBS, the cells were incubated with goat anti-rabbit Texas red-conjugated secondary Ab (diluted 1:250; Jackson ImmunoResearch Laboratories, West Grove, Pa.) for 1 hr at room temperature. Following washing with 1×PBS/0.01% Tween 20, cells were then mounted in Vectashield (Vecta Laboratories, Burlingame, Calif.) supplemented with 100 ng/ml DAPI to visualize nuclei. Cells were analyzed by fluorescent microscopy using a Mercury-100 Watts fluorescent light source (Microvideo Instruments, Avon, Mass.) attached to a Nikon Eclipse TE 300 microscope (Nikon Instruments, Melville, N.Y.) with the use of separate filters for each fluorochrome. The images were obtained using a Spot digital camera (Diagnostic Instruments Inc., Sterling Heights, Mich.), and the Spot 3.3.2. software package was imported into Adobe Photoshop (Adobe Systems, Mountain View, Calif.). For tube formation assays, unsegregated human melanoma cells were seeded into culture slide wells at densities of $5 \times 10^4$ cells/cm$^2$ in medium 199 containing 5% FCS[11]. Immediately, cells were pretreated with medium alone, rabbit anti-VEGFR1 Ab (10 µg/ml; Santa Cruz Biotechnology, Santa Cruz, Calif.) or rabbit isotype control Ab (10 µg/ml; BD Biosciences) at 37° C. for 2 hrs prior to stimulation with VEGF (100 ng/ml). Tube formation was detected by phase contrast microscope (Nikon Eclipse TE 300 microscope) after 24 hrs of incubation. For quantitative analysis of tube formation and length and for determination of CD144 expression at 48 hrs, n=3 three randomly selected microscopy fields were photographed per experimental condition. Images were acquired as described above and tube formation was analyzed using Image J software available from the National Institutes of Health web site as described previously[24]. For quantification of CD144 expression, positive cells were counted using Neurolucida 8.10 software (MBF Bioscience, Williston, Vt.). Differences among groups were analyzed by one-way ANOVA followed by Bonferroni post hoc tests. Differences with P values<0.05 were considered statistically significant.

In Vitro Adipogenic, Osteogenic and Myogenic Differentiation Assays.

For adipogenic, osteogenic and myogenic differentiation assays purified ABCB5+ and ABCB5- G3361 melanoma cells were seeded in triplicate at $3 \times 10^3$ cells/well in 96-well culture plates. Adipogenic and osteogenic differentiation was assessed using commercially available differentiation kits and Oil Red O and Alizarin Red staining, respectively, according to the manufacturer's instructions (Chemicon International, Temecula, Calif.). Myogenic differentiation assays were performed as described previously[10]. Briefly, melanoma subpopulations were incubated in growth medium consisting of DMEM with 4% glucose, 20% fetal bovine serum (vol/vol), 1% (vol/vol) penicillin-streptomycin (10,000 UI/ml-10,000 µg/ml, Invitrogen) for 10 days. The medium was exchanged every 2 days. At day 14, cells were fixed in ice cold methanol for 3 min on ice and incubated with 1:50 diluted anti-myogenin mouse monoclonal Ab (Dako, Carpinteria, Calif.) overnight at 4° C. Plates were then washed, incubated with goat anti-mouse FITC-conjugated secondary Ab (Jackson ImmunoResearch Laboratories, diluted 1:100) and then mounted with Vectashield mounting medium (Vector) supplemented with 100 ng/ml DAPI to visualize nuclei. Slides were visualized with the 20× and 40× objective on a Nikon Eclipse TE2000-S microscope, photographed using the Spot 7.4 slider camera and images processed using Spot software version 4.0.9. (Diagnostic Instruments, Sterling Heights, Mich.). For quantification of differentiation marker expression, positive cells were manually counted and statistical differences between expression levels of markers were determined using the nonparametric Mann-Whitney test. A two-sided P value of P<0.05 was considered significant.

Immunohistochemistry and Immunofluorescence Double Labeling.

The following primary Abs were used: rat anti-Laminin B2, (Abcam, Cambridge, Mass.), rabbit anti-CD144, (Cell Signaling, Beverly, Mass.), goat anti-Tie-1, (Neuromics, Edina, Minn.), and mouse anti-ABCB5[3,5,23]. Isotype matched irrelevant Abs served as negative control. The secondary Abs were horse anti-mouse IgG-HRP, horse anti-goat IgG-HRP, goat anti-rabbit IgG-HRP (VECTOR Laboratories, Burlingame, Calif.) and goat anti-rat IgG-HRP (Biolegend, San Diego, Calif.), and donkey anti-mouse IgG-AF488, donkey anti-rabbit IgG-AF594, and donkey anti-goat IgG-AF594 (Invitrogen, Carlsbad, Calif.). Immunohistochemistry was performed using the 2-step horseradish peroxidase method. Briefly, frozen tissue sections were fixed with −20° C. acetone for 5 min, then incubated with primary Ab at 4° C. overnight. After washing out unbound primary Ab with phosphate-buffered saline (PBS), the tissue sections were incubated with secondary Ab at room temperature for 30 min, then washed with PBS 3×5 min. Immunoreactivity was detected using NovaRed peroxidase substrate (VECTOR Laboratories, Burlingame, Calif.). For immunofluorescence double labeling, the frozen tissue sections were fixed with −20° C. acetone for 5 min, then incubated with the mix of 2 primary Abs (for example ABCB5 Ab+CD144 Ab) at 40° C. overnight. After washing with PBS, the tissue sections were incubated with the mix of 2 secondary Abs (for example donkey anti-mouse IgG-AF488+ donkey anti-rabbit IgG-AF594) at room temperature for 1 hour, then washed with PBS 3×5 min, and the sections were then mounted with ProLong Gold antifade reagent with DAPI (Invitrogen, Carlsbad, Calif.). The sections were viewed under a Olympus BX51 System fluorescence microscope (Olympus Corporation, Tokyo, Japan). For HLA-2A immunohistochemistry of SK-MEL-5 melanoma xenografts to chimeric mouse/human skin, frozen sections were incubated with 5 μg/ml mouse anti-human HLA-2A Ab (BD Pharmingen, San Jose, Calif.) at 4° C. overnight. After washing out unbound primary Ab with phosphate buffered saline (PBS), sections were incubated with 1:200 peroxidase-conjugated horse anti-mouse IgG Ab (Vector Laboratories, Burlingame, Calif.) at room temperature for 30 min. Unbound secondary Ab was washed out with PBS. Color was developed using the NovRed peroxidase substrate kit (Vector Laboratories) and sections were counterstained with hematoxylin Gill's No. 1 (Fisher Scientific, Pittsburgh, Pa.).

In Situ Hybridization.

RNA probes were prepared as follows: PCR-derived RNA probe templates were synthesized by introducing the T7 promoter into the antisense strand and the SP6 promoter into the sense strand. The primer pair, AB5T7AS (5'-TAATACGACTCACTATAGG-GATGTCTGGCTTTTTCCCTTCTTGAC-3') (SEQ ID NO:15) and AB5SP6S (5'-GATTTAGGTGACAC-TATAGAAATTCAAGCTGGACGAATGACCCCA-3') (SEQ ID NO:16), was used to generate the DNA template for antisense and sense RNA probes spanning 200 base pairs of human ABCB5 cDNA. This sequence encodes ABCB5 amino acids 499-564 (GI:34539755). The primer pair CD133T7AS (5'-TAATACGACTCACTATAGG-GAGCAGCCCCAGGACACAGCATA-3') (SEQ ID NO:17) and CD133SP6S (5'-GATTTAGGTGACAC-TATAGAGACCCAAGACTCCCATAAAGC-3') (SEQ ID NO:18) was used to generate the DNA template for antisense and sense RNA probes spanning 200 base pairs of human CD133 cDNA, wherein this sequence encodes CD133 amino acid 42-108 (GI: 5174386). The sequence specificities for ABCB5 and CD133 were confirmed using the Genbank database BLAST program. The RNA probes were labeled with digoxigenin (DIG) using the DIG RNA labeling kit (Roche Applied Science, Indianapolis, Ind.). For in situ hybridization, 8 μM frozen tissue sections were baked at 50° C. for 15 min, then fixed in 4% paraformaldehyde at room temperature (RT) for 20 min. The sections were treated with 1 μg/ml proteinase K/PBS at 37° C. for 20 min and inactivated proteinase K with 0.2% glucine/PBS at RT for 5 min. Upon washes with PBS 2×2 min, the tissue sections were fixed in 4% paraformadehyde at RT for 15 min, washed with PBS 2×5 min, and then treated with 0.25% acetic anhydride/0.1M triethanolamine at RT for 10 min. The tissue sections were placed in 2×SSC and then hybridized with 500 ng/ml antisense or sense probe in hybridization buffer (0.3M NaCl, 10 mM Tris-HCl pH 7.6, 5 mM EDTA, 1× Denharts, 50% formamide, 100 μg/ml tRNA and 10% dectran sulphate) at 42° C. overnight. Post hybridization sections were treated with 0.2×SSC at 55° C. for 2×20 min, 20 □g/ml RNaseA in 0.5M NaCl, 10 mM Tris-HCl pH 7.5 at 37° C. for 30 min, and 0.2×SSC at 55° C. for 20 min. The hybridized probes were immunodetected using the DIG detection kit (Roche) and the Tyramide Signal Amplification (TSA) kit (PerkinElmer, Boston, Mass.) as follows: 1×DIG block buffer for 30 min, 1:100 anti-DIG Ab peroxidase conjugate at RT for 1 hour, 1×DIG wash 3×5 min, TSA reagent 10 min at RT, PBS 2×5 min, 1:100 streptavidin-horseradish peroxidase 30 min at RT, PBS 3×5 min. The labeling was visualized with NovaRed substrate (Vector Laboratories).

Animals.

BALB/c nude mice and NOD/SCID mice were purchased from The Jackson Laboratory (Bar Harbor, Me.). SCID mice (C.B-17) and BALB/c Rag2$^{-/-}$ mice were purchased from Taconic (Germantown, N.Y.). The animals were housed in autoclaved microisolator cages and were fed sterilized food and water. Mice were maintained in accordance with the institutional guidelines of Children's Hospital Boston and Harvard Medical School and experiments were performed according to approved experimental protocols.

Human to Mouse Melanoma Xenotransplantation and Human to Chimeric Mouse/Human Skin Melanoma Xenotransplantation.

Human to mouse melanoma xenografts were established by subcutaneous injection of human G3361, A375, SK-MEL-5 or clinical patient-derived human melanoma cells in BALB/c nude or NOD/SCID mice as described previously[3]. For human to chimeric mouse/human skin melanoma xenotransplantation, single donor-derived split human skin was obtained in accordance with the Partners HealthCare Research Management Institutional Review Board by cutting abdominal skin with a 0.016-inch gauge dermatome. Human skin was subsequently xenografted onto immunodeficient Rag2$^{-/-}$ mice as described previously[13], under a protocol approved by the institutional animal committee. Briefly, two circular graft beds, each, 1.5 cm$^2$ were prepared on bilateral dorsa of 4-8 week old Rag2$^{-/-}$ micetreated with antibiotics (1 tablet of additional food per week containing Amoxicillin (3 mg), Flagyl (0.69 mg) and Bismuth (0.185 mg)) to prevent *Helicobacter pylorii* infection. Human donor skin was trimmed to conform to the bed and held in place with staples until 10 days following surgery. Unsegregated or ABCB5$^+$-depleted A375, MUM-2B or MUM-2C melanoma cells (2×10$^6$ in 20 μl PBS) were intradermally microinjected into grafts after 6 weeks stabilization. All skin grafts were harvested in their entirety 3 weeks after tumour cell inoculation, fixed in formalin, serially sectioned and stained with H&E using standard methods for histological analysis of tumour formation. Sections representing maximum cross-sectional tumour area and thus best approximating the size of the generally spherical to ovoid tumour nodules were evaluated. Tumour volume (TV) was histologically determined and calculated as described[3]. Statistically significant differences in histological tumour formation were assessed using the Fisher's Exact test. Differences in tumour volume were statistically compared using the nonparametric Mann-Whitney Test, with a two-sided P value of P<0.05 considered significant.

Stable Green Fluorescence Protein (GFP)-Transfected Melanoma Xenografts to Human-SCID Chimeras.

Recombinant lentiviral vectors harboring GFP cDNA were obtained from Dr. M. Herlyn at the Wistar Institute and used to infect human A375 melanoma cells by lentiviral gene transfer. Two days after infection, cells were selected with puromycin (1 µg/ml) for a period of 7 days. Transgene expression was verified by fluorescence microscopy and flow cytometry. Melanoma xenografts were generated in human-SCID chimeras according to the protocol previously described[13]. SCID mice (C.B-17) between 4-6 weeks of age were purchased from Taconic (Germantown, N.Y.). Mice were anesthetized and prepared for transplantation by shaving the hair from a 2 cm$^2$ area on the dorsal torso followed by removal of full thickness skin down to the fascia. Full thickness human foreskin grafts of the same size were placed onto the wound beds. The skin grafts were then covered by Vaseline-saturated gauze and secured with band aids and 3M sports tapes. After 10 days, the dressings were removed and the mice allowed to recover for approximately 4-5 weeks before melanoma inoculation. GFP-labeled A375 melanoma cells were harvested and suspended in PBS at a density of 10$^8$ cells/ml. One hundred µl each of cell suspension were injected intradermally into the human skin grafts. The tumour xenografts were then harvested in 3 weeks or when the tumour reaches 1 cm$^3$ in size, and processed for frozen section. For double immunofluorescence, frozen sections (5 µm thick) of melanoma xenografts were fixed in 4% paraformaldehyde, blocked with donkey serum, and incubated sequentially with anti-CD144 (Cell Signaling, Danvers, Mass.), Texas red-conjugated donkey anti-rabbit (Invitrogen, Carlsbad, Calif.), anti-GFP (Novus Biologicals, Littleton, Colo.), and FITC-conjugated donkey anti-goat Abs (Jackson ImmunoResearch, West Grove, Pa.). After washing in PBS, the sections were coverslipped using an antiquench mountant containing DAPI (VectaShield, Vector Laboratories, Burlingame, Calif.). Irrelevant isotype-matched primary Abs were included as controls.

Example 2

The mechanisms through which ABCB5$^+$ MMIC or CSC in other cancers trigger and promote neoplastic progression are currently unknown. We hypothesized that ABCB5$^+$ MMIC possess vasculogenic differentiation plasticity and selectively drive melanoma growth through a specific role in providing nutritional support to growing tumours based on preferential co-expression in vivo of the vasculogenic differentiation markers CD144 (VE-cadherin) and TIE-1[3] by the ABCB5$^+$ tumourigenic minority population.

To further characterize the repertoire of genes differentially expressed in MMIC compared to tumour bulk populations, we first performed microarray analyses on purified ABCB5$^+$ (n=5) and ABCB5$^-$ (n=5) cell subsets derived from the established human melanoma cell lines G3361 and A375 and from three separate patient-derived melanoma specimens, all previously characterized in our laboratory with regard to ABCB5 expression and MMIC phenotype in human melanoma xenotransplantation assays[3]. Using this approach[10], 399 genes were identified that were differentially expressed (P<0.05) between ABCB5$^+$ MMIC and ABCB5$^-$ melanoma bulk populations (Table 5), in addition to ABCB5 shown overexpressed in ABCB5$^+$ purified populations by real-time PCR (P<0.05). One identified functional gene network, validated by PCR-based gene expression analyses in ABCB5$^+$ melanoma cell subsets, showed key molecules of vasculogenesis (the ability to differentiate along endothelial lines), FLT1 (VEGFR-1) and PTK2 (FAK), and of angiogenesis (the ability to induce ingrowth and proliferation of mature stromal blood vessels), FLT1 (VEGFR-1), PTK2 (FAK), MET (HGFR), NRP2, and ETS1, to be specifically overexpressed in ABCB5$^+$ MMIC (FIG. 1$a$,$b$).

Another set of genes differentially expressed in ABCB+ melanoma stem cells vs. ABCB5-melanoma bulk population cells was identified using RT-PCR. The data is shown in Table 6. The fold-expression levels are shown in the 7$^{th}$ column and can be compared to the control values shown in the last few rows of the table. A positive value indicates that the gene had higher expression levels in ABCB5+ cells and a negative value indicates that the gene had higher expression levels in ABCB5– cells. Some of the genes exhibited a greater than 100-fold and some even greater 1000-fold increase in expression in ABCB5+ versus ABCB5– cells. The highly expressed genes include factors that are likely secreted by the stem cells which may act on cells in a tumor either in an autocrine fashion on tumor stem cells, or in a paracrine fashion also on bulk population cancer cells. Appropriate therapies can be designed to treat cancers by inhibiting the expression or activity of such factors.

Preferential expression of VEGFR-1 by ABCB5$^+$ MMIC vs. ABCB5$^-$ subpopulations was also demonstrated by dual-color flow cytometry at the protein level (15.6±5.3% vs. 4.4±2.0% of cells, respectively, mean±s.e.m., n=6, P<0.05) (FIG. 1$c$). To determine whether VEGF/VEGFR-1 interaction in MMIC influenced expression of the vasculogenic differentiation marker CD144, we evaluated functionally the effects of VEGF signaling in purified ABCB5$^+$ MMIC or ABCB5$^-$ melanoma subpopulations. VEGF (100 ng/ml$^{11}$) selectively induced expression of CD144 at high levels in VEGFR-1-expressing ABCB5$^+$ but not VEGFR-1-negative ABCB5$^-$ melanoma cells, to 36.2±5.7% vs. 4.8±2.7% of cells (mean±s.e.m., n=3), respectively (P<0.01) (FIG. 1$d$). Preincubation with a blocking monoclonal antibody (mAb) to VEGFR-1 abrogated the ability of VEGF to induce CD144 expression in human melanoma cells (0.0±0.0% in VEGFR-1 mAb-treated vs. 64±1% or 57±3% in untreated or isotype control mAb-treated cultures, respectively, mean±s.e.m., n=3, P<0.01) (FIG. 1$e$). Moreover, VEGFR-1 mAb strongly inhibited VEGF-induced multicellular capillary-like tube formation by human melanoma cells in established in vitro vasculogenic differentiation assays[11], with significantly reduced numbers of tubes formed/microscopy field (6.7±0.9 in VEGFR-1 mAb-treated vs. 99.0±24.0 or 76.7±3.3% in untreated or isotype control mAb-treated cultures, respectively, mean±s.e.m., n=3, P<0.05), and significantly lower average tube length (33.2±4.5 µm in VEGFR-1 mAb-treated vs. 92.1±1.6 µm or 86.5±1.7 µm in untreated or isotype control mAb-treated cultures, respectively, mean±s.e.m., n=3, P<0.001) (FIG. 1$f$). In contrast, both ABCB5$^+$ MMIC and ABCB5$^-$ melanoma bulk population exhibited similar adipogenic and osteogenic differentiation capacity previously detected in human melanoma cells[12] (adipogenesis: 100.0±0.0% vs. 93.2±6.9% of cells Oil Red-positive, respectively; mean±s.e.m., n=3, NS; osteogenesis: 90.8±9.2% vs. 98.3±1.7% of cells Alizarin Red-positive, respectively; mean±s.e.m., n=3, NS) (FIG. 1$g$,$h$), and neither ABCB5$^+$ MMIC nor ABCB5$^-$ melanoma bulk population exhibited capacity for myogenic differentiation[10] (0.0±0.0% vs. 0.0±0.0% of cells myogenin-positive, respectively; mean±s.e.m., n=3, NS) (FIG. 1$h$). The selective in vitro vasculogenic differentiation capacity of ABCB5+ MMIC in response to VEGF/VEGFR-1 signaling indicated a potential role of this CSC subset in tumour vasculogenesis.

TABLE 5

Differentially expressed genes between ABCB5+ MMIC and ABCB5− melanoma bulk populations (P < 0.05).

| Molecules | ID | Fold Change |
|---|---|---|
| AABHD7 | 239579_at | 0.661 |
| ACBD6 | 225317_at | 0.83 |
| AK3 | 224655_at | 0.845 |
| AKAP9 | 215483_at | 2.168 |
| AKR1CL2 | 1559982_s_at | 1.732 |
| AMZ2 | 227567_at | 1.377 |
| ANAPC5 | 235926_at | 2.631 |
| ANK2 | 202921_s_at | 4.162 |
| ANKH | 229176_at | 0.776 |
| ANKRD28 | 241063_at | 2.297 |
| ANKRD44 | 226641_at | 1.218 |
| ANKRD52 | 228257_at | 0.762 |
| ANXA4 | 201302_at | 0.83 |
| AOC3 | 204894_s_at | 1.894 |
| APBB2 | 40148_at | 1.139 |
| ARS2 | 201679_at | 1.307 |
| ASCC3L1 (includes EG:23020) | 214982_at | 3.009 |
| ASPM | 232238_at | 1.411 |
| ATAD2 | 235266_at | 1.304 |
| ATP5I | 207335_x_at | 0.737 |
| ATXN2L | 207798_s_at | 1.656 |
| BARD1 | 205345_at | 1.559 |
| BAT3 | 230513_at | 0.697 |
| BCL9L | 227616_at | 1.291 |
| BDP1 | 224227_s_at | 1.632 |
| BLID | 239672_at | 1.91 |
| BRI3 | 223376_s_at | 0.792 |
| BUB1 (includes EG:699) | 216277_at | 1.856 |
| BUB1 (includes EG:699) | 233445_at | 3.209 |
| C10ORF18 | 244165_at | 2.046 |
| C12ORF45 | 226349_at | 0.688 |
| C12ORF48 | 220060_s_at | 1.216 |
| C12ORF51 | 230216_at | 2.874 |
| C12ORF51 | 1557529_at | 3.632 |
| C14ORF135 | 1563259_at | 1.353 |
| C14ORF156 | 221434_s_at | 0.867 |
| C16ORF63 | 225087_at | 0.872 |
| C18ORF10 | 213617_s_at | 0.754 |
| C18ORF10 | 212055_at | 0.737 |
| C19ORF42 | 219097_x_at | 0.813 |
| C20ORF4 | 234654_at | 1.731 |
| C22ORF28 | 200042_at | 0.829 |
| C22ORF30 | 216555_at | 1.521 |
| C2ORF30 | 224630_at | 0.851 |
| C5ORF24 | 229098_s_at | 1.531 |
| C9ORF78 | 218116_at | 0.789 |
| C9ORF85 | 244160_at | 1.52 |
| CABIN1 | 1557581_x_at | 3.052 |
| CAMK2D | 225019_at | 0.823 |
| CAMK2D | 228555_at | 0.758 |
| CANX | 238034_at | 0.8 |
| CAPZB | 201949_x_at | 0.764 |
| CASC5 | 228323_at | 1.144 |
| CBS | 240517_at | 1.818 |
| CCDC127 | 226515_at | 0.835 |
| CCDC14 | 240884_at | 1.771 |
| CCDC52 | 234995_at | 1.166 |
| CCDC57 | 214818_at | 1.703 |
| CCDC73 | 239848_at | 1.294 |
| CCDC93 | 219774_at | 1.208 |
| CDC14B | 234605_at | 2.512 |
| CDC16 | 242359_at | 6.261 |
| CENPJ | 234023_s_at | 1.22 |
| CENPJ | 220885_s_at | 1.64 |
| CEP27 | 228744_at | 0.651 |
| CEP55 | 218542_at | 1.096 |
| CGGBP1 | 224600_at | 0.913 |
| CHD2 | 244443_at | 1.757 |
| CHD8 | 212571_at | 1.27 |
| CLN8 | 229958_at | 1.344 |
| CNIH3 | 232758_s_at | 1.451 |
| COBRA1 | 1556434_at | 1.985 |
| COIL | 203653_s_at | 1.259 |
| COL4A2 | 211966_at | 0.729 |
| COQ4 | 218328_at | 1.328 |
| CPEB2 | 226939_at | 1.251 |
| CPNE3 | 202119_s_at | 0.833 |
| CREB1 | 204313_s_at | 0.791 |
| CREB3L2 | 237952_at | 2.013 |
| CRIPAK | 228318_s_at | 1.486 |
| CROP | 242389_at | 2.121 |
| CSE1L | 201112_s_at | 0.911 |
| CSE1L | 210766_s_at | 0.885 |
| CUL4A | 232466_at | 2.607 |
| CYB5R3 | 1554574_a_at | 0.793 |
| DARS | 201624_at | 0.928 |
| DCLRE1C | 242927_at | 1.187 |
| DCUN1D2 | 240478_at | 1.76 |
| DDX17 | 213998_s_at | 1.528 |
| DDX52 | 212834_at | 0.771 |
| DEGS1 | 209250_at | 0.804 |
| DEPDC1 | 232278_s_at | 1.119 |
| DHX40 | 218277_s_at | 0.812 |
| DNAJC21 | 230893_at | 0.829 |
| DNM1L | 236032_at | 1.503 |
| DTX3 | 49051_g_at | 1.32 |
| ECHDC1 | 233124_s_at | 0.943 |
| EIF2S1 | 201142_at | 0.717 |
| EIF2S1 | 201144_s_at | 0.824 |
| EIF4G3 | 201935_s_at | 1.174 |
| ELOVL2 | 213712_at | 0.699 |
| EMP2 | 225079_at | 0.781 |
| ENAH | 222433_at | 0.783 |
| ENDOD1 | 212573_at | 0.775 |
| ENTPD5 | 231676_s_at | 0.867 |
| ERBB3 | 1563253_s_at | 0.691 |
| ERRFI1 | 224657_at | 0.881 |
| ETS1 | 241435_at | 1.797 |
| EWSR1 | 229966_at | 1.686 |
| EXT1 | 242126_at | 2.116 |
| FAM62C | 239770_at | 1.551 |
| FAM98A | 212333_at | 0.767 |
| FHL3 | 218818_at | 0.546 |
| FLJ10357 | 241627_x_at | 2.31 |
| FLJ31306 | 239432_at | 1.753 |
| FLT1 | 232809_s_at | 1.861 |
| FOXN3 | 218031_s_at | 0.721 |
| FUBP1 | 240307_at | 2.087 |
| GABARAPL2 | 209046_s_at | 0.863 |
| GABPA | 243498_at | 2.03 |
| GALNT1 | 201722_s_at | 0.926 |
| GBF1 | 233114_at | 2.03 |
| GGT1 | 211417_x_at | 1.555 |
| GHITM | 1554510_s_at | 0.764 |
| GMFB | 202544_at | 0.904 |
| GNPDA1 | 202382_s_at | 0.787 |
| GOLGA8A | 213650_at | 2.289 |
| GPD2 | 243598_at | 2.13 |
| GPR107 | 211979_at | 0.843 |
| GPR135 | 241085_at | 1.851 |
| HDAC3 | 240482_at | 2.062 |
| HEATR2 | 241352_at | 0.784 |
| HECW1 | 237295_at | 11.843 |
| HELLS | 242890_at | 1.359 |
| HERC5 | 219863_at | 1.156 |
| HIAT1 | 225222_at | 0.832 |
| HNRNPC | 235500_at | 1.769 |
| HNRPD | 235999_at | 1.92 |
| HNRPD | 241702_at | 1.962 |
| HNRPH1 | 213472_at | 2.332 |
| HOXA2 | 228642_at | 1.44 |
| HOXB9 | 216417_x_at | 0.766 |

TABLE 5-continued

Differentially expressed genes between ABCB5+ MMIC and ABCB5− melanoma bulk populations ($P < 0.05$).

| Molecules | ID | Fold Change |
|---|---|---|
| HOXD3 | 206601_s_at | 1.897 |
| HPS1 | 239382_at | 1.749 |
| HSD17B1 | 228595_at | 0.753 |
| HSDL2 | 209513_s_at | 0.803 |
| HSPA4L | 205543_at | 0.786 |
| HUWE1 | 214673_s_at | 1.858 |
| IDS | 1559136_s_at | 2.001 |
| IFNGR1 | 242903_at | 2.171 |
| IGHMBP2 | 215980_s_at | 0.893 |
| IL13RA1 | 201887_at | 0.775 |
| INSIG2 | 209566_at | 0.872 |
| IPO7 | 200993_at | 0.875 |
| IPW | 213447_at | 1.399 |
| IRS2 | 236338_at | 2.162 |
| JARID1A | 226367_at | 1.192 |
| JARID2 | 232835_at | 2.139 |
| KIAA0841 | 36888_at | 1.389 |
| KIAA0907 | 230028_at | 1.83 |
| KIAA1267 | 224489_at | 1.355 |
| KIAA1618 | 231956_at | 2.27 |
| KIAA1737 | 225623_at | 0.837 |
| KIAA2013 | 1555933_at | 2.18 |
| KIDINS220 | 1557246_at | 2.97 |
| KPNA6 | 226976_at | 0.814 |
| KRTAP19-1 | 1556410_a_at | 2.07 |
| KSR2 | 230551_at | 3.211 |
| LBA1 | 213261_at | 1.225 |
| LIMS1 | 212687_at | 0.822 |
| LOC126917 | 225615_at | 0.819 |
| LOC137886 | 212934_at | 0.886 |
| LOC145757 | 1558649_at | 2.779 |
| LOC145786 | 229178_at | 1.907 |
| LOC146325 | 1553826_a_at | 3.943 |
| LOC203547 | 225556_at | 0.802 |
| LOC219731 | 1557208_at | 0.419 |
| LOC254128 | 1557059_at | 2.164 |
| LOC283888 | 1559443_s_at | 2.56 |
| LOC285147 | 236166_at | 2.377 |
| LOC338799 | 226369_at | 1.137 |
| LOC388135 | 230475_at | 1.979 |
| LOC388969 | 232145_at | 1.555 |
| LOC389203 | 225014_at | 0.79 |
| LOC641298 | 208118_x_at | 1.419 |
| LOC645166 | 228158_at | 0.823 |
| LOC645513 | 239556_at | 2.24 |
| LOC729397 | 236899_at | 2.231 |
| LRCH3 | 229387_at | 1.793 |
| LRRFIP1 | 239379_at | 1.796 |
| MAEA | 207922_s_at | 0.765 |
| MALAT1 | 224568_x_at | 1.699 |
| MALAT1 | 223940_x_at | 1.659 |
| MAP1LC3B | 208785_s_at | 0.808 |
| MAP2K4 | 203266_s_at | 0.881 |
| MAP3K15 | 200979_at | 0.741 |
| 6-Mar | 201737_s_at | 1.219 |
| MBNL1 | 201152_s_at | 0.867 |
| MDM4 | 235589_s_at | 1.629 |
| MECR | 218664_at | 0.832 |
| MED19 | 226300_at | 0.782 |
| MEF2C | 236395_at | 2.104 |
| MET | 213816_s_at | 1.283 |
| MIA3 | 1569057_s_at | 0.759 |
| MLL | 212079_s_at | 1.599 |
| MOBKL1B | 214812_s_at | 0.762 |
| MRPL42 (includes EG:28977) | 217919_s_at | 0.866 |
| MRPL51 | 224334_s_at | 0.846 |
| MTERFD3 | 225341_at | 1.422 |
| MTUS1 | 239576_at | 1.975 |
| MYO10 | 243159_x_at | 2.528 |
| MYO10 | 244350_at | 1.677 |
| N4BP2L1 | 213375_s_at | 2.01 |
| N4BP2L2 | 235547_at | 1.631 |
| N4BP2L2 | 242576_x_at | 2.349 |
| NAALAD2 | 1554506_x_at | 0.464 |
| NANP | 228073_at | 0.817 |
| NAPA | 239362_at | 1.624 |
| NAPE-PLD | 242635_s_at | 1.216 |
| NARG1 | 1556381_at | 2.827 |
| NAT8B | 206964_at | 2.513 |
| NBPF16 | 201104_x_at | 1.411 |
| NBR1 | 1568856_at | 1.957 |
| NCKAP1L | 209734_at | 2.071 |
| NDFIP1 | 217800_s_at | 0.815 |
| NDUFAF2 | 228355_s_at | 0.722 |
| NDUFB6 | 203613_s_at | 0.712 |
| NEK1 | 213328_at | 1.381 |
| NFATC2IP | 217527_s_at | 1.272 |
| NPAS2 | 1557690_x_at | 1.76 |
| NPTN | 228723_at | 2.086 |
| NRP2 | 210841_s_at | 1.106 |
| NUCB2 | 203675_at | 0.812 |
| NUDT4 | 212183_at | 0.685 |
| NUPL1 | 241425_at | 2.179 |
| OCIAD1 | 235537_at | 1.794 |
| ORMDL1 | 223187_s_at | 1.171 |
| OSBPL5 | 233734_s_at | 1.261 |
| OSGEP | 242930_at | 1.541 |
| PABPN1 | 213046_at | 2.228 |
| PAK1 | 226507_at | 0.869 |
| PAPD4 | 222282_at | 3.39 |
| PDE4B | 215671_at | 3.457 |
| PDHB | 211023_at | 0.827 |
| PDHB | 208911_s_at | 0.807 |
| PDK1 | 239798_at | 1.654 |
| PDLIM5 | 212412_at | 0.752 |
| PDSS1 | 236298_at | 1.64 |
| PDXDC1 | 1560014_s_at | 2.105 |
| PGRMC2 | 213227_at | 0.686 |
| PHC1 | 218338_at | 1.123 |
| PHF20L1 | 219606_at | 2.3 |
| PIGY (includes EG:84992) | 224660_at | 0.793 |
| PIP5K3 | 1557719_at | 2.227 |
| PITPNA | 201190_s_at | 0.863 |
| PMP22 | 210139_at | 0.865 |
| PMS2L3 | 214473_x_at | 1.159 |
| POFUT2 | 207448_at | 1.759 |
| POLR2J2 | 1552622_s_at | 1.828 |
| POLR2J2 | 1552621_at | 1.652 |
| POP4 | 202868_s_at | 0.847 |
| PPP1R3D | 204554_at | 0.805 |
| PPP1R7 | 201213_at | 0.698 |
| PPP3CA | 202457_s_at | 0.867 |
| PRO1073 | 228582_x_at | 1.607 |
| PRPF38B | 230270_at | 1.888 |
| PSEN1 | 242875_at | 1.851 |
| PSMA2 | 201316_at | 0.839 |
| PSMA3 | 201532_at | 0.798 |
| PTK2 | 234211_at | 2.539 |
| PTPMT1 | 229535_at | 0.769 |
| RAB11FIP3 | 228613_at | 2.546 |
| RAB11FIP3 | 216043_x_at | 0.551 |
| RAB14 | 200927_s_at | 0.772 |
| RAB1A | 213440_at | 0.81 |
| RAD54L | 204558_at | 1.483 |
| RADIL | 223693_s_at | 2.126 |
| RBM25 | 1557081_at | 1.57 |
| RBM26 | 229433_at | 1.43 |
| RBM4 | 213718_at | 1.53 |
| RBM5 | 209936_at | 2.249 |
| RFT1 | 240281_at | 1.426 |
| RHOA | 240337_at | 2.143 |
| RHOBTB2 | 1556645_s_at | 1.538 |
| RLBP1L1 | 224996_at | 0.835 |
| RNF43 | 228826_at | 1.401 |
| RP11-139H14.4 | 1569124_at | 11.472 |
| RPE | 221770_at | 0.766 |
| RPE | 225039_at | 0.787 |
| RPL7L1 | 225515_s_at | 0.899 |

TABLE 5-continued

Differentially expressed genes between ABCB5+ MMIC and ABCB5− melanoma bulk populations (P < 0.05).

| Molecules | ID | Fold Change |
|---|---|---|
| RUNX3 | 204198_s_at | 1.233 |
| SDAD1 | 242190_at | 3.009 |
| SDCCAG8 | 243963_at | 2.67 |
| SEC16B | 1552880_at | 1.877 |
| SEPHS1 | 208940_at | 0.875 |
| 11-Sep | 201307_at | 0.784 |
| SF1 | 210172_at | 2.452 |
| SF3B1 | 201070_x_at | 1.35 |
| SF3B1 | 214305_s_at | 1.359 |
| SFRS15 | 222311_s_at | 1.818 |
| SFRS15 | 243759_at | 2.028 |
| SGCA | 1562729_at | 2.395 |
| SGOL2 | 235425_at | 1.591 |
| SH2B3 | 203320_at | 0.806 |
| SKP1 | 200718_s_at | 0.898 |
| SLC16A1 | 202235_at | 0.83 |
| SLC20A1 | 230494_at | 1.884 |
| SLC2A11 | 232167_at | 1.529 |
| SLC2A8 | 239426_at | 2.012 |
| SLC30A9 | 237051_at | 2.063 |
| SMA4 | 238446_at | 2.035 |
| SMC6 | 218781_at | 1.203 |
| SMYD2 | 212922_s_at | 0.867 |
| SNORA28 | 241843_at | 1.628 |
| SNRPA1 | 242146_at | 3.54 |
| SON | 201085_s_at | 1.144 |
| SPOPL | 225659_at | 0.828 |
| SQLE | 213577_at | 1.502 |
| SRP72 | 208801_at | 0.751 |
| SRP72 | 208803_s_at | 0.766 |
| SRPRB | 218140_x_at | 0.767 |
| STK36 | 234005_x_at | 1.335 |
| STK36 | 231806_s_at | 1.362 |
| STRAP | 1558002_at | 2.189 |
| STX11 | 235670_at | 0.778 |
| STX8 | 204690_at | 0.819 |
| SUPT7L | 201838_s_at | 0.865 |
| SVIL | 215279_at | 2.228 |
| SYNE2 | 202761_s_at | 1.356 |
| TAF15 | 227891_s_at | 1.971 |
| TAF1B | 239046_at | 1.468 |
| TAOK3 | 220761_s_at | 1.195 |
| TBC1D5 | 201814_at | 0.782 |
| TBC1D8 | 221592_at | 1.246 |
| TBC1D8 | 204526_s_at | 1.373 |
| TBXA2R | 207554_x_at | 0.877 |
| TBXA2R | 336_at | 0.73 |
| TCAG7.907 | 238678_at | 1.546 |
| TCOF1 (includes EG:6949) | 202385_s_at | 1.169 |
| TFB1M | 228075_x_at | 0.87 |
| THRAP3 | 217847_s_at | 1.464 |
| TIMM23 | 218119_at | 0.723 |
| TM6SF1 | 1558102_at | 0.704 |
| TMEM126B | 221622_s_at | 0.843 |
| TMEM165 | 1560622_at | 1.756 |
| TMEM30A | 232591_s_at | 0.771 |
| TNFAIP1 | 201207_at | 0.88 |
| TNPO1 | 1556116_s_at | 1.739 |
| TNRC6A | 234734_s_at | 1.268 |
| TOX4 | 201685_s_at | 0.73 |
| TPM4 | 235094_at | 2.079 |
| TRAPPC2 | 219351_at | 0.821 |
| TRAPPC2L | 218354_at | 0.837 |
| TRIM33 | 239716_at | 2.496 |
| TRIM46 | 238147_at | 1.96 |
| TRIO | 240773_at | 2.607 |
| TRNT1 | 243236_at | 2.295 |
| TRPV1 | 1556229_at | 2.636 |
| TSPAN31 | 203227_s_at | 0.744 |
| TTC26 | 233999_s_at | 1.184 |
| TTC3 | 208664_s_at | 1.396 |
| TTC9C | 1569189_at | 1.55 |
| TTLL4 | 1557611_at | 2.092 |
| TXNDC12 | 223017_at | 0.849 |
| TXNL1 | 243664_at | 1.98 |
| UBE2E3 | 210024_s_at | 0.758 |
| UBE3C | 1560739_a_at | 0.815 |
| UBXD7 | 212840_at | 0.754 |
| UGT1A6 | 206094_x_at | 3.86 |
| UNK | 1562434_at | 1.637 |
| UQCC | 229672_at | 1.451 |
| USP36 | 224979_s_at | 1.393 |
| USP8 | 229501_s_at | 0.808 |
| VPS37B | 236889_at | 2.85 |
| VTI1B | 209452_s_at | 0.821 |
| WDR41 | 218055_s_at | 0.789 |
| WDR68 | 233782_at | 1.924 |
| WFS1 | 1555270_a_at | 1.315 |
| WIPF2 | 216006_at | 2.916 |
| WTAP | 1560274_at | 1.747 |
| XRCC5 | 232633_at | 2.106 |
| YY1 | 224711_at | 0.821 |
| ZFHX3 | 215828_at | 1.737 |
| ZFR | 238970_at | 2.655 |
| ZFX | 207920_x_at | 1.625 |
| ZMYND8 | 209049_s_at | 1.102 |
| ZNF154 | 242170_at | 2.667 |
| ZNF224 | 216983_s_at | 2.986 |
| ZNF226 | 219603_s_at | 1.332 |
| ZNF251 | 226754_at | 1.313 |
| ZNF292 | 236435_at | 3.201 |
| ZNF326 | 241720_at | 1.418 |
| ZNF337 | 1565614_at | 2.096 |
| ZNF536 | 233890_at | 3.303 |
| ZNF567 | 242429_at | 2.103 |
| ZNF618 | 226590_at | 0.75 |
| ZNF668 | 219047_s_at | 0.691 |
| ZNF800 | 227101_at | 1.484 |
| ZUFSP | 228330_at | 1.205 |

TABLE 6

Differentially expressed genes between ABCB5+ and ABCB5− cells as detected by RT-PCR. PCR Array Catalog #: PAHS-024

| Position | Unigene | Refseq | Symbol | Description | Gname | ABCB5+/ABCB5− Fold change |
|---|---|---|---|---|---|---|
| A01 | Hs.525622 | NM_005163 | AKT1 | V-akt murine thymoma viral oncogene homolog 1 | AKT/PKB | 1.2687 |
| A02 | Hs.369675 | NM_001146 | ANGPT1 | Angiopoietin 1 | AGP1/AGPT | 1.2953 |
| A03 | Hs.583870 | NM_001147 | ANGPT2 | Angiopoietin 2 | AGPT2/ANG2 | 2.7007 |
| A04 | Hs.209153 | NM_014495 | ANGPTL3 | Angiopoietin-like 3 | ANGPT5 | 3.0596 |
| A05 | Hs.9613 | NM_001039667 | ANGPTL4 | Angiopoietin-like 4 | ANGPTL2/ARP4 | 1.6974 |

TABLE 6-continued

Differentially expressed genes between ABCB5+ and ABCB5− cells
as detected by RT-PCR. PCR Array Catalog #: PAHS-024

| Position | Unigene | Refseq | Symbol | Description | Gname | ABCB5+/ABCB5− Fold change |
|---|---|---|---|---|---|---|
| A06 | Hs.1239 | NM_001150 | ANPEP | Alanyl (membrane) aminopeptidase (aminopeptidase N, aminopeptidase M, microsomal aminopeptidase, CD13, p150) | APN/CD13 | 1.3597 |
| A07 | Hs.194654 | NM_001702 | BAI1 | Brain-specific angiogenesis inhibitor 1 | FLJ41988 | 3.0596 |
| A08 | Hs.54460 | NM_002986 | CCL11 | Chemokine (C-C motif) ligand 11 | SCYA11 | 1.8834 |
| A09 | Hs.303649 | NM_002982 | CCL2 | Chemokine (C-C motif) ligand 2 | GDCF-2/GDCF-2HC11 | 2.0326 |
| A10 | Hs.76206 | NM_001795 | CDH5 | Cadherin 5, type 2, VE-cadherin (vascular epithelium) | 7B4/CD144 | 3.0596 |
| A11 | Hs.517356 | NM_030582 | COL18A1 | Collagen, type XVIII, alpha 1 | KNO | 1.9634 |
| A12 | Hs.570065 | NM_000091 | COL4A3 | Collagen, type IV, alpha 3 (Goodpasture antigen) | TUMSTATIN | 2.1634 |
| B01 | Hs.789 | NM_001511 | CXCL1 | Chemokine (C-X-C motif) ligand 1 (melanoma growth stimulating activity, alpha) | FSP/GRO1 | 1.2086 |
| B02 | Hs.632586 | NM_001565 | CXCL10 | Chemokine (C-X-C motif) ligand 10 | C7/IFI10 | −2.1987 |
| B03 | Hs.89690 | NM_002090 | CXCL3 | Chemokine (C-X-C motif) ligand 3 | CINC-2b/GRO3 | 2.061 |
| B04 | Hs.89714 | NM_002994 | CXCL5 | Chemokine (C-X-C motif) ligand 5 | ENA-78/SCYB5 | 1.8834 |
| B05 | Hs.164021 | NM_002993 | CXCL6 | Chemokine (C-X-C motif) ligand 6 (granulocyte chemotactic protein 2) | CKA-3/GCP-2 | 2.1936 |
| B06 | Hs.77367 | NM_002416 | CXCL9 | Chemokine (C-X-C motif) ligand 9 | CMK/Humig | −1.1225 |
| B07 | Hs.592212 | NM_001953 | TYMP | Thymidine phosphorylase | ECGF1/MNGIE | 1.5837 |
| B08 | Hs.154210 | NM_001400 | EDG1 | Endothelial differentiation, sphingolipid G-protein-coupled receptor, 1 | CHEDG1/D1S3362 | 1.0377 |
| B09 | Hs.516664 | NM_182685 | EFNA1 | Ephrin-A1 | B61/ECKLG | 1.4573 |
| B10 | Hs.516656 | NM_004952 | EFNA3 | Ephrin-A3 | EFL2/EPLG3 | 1.3692 |
| B11 | Hs.149239 | NM_004093 | EFNB2 | Ephrin-B2 | EPLG5/HTKL | 1.1355 |
| B12 | Hs.419815 | NM_001963 | EGF | Epidermal growth factor (beta-urogastrone) | HOMG4/URG | 187.8365 |
| C01 | Hs.76753 | NM_000118 | ENG | Endoglin (Osler-Rendu-Weber syndrome 1) | CD105/END | 1.1514 |
| C02 | Hs.437008 | NM_004444 | EPHB4 | EPH receptor B4 | HTK/MYK1 | 1.3692 |
| C03 | Hs.115263 | NM_001432 | EREG | Epiregulin | ER | 1.8834 |
| C04 | Hs.483635 | NM_000800 | FGF1 | Fibroblast growth factor 1 (acidic) | AFGF/ECGF | 1.5511 |
| C05 | Hs.284244 | NM_002006 | FGF2 | Fibroblast growth factor 2 (basic) | BFGF/FGFB | 1.1355 |
| C06 | Hs.1420 | NM_000142 | FGFR3 | Fibroblast growth factor receptor 3 (achondroplasia, thanatophoric dwarfism) | ACH/CD333 | 1.7092 |
| C07 | Hs.11392 | NM_004469 | FIGF | C-fos induced growth factor (vascular endothelial growth factor D) | VEGF-D/VEGFD | 3.5884 |
| C08 | Hs.654360 | NM_002019 | FLT1 | Fms-related tyrosine kinase 1 (vascular endothelial growth factor/vascular permeability factor receptor) | FLT/VEGFR1 | 2.4172 |

TABLE 6-continued

Differentially expressed genes between ABCB5+ and ABCB5− cells
as detected by RT-PCR. PCR Array Catalog #: PAHS-024

| Position | Unigene | Refseq | Symbol | Description | Gname | ABCB5+/ABCB5− Fold change |
|---|---|---|---|---|---|---|
| C09 | Hs.388245 | NM_021973 | HAND2 | Heart and neural crest derivatives expressed 2 | DHAND2/Hed | 2.0186 |
| C10 | Hs.396530 | NM_000601 | HGF | Hepatocyte growth factor (hepapoietin A; scatter factor) | F-TCF/HGFB | 4.542 |
| C11 | Hs.654600 | NM_001530 | HIF1A | Hypoxia-inducible factor 1, alpha subunit (basic helix-loop-helix transcription factor) | HIF-1alpha/HIF1 | −1.0918 |
| C12 | Hs.44227 | NM_006665 | HPSE | Heparanase | HPA/HPR1 | 286.6871 |
| D01 | Hs.504609 | NM_002165 | ID1 | Inhibitor of DNA binding 1, dominant negative helix-loop-helix protein | ID | −1.0329 |
| D02 | Hs.76884 | NM_002167 | ID3 | Inhibitor of DNA binding 3, dominant negative helix-loop-helix protein | HEIR-1 | −1.3535 |
| D03 | Hs.37026 | NM_024013 | IFNA1 | Interferon, alpha 1 | IFL/IFN | 1.8834 |
| D04 | Hs.93177 | NM_002176 | IFNB1 | Interferon, beta 1, fibroblast | IFB/IFF | 1.8834 |
| D05 | Hs.856 | NM_000619 | IFNG | Interferon, gamma | IFG/IFI | 1.8834 |
| D06 | Hs.160562 | NM_000618 | IGF1 | Insulin-like growth factor 1 (somatomedin C) | IGFI | 4.7022 |
| D07 | Hs.126256 | NM_000576 | IL1B | Interleukin 1, beta | IL-1/IL1-BETA | 2.0898 |
| D08 | Hs.654458 | NM_000600 | IL6 | Interleukin 6 (interferon, beta 2) | BSF2/HGF | 1.7331 |
| D09 | Hs.624 | NM_000584 | IL8 | Interleukin 8 | 3-10C/AMCF-I | 1.1674 |
| D10 | Hs.436873 | NM_002210 | ITGAV | Integrin, alpha V (vitronectin receptor, alpha polypeptide, antigen CD51) | CD51/DKFZp686A08142 | 1.217 |
| D11 | Hs.218040 | NM_000212 | ITGB3 | Integrin, beta 3 (platelet glycoprotein IIIa, antigen CD61) | CD61/GP3A | −1.0619 |
| D12 | Hs.224012 | NM_000214 | JAG1 | Jagged 1 (Alagille syndrome) | AGS/AHD | 1566.5046 |
| E01 | Hs.479756 | NM_002253 | KDR | Kinase insert domain receptor (a type III receptor tyrosine kinase) | CD309/FLK1 | 1.234 |
| E02 | Hs.473256 | NM_005560 | LAMA5 | Laminin, alpha 5 | KIAA1907 | 3.8727 |
| E03 | Hs.421391 | NM_007015 | LECT1 | Leukocyte cell derived chemotaxin 1 | BRICD3/CHM-I | 1.8834 |
| E04 | Hs.194236 | NM_000230 | LEP | Leptin | OB/OBS | 2.1485 |
| E05 | Hs.82045 | NM_002391 | MDK | Midkine (neurite growth-promoting factor 2) | MK/NEGF2 | 1.4573 |
| E06 | Hs.513617 | NM_004530 | MMP2 | Matrix metallopeptidase 2 (gelatinase A, 72 kDa gelatinase, 72 kDa type IV collagenase) | CLG4/CLG4A | 1.674 |
| E07 | Hs.297413 | NM_004994 | MMP9 | Matrix metallopeptidase 9 (gelatinase B, 92 kDa gelatinase, 92 kDa type IV collagenase) | CLG4B/GELB | 1.9097 |
| E08 | Hs.436100 | NM_004557 | NOTCH4 | Notch homolog 4 (Drosophila) | INT3/NOTCH3 | 1.2002 |
| E09 | Hs.131704 | NM_003873 | NRP1 | Neuropilin 1 | CD304/DKFZp686A03134 | 1.1755 |
| E10 | Hs.471200 | NM_003872 | NRP2 | Neuropilin 2 | NP2/NPN2 | 1.4373 |
| E11 | Hs.707991 | NM_002607 | PDGFA | Platelet-derived growth factor alpha polypeptide | PDGF-A/PDGF1 | 1.2002 |
| E12 | Hs.514412 | NM_000442 | PECAM1 | Platelet/endothelial cell adhesion molecule (CD31 antigen) | CD31/PECAM-1 | 11.9037 |
| F01 | Hs.81564 | NM_002619 | PF4 | Platelet factor 4 (chemokine (C-X-C motif) ligand 4) | CXCL4/SCYB4 | 2.9966 |
| F02 | Hs.252820 | NM_002632 | PGF | Placental growth factor, vascular endothelial growth factor-related protein | D12S1900/PGFL | −1.1865 |
| F03 | Hs.77274 | NM_002658 | PLAU | Plasminogen activator, urokinase | ATF/UPA | 1.6396 |

TABLE 6-continued

Differentially expressed genes between ABCB5+ and ABCB5− cells as detected by RT-PCR. PCR Array Catalog #: PAHS-024

| Position | Unigene | Refseq | Symbol | Description | Gname | ABCB5+/ABCB5− Fold change |
|---|---|---|---|---|---|---|
| F04 | Hs.143436 | NM_000301 | PLG | Plasminogen | DKFZp779M0222 | 1.8834 |
| F05 | Hs.125036 | NM_020405 | PLXDC1 | Plexin domain containing 1 | DKFZp686F0937/TEM3 | 3.4184 |
| F06 | Hs.528665 | NM_021935 | PROK2 | Prokineticin 2 | BV8/KAL4 | 1.8446 |
| F07 | Hs.201978 | NM_000962 | PTGS1 | Prostaglandin-endoperoxide synthase 1 (prostaglandin G/H synthase and cyclooxygenase) | COX1/COX3 | 1.2086 |
| F08 | Hs.532768 | NM_002615 | SERPINF1 | Serpin peptidase inhibitor, clade F (alpha-2 antiplasmin, pigment epithelium derived factor), member 1 | EPC-1/PEDF | 1.1121 |
| F09 | Hs.68061 | NM_021972 | SPHK1 | Sphingosine kinase 1 | SPHK | 1.192 |
| F10 | Hs.301989 | NM_015136 | STAB1 | Stabilin 1 | CLEVER-1/FEEL-1 | 4.357 |
| F11 | Hs.89640 | NM_000459 | TEK | TEK tyrosine kinase, endothelial (venous malformations, multiple cutaneous and mucosal) | CD202B/TIE-2 | −1.2805 |
| F12 | Hs.170009 | NM_003236 | TGFA | Transforming growth factor, alpha | TFGA | 3549.3357 |
| G01 | Hs.645227 | NM_000660 | TGFB1 | Transforming growth factor, beta 1 | CED/DPD1 | 1.1837 |
| G02 | Hs.133379 | NM_003238 | TGFB2 | Transforming growth factor, beta 2 | TGF-beta2 | 1.3787 |
| G03 | Hs.494622 | NM_004612 | TGFBR1 | Transforming growth factor, beta receptor I (activin A receptor type II-like kinase, 53 kDa) | AAT5/ACVRLK4 | 1.7695 |
| G04 | Hs.164226 | NM_003246 | THBS1 | Thrombospondin 1 | THBS/TSP | −1.0619 |
| G05 | Hs.371147 | NM_003247 | THBS2 | Thrombospondin 2 | TSP2 | −1.203 |
| G06 | Hs.522632 | NM_003254 | TIMP1 | TIMP metallopeptidase inhibitor 1 | CLGI/EPA | −1.1147 |
| G07 | Hs.633514 | NM_003255 | TIMP2 | TIMP metallopeptidase inhibitor 2 | CSC-21K | 1.2864 |
| G08 | Hs.701968 | NM_000362 | TIMP3 | TIMP metallopeptidase inhibitor 3 (Sorsby fundus dystrophy, pseudoinflammatory) | HSMRK222/K222 | 1.8834 |
| G09 | Hs.241570 | NM_000594 | TNF | Tumor necrosis factor (TNF superfamily, member 2) | DIF/TNF-alpha | 4.0652 |
| G10 | Hs.525607 | NM_006291 | TNFAIP2 | Tumor necrosis factor, alpha-induced protein 2 | B94 | 1.8834 |
| G11 | Hs.73793 | NM_003376 | VEGFA | Vascular endothelial growth factor A | VEGF/VEGF-A | 2.4509 |
| G12 | Hs.435215 | NM_005429 | VEGFC | Vascular endothelial growth factor C | Flt4-L/VRP | 446.7529 |
| H01 | Hs.534255 | NM_004048 | B2M | Beta-2-microglobulin | B2M | −1.2983 |
| H02 | Hs.412707 | NM_000194 | HPRT1 | Hypoxanthine phosphoribosyltransferase 1 (Lesch-Nyhan syndrome) | HGPRT/HPRT | −1.2894 |
| H03 | Hs.523185 | NM_012423 | RPL13A | Ribosomal protein L13a | RPL13A | 1.1837 |
| H04 | Hs.544577 | NM_002046 | GAPDH | Glyceraldehyde-3-phosphate dehydrogenase | G3PD/GAPD | −1.146 |
| H05 | Hs.520640 | NM_001101 | ACTB | Actin, beta | PS1TP5BP1 | −1.0329 |
| H06 | N/A | SA_00105 | HGDC | Human Genomic DNA Contamination | HIGX1A | 1.8834 |
| H07 | N/A | SA_00104 | RTC | Reverse Transcription Control | RTC | 1.7451 |
| H08 | N/A | SA_00104 | RTC | Reverse Transcription Control | RTC | 1.7451 |
| H09 | N/A | SA_00104 | RTC | Reverse Transcription Control | RTC | 1.7695 |
| H10 | N/A | SA_00103 | PPC | Positive PCR Control | PPC | 1.8067 |
| H11 | N/A | SA_00103 | PPC | Positive PCR Control | PPC | 1.7818 |
| H12 | N/A | SA_00103 | PPC | Positive PCR Control | PPC | 36695.9527 |

Example 3

We therefore tested the hypothesis that MMIC, as defined by the novel marker ABCB5[3], specifically relate to the phenomenon of vasculogenic mimicry whereby melanoma cells form channels capable of conducting nutrients from peripheral blood and thus serving as surrogates for mature tumour vessels[4]. Because we posited that this phenomenon may be more robust during early stages of tumour formation before cancer angiogenesis fully develops, we evaluated experimentally-induced human-derived melanomas grown as tumour xenografts in the subcutis of immunodeficient mice and in the dermis of human skin xenografted to immunodeficient mice (FIG. 2), the latter a humanized model whereby human melanoma develops in the context of the human stromal microenvironment[13]. While only peripheral tumour vessels expressed the mature endothelial marker, CD31, more interior regions of the melanomas exhibited formation of CD31-negative anastomosing channels with histologic, histochemical (PAS-D and laminin reactivity), and ultrastructural findings consistent with established features of vasculogenic mimicry[4] (FIG. 2a-d). By electron microscopy, lumen-like spaces in these regions were lined by basement membrane-like material and viable melanoma cells and contained erythrocytes surrounded by finely granular matrix consistent with plasma, suggesting communication with the systemic circulation[4]. By immunohistochemistry and in situ hybridization, channels expressed ABCB5 protein and mRNA, respectively (FIG. 2f-h), which also correlated in vitro when assayed across a panel of human melanoma cell lines (FIG. 4), and the architecture of ABCB5[+] channels in xenografted tumours was identical to that focally detected in patient-derived melanomas (FIG. 2f, inset). An identical pattern was also observed for CD133 mRNA (not illustrated), an additional marker for tumourigenic melanoma cells[14] and melanoma progression[15]. Anti-ABCB5 mAb systemically administered in vivo localized to channels, further confirming their systemic perfusion as well as the intimate association of ABCB5[+] melanoma cells with channel lumens (FIG. 2i). Double-labeling demonstrated co-localization of the human endothelial markers CD144 and TIE-1 with ABCB5[+] cells forming channels (FIG. 2j,k). Tumours initiated by melanoma cell lines expressing the green fluorescence protein (GFP) transgene confirmed the presence of melanoma cells lining channels that co-expressed melanoma-associated GFP and CD144 (FIG. 2e), as well as human melanoma—but not human xenograft-associated class I major histocompatibility complex (MHC) antigens (not illustrated). These data show that the formation of perfused vessel-like channels in human melanoma is mediated by the ABCB5[+] MMIC subpopulation found to selectively display gene profiles and differentiation capacity consistent with its participation in tumour vasculogenesis.

Example 4

We next reasoned that if vasculogenic channel formation mediated by ABCB5[+] MMIC was functionally required for their capacity to efficiently initiate and drive melanoma growth, depletion of MMIC to low levels should inhibit the melanoma-associated vasculogenic response. To evaluate tumourigenesis and vasculogenesis in a bioassay most relevant to human primary melanoma, we again utilized a human skin/murine xenograft model whereby melanomas develop in the relevant dermal microenvironment of human skin and express architectural features and evolutionary growth patterns more akin to naturally occurring lesions[13]. Intradermal orthotopic transplantation of $2 \times 10^6$ unsegregated A375 cutaneous melanoma cells (ABCB5 positivity: 5.2±5.1%; mean±s.e.m., n=9) (FIG. 3a) or heterotopic transplantation of $2 \times 10^6$ unsegregated uveal melanoma cells previously assayed for vasculogenic differentiation[4,16] (MUM-2B and MUM-2C, ABCB5 positivity: 2.46±0.46% and 3.81±1.04%, respectively; mean±s.e.m., n=3-4) (FIG. 3a) to human skin resulted in tumour formation three weeks following microinjections in 14 of 14 recipient skin grafts (A375: n=6, MUM-2B: n=4, MUM-2C: n=4 replicates) when assessed histologically in serial sections of each human skin xenograft in its entirety (FIG. 3b,c). In contrast, intradermal transplantation of equal numbers of ABCB5[+]-depleted melanoma cells resulted in histologically-assessed tumour formation in only 6 of 14 recipient skin grafts (P<0.002) (FIG. 3b,c) and histologically-determined mean tumour volumes (TV) were significantly reduced in recipients of ABCB5[+]-depleted vs. unsegregated melanoma inocula (TV=2.8±1.8 mm$^3$ vs. 10.9±6.9 mm$^3$, respectively; mean±s.e.m., P<0.005) (FIG. 3d). When vasculogenic channel formation within tumours was evaluated using quantitative image analysis technology to assess the pixilated density of laminin immunoreactivity, significantly fewer channels per cross-sectional area were detected in tumours that formed from MMIC-depleted inocula compared to those that originated from unsegregated tumour cell grafts (A375, P<0.0032; MUM-2B, P<0.0005; MUM-2C, P<0.0059) (FIG. 3e,f). In aggregate, these findings show in relevant xenograft models of early melanoma development the participation of ABCB5[+] MMIC in the genesis of vasculogenic channels, and the interdependency of MMIC-derived channel formation and tumour growth.

Discovery of MMIC-driven vasculogenesis identifies selective differentiation plasticity as a novel CSC-specific function through which these tumourigenic cancer subpopulations may provide a specific growth advantage to developing tumours. Our finding of a propensity of MMIC to differentiate selectively into cells capable of serving a defined tissue function required for more efficient tumour growth parallels hallmark characteristics of physiological stem cells, which similarly give rise to cell lineages capable of serving specific roles required for maintenance of tissue homeostasis through defined differentiation programs. Importantly, we find that MMIC-dependent tumourigenesis and vasculogenesis are operative not only in human melanoma to murine skin xenotransplantation models but also upon human melanoma to human skin transplantation. Therefore, our results provide initial evidence that the tumour-sustaining role of human CSC identified in xenotransplantation assays does not merely reflect the limited ability of human tumour cells to adapt to growth in a foreign (mouse) milieu, as has been postulated based on the results of murine tumour transplantation experiments utilizing histocompatible murine hosts[17]

The now widely-accepted concept of cancer angiogenesis advanced by Folkman in 1971 states that human cancers are critically dependent upon tumour-related blood-vessel growth and development[18]. In addition to classical angiogenesis whereby cancer cells, including CSC[19], induce in-growth of mature, CD31-positive vessels from surrounding stroma[20], evidence has been generated that cancer cells may also directly form surrogate vessel-like spaces by the process of vasculogenic mimicry whereby aggressive human melanomas develop patterned networks composed of periodic acid-Schiff (PAS)- and laminin-reactive basement membranes and associated perfusable channels formed by tumour cells that express some but not all endotheliumrelated genes and proteins[4]. The present study identifies the cells and underlying mechanisms responsible for vasculogenic mimicry, and establishes that in addition to self-renewal, MMIC selectively express vasculogenic genes and form channels consistent with the function of promoting nutrition to rapidly growing tumours. Thus, cancer angiogenesis and MMIC-driven vasculogenesis may represent independent yet potentially interrelated mechanisms whereby aggressive and metabolically-active tumours obtain those nutrients requisite for critical stages of growth and evolution. This may be particularly important during tumour initiation and early phases of tumourigenic growth when hypoxia-dependent, mTOR-driven angiogenesis from surrounding stroma has not fully evolved[21].

Recently, proof-of-principle has been established for the potential therapeutic utility of the CSC concept[3,22]. Therefore, identification of a vasculogenic mechanism whereby MMIC may contribute to tumour growth has potentially important therapeutic implications. Previous studies revealed that normally resistant human melanoma cells are rendered sensitive in vitro to the effects of chemotherapeutic agents by mAb- or siRNA-mediated blockade of ABCB5[5,6], and that mAb binding to ABCB5 is sufficient to induce an effective anti-melanoma immune response via antibody-dependent cell-mediated cytotoxicity (ADCC) in vivo[3]. Now, recognition of the role of MMIC in tumour vasculogenesis will also permit development of strategies focused on inhibition of the relevant molecular pathways integral to endothelial-directed CSC plasticity. Moreover, the spatial localization of the MMIC component to channels that communicate with the systemic circulation may render this important determinant of cancer virulence particularly vulnerable to therapeutic targeting.

Example 5: Vasculogenic/Angiogenic Pathways in Human Melanoma

We investigated gene relationships based on Ingenuity Pathway Analysis. We prepared a graphical representation of pathway activation across ABCB5+ MMIC. Genes that were overexpressed in ABCB5+ relative to ABCB5− human melanoma cells were represented by red nodes (circles) and those expressed at lower levels were represented by black nodes. Black lines were drawn between genes to show known interactions. Known gene functions in vasculogenesis and angiogenesis, and genes known as relevant drug targets were annotated (red lines) (FIG. 1a). We examined expression of vasculogenic/angiogenic pathway members by RT-PCR in ABCB5+ MMIC. Results of this anaylsis are shown in FIG. 1b. We used dual color flow cytometry using ABCB5 phenotype-specific cell gating to determining FLT1 (VEGFR-1) protein expression of ABCB5+ MMIC (FIG. 1c, top) and ABCB5-melanoma cells (FIG. 1c, bottom). We examined CD144 expression in ABCB5+ MMIC or ABCB5− melanoma cell subpopulations by immunofluorescence staining prior to (t=0 h) and upon 48 h of culture (t=48 h) in the presence of 100 ng/ml VEGF[11]. Representative immunofluorescence staining for CD144 expression (Texas red) are shown in FIG. 1d, with nuclei counterstained in blue (DAPI). Mean percentages (mean±s.e.m., n=3 replicate experiments) of cells staining positively for CD144 in each sample are shown on the right. We examined CD144 expression in melanoma cells in the presence of 100 ng/ml VEGF as in above, but in the presence or absence of anti-FLT1 (VEGFR-1) blocking mAb or isotype control mAb. Representative immunofluorescence staining for CD144 expression (Texas red) by melanoma cells cultured for 48 h (t=48 h) are shown in FIG. 1e, with nuclei counterstained in blue (DAPI). Mean percentages (mean±s.e.m., n=3 replicate experiments) of cells staining positively for CD144 in each sample are shown in the far right panel. We examined tube formation by phase contrast light microscopy of melanoma cells cultured for 24 h (t=24 h) in the presence of 100 ng/ml VEGF and the presence or absence of anti-FLT1 (VEGFR-1) blocking mAb or isotype control mAb (FIG. 1f). Number of tubes/microscopy field (mean±s.e.m., n=3 replicate experiments) and tube length (μm) (mean±s.e.m., n=3 replicate experiments) are illustrated for the different experimental conditions on the far right panels, respectively. We examined the differentiation potential of ABCB5+ and ABCB5− human melanoma cells along a adipogenic pathway (FIG. 1h, Oil Red O staining, nuclei are counterstained with hematoxylin) and osteogenic pathway (FIG. 1i, Alizarin Red staining). Myogenic differentiation potential of ABCB5+ and ABCB5− human melanoma cells was also examined (FIG. 1j). Absence of myogenin staining (FITC, green) was detected in ABCB5+ or ABCB5− human melanoma cells (nuclei are counterstained with DAPI).

Example 6: MMIC-Driven In Vivo Vasculogenesis

We investigated MMIC driven vasculogenesis in vivo. Sections of human melanoma growing at melanoma cell injection site within human dermis of skin xenograft to NOD/SCID mouse were conventionally-stained by hematoxylin and eosin (FIG. 2a). We also examined by immunohistochemistry the expression of human CD31 which indicated angiogenic response at perimeter of melanoma within human xenograft. (FIG. 2b, broken line represents interface of tumour nodule with dermal connective tissue). We used periodic-acid Schiff (PAS) stain (with diastase), an immunochemical stain of CD31-negative interior regions of melanoma xenografts, to reveal numerous anastomosing channels (FIG. 2c, inset is laminin immunohistochemistry indicating identical pattern). We conducted transmission electron micrographs of interior regions of melanoma xenografts (FIG. 2d), and found that lumenal spaces containing blood products (erythrocytes) are lined by melanoma cells and associated basement membrane-like extracellular matrix. We examined the interior zone of melanoma xenograft derived from cells expressing GFP transgene and immunohistochemically stained for endothelial marker CD144 (red chromogen); results are shown in (FIG. 2e). We found that CD144 expression is confined to cells forming lumen-like spaces lined by cells that co-express GFP and CD144 (indicated as yellow-orange). We also performed immunohistochemistry, at low (FIG. 2f) and high (FIG. 2g) magnification, for ABCB5 protein; our results show that reactivity is restricted to anastomosing channels identical to those seen in FIG. 2c. The inset in FIG. 2f depicts similar formation of ABCB5-reactive channels in a patient-derived melanoma biopsy. We performed in situ hybridization for ABCB5 mRNA (FIG. 2h). Our results reveal a channel pattern corresponding to that of ABCB5 protein expression (compare with FIG. 2f; inset is sense control). We examined the expression of ABCB5 in melanoma xenografts after intravenous administration in vivo (FIG. 2h). Detection of anti-ABCB5 mAb was accomplished using anti-mouse Ig immunohistochemistry; note localization to channels (inset represents anti-mouse Ig staining after intravenous administration of irrelevant isotype-matched control mAb). Dual-labeling immunofluorescence microscopy was performed for both ABCB5 (green), CD144 (red), and ABCB5 &

CD144 (mix) (FIG. 2j) and ABCB5 (green), TIE-1 (red), and ABCB5 & TIE-1 (mix) (FIG. 2j).

Example 7: Interdependency of MMIC-Driven Vasculogenesis and Tumourigenesis

We examined ABCB5 expression by flow cytometry; ABCB5 or control staining (FITC, F11) was plotted against forward scatter (FSC) for human A375, MUM-2B, and MUM-2C melanoma cell inocula. Representative data is shown in FIG. 3a. We examined histologic sections of melanomas that developed from three unsegregated and ABCB5-depleted melanoma cell lines injected intradermally into human skin xenografts. Representative sections are shown in FIG. 3b. We used histology to determine tumour formation rate (%) 3 weeks following intradermal transplantation of unsegregated vs. ABCB5$^+$-depleted human A375, MUM-2B or MUM-2C melanoma cells ($2\times10^6$/inoculum) into human skin/Rag2$^{-/-}$ chimeric mice (n=5, respectively). (FIG. 3c). We determined histological tumour volumes (mean±s.e.m.) 3 weeks following intradermal transplantation of unsegregated vs. ABCB5$^+$-depleted human A375, MUM-2B or MUM-2C melanoma cells ($2\times10^6$/inoculum) into human skin/Rag2$^{-/-}$ chimeric mice. (FIG. 3d). We performed immunohistochemistry for laminin. Our results showed the extent of channel formation in melanomas that developed from unsegregated or ABCB5$^+$-depleted melanoma cell inocula derived from A375, MUM-2B or MUM-2C lines injected intradermally into human skin xenografts (arrows=necrosis). (FIG. 3e). We performed image analysis of laminin immunoreactivity for melanomas derived from unsegregated and ABCB5$^+$-depleted cell inocula. Data are shown in FIG. 3f; y-axis is percent of pixelated area with reactivity (mean±s.e.m.); solid bar represents tumours derived from unsegregated melanoma cells, open bars represent tumours derived from ABCB5$^+$-depleted cells (A375, P<0.0032; MUM-2B, P<0.0005; MUM-2C, P<0.0059).

Example 8: Correlation of ABCB5 Protein and mRNA Expression Across Human Melanoma Cell Lines We examined ABCB5 and tubulin expression in a panel of human melanoma cell lines by western blot analysis (FIG. 4a). We examined relative ABCB5 mRNA expression (log 2) in a panel of human melanoma cell lines plotted against ABCB5 protein expression as determined by ratios of ABCB5 89 kD western blot band intensity and tubulin western blot band intensity for each human melanoma cell line. (FIG. 4b). Data points are as follows: 1, SK-MEL-2; 2, SK-MEL-5; 3, SK-MEL-28; 4, MDA-MB-435; 5, UACC-62; 6, UACC-257; 7, M14; 8, MALME-3M. Spearman Rank Correlation r (corrected for ties).

Example 9: CSC-Associated Genes Identified at the Protein Level

Using cell surface immunostaining and flow cytometry we identified additional genes to be differentially regulated at the protein level in ABCB5+ CSC versus ABCB5− cancer bulk populations. These are all immunomodulatory molecules and the ones upregulated in ABCB5+ cells may be relevant to the escape from immunosurveillance and be respoisble for resistance to immunotherapy in malignant melanoma, i.e. when the genes overexpressed on ABCB5+ cells are targeted, melanoma is predicted to be sensitized to immune attack and therapy.

TABLE 8

Upregulated in ABCB5+ CSC compared to ABCB5− bulk cancer populations:

MHC class II
CD28
CD86
PD-1
CD40-L
4-1BB-L
B7-H4
GITR

TABLE 7

Downregulated in ABCB5+ CSC compared to ABCB5− cancer bulk populations

MHC class I
CD80
PD-L1
ICOS-L

REFERENCES FOR DETAILED DESCRIPTION AND EXAMPLES

1 M. Al-Hajj, M. S. Wicha, A. Benito-Hernandez et al., *Proc Natl Acad Sci USA* 100 (7), 3983 (2003); D. Bonnet and J. E. Dick, *Nat Med* 3 (7), 730 (1997); C. A. O'Brien, A. Pollett, S. Gallinger et al., *Nature* 445 (7123), 106 (2007); L. Ricci-Vitiani, D. G. Lombardi, E. Pilozzi et al., *Nature* 445 (7123), 111 (2007); S. K. Singh, C. Hawkins, I. D. Clarke et al., *Nature* 432 (7015), 396 (2004).
2 T. Schatton and M. H. Frank, *Pigment cell & melanoma research* 21 (1), 39 (2008).
3 T. Schatton, G. F. Murphy, N. Y. Frank et al., *Nature* 451 (7176), 345 (2008).
4 A. J. Maniotis, R. Folberg, A. Hess et al., *Am J Pathol* 155 (3), 739 (1999).
5 N. Y. Frank, A. Margaryan, Y. Huang et al., *Cancer Res* 65 (10), 4320 (2005).
6 Y. Huang, P. Anderle, K. J. Bussey et al., *Cancer Res* 64 (12), 4294 (2004).
7 L. Chin, L. A. Garraway, and D. E. Fisher, *Genes Dev* 20 (16), 2149 (2006).
8 G. I. Keshet, I. Goldstein, O. Itzhaki et al., *Biochem Biophys Res Commun* 368 (4), 930 (2008).
9 J. F. Sousa and E. M. Espreafico, *BMC cancer* 8, 19 (2008).
10 N. Y. Frank, A. T. Kho, T. Schatton et al., *J Cell Biol* 175 (1), 99 (2006).
11 K. Nishiyama, K. Takaji, Y. Uchijima et al., *J Biol Chem* 282 (23), 17200 (2007).
12 D. Fang, T. K. Nguyen, K. Leishear et al., *Cancer Res* 65 (20), 9328 (2005).
13 I. Juhasz, S. M. Albelda, D. E. Elder et al., *Am J Pathol* 143 (2), 528 (1993).
14 E. Monzani, F. Facchetti, E. Galmozzi et al., *Eur J Cancer* 43 (5), 935 (2007).
15 W. M. Klein, B. P. Wu, S. Zhao et al., *Mod Pathol* 20 (1), 102 (2007).
16 E. A. Seftor, P. S. Meltzer, D. A. Kirschmann et al., *Clin Exp Metastasis* 19 (3), 233 (2002).
17 P. N. Kelly, A. Dakic, J. M. Adams et al., *Science* 317 (5836), 337 (2007).
18 J. Folkman, *N Engl J Med* 285 (21), 1182 (1971).

19 S. Bao, Q. Wu, S. Sathornsumetee et al., *Cancer Res* 66 (16), 7843 (2006); R. J. Gilbertson and J. N. Rich, *Nat Rev Cancer* 7 (10), 733 (2007).
20 B. N. Perry and J. L. Arbiser, *J Invest Dermatol* 126 (10), 2160 (2006).
21 M. Guba, P. von Breitenbuch, M. Steinbauer et al., *Nat Med* 8 (2), 128 (2002).
22 Z. F. Yang, D. W. Ho, M. N. Ng et al., *Cancer Cell* 13 (2), 153 (2008); S. Bao, Q. Wu, Z. Li et al., *Cancer Res* 68 (15), 6043 (2008).
23 N. Y. Frank, S. S. Pendse, P. H. Lapchak et al., *J Biol Chem* 278 (47), 47156 (2003).
24 D. Donovan, N. J. Brown, E. T. Bishop et al., *Angiogenesis* 4 (2), 113 (2001).

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating an individual having, cancer, comprising:
   administering a therapeutically effective amount of a composition that targets a polypeptide encoded by a CSC-associated gene, wherein the composition is an isolated molecule that selectively binds to the polypeptide that is encoded by a CSC-associated gene and expressed on an ABCB5+ cancer stem cell of the individual, wherein the CSC-associated gene is Programmed Death-1 (PD-1), wherein the isolated molecule is conjugated to a therapeutic agent, and, wherein the isolated molecule is an antibody or antigen binding fragment, wherein the composition inhibits the activity of the ABCB5+ cancer stem cell, and wherein the cancer is a melanoma.

2. The method of claim 1, wherein the therapeutic agent is selected from: a toxin and a chemotherapeutic agent.

3. The method of claim 2, wherein the toxin is a radioisotope.

4. The method of claim 3, wherein the radioisotope is selected from the group consisting of: 225Ac, 211At, 212Bi, 213Bi, 186Rh, 188Rh, 177Lu, 90Y, 131I, 67Cu, 125I, 123I, 77Br, 153Sm, 166Bo, 64Cu, 212Pb, 224Ra and 223Ra.

5. The method of claim 3, wherein therapeutic agent is a chemotherapeutic agent.

6. The method of claim 1, wherein the antibody or antigen-binding fragment is a monoclonal antibody, human antibody, chimeric antibody, humanized antibody, a single-chain antibody, F(ab')2, Fab, Fd, Fv, or single-chain Fv fragment.

7. A method for treating an individual having, cancer, comprising:
   administering a therapeutically effective amount of a composition that targets a polypeptide encoded by a CSC-associated gene, wherein the composition is an isolated molecule that selectively binds to the polypeptide encoded by a CSC-associated gene and expressed on an ABCB5+ cancer stem cell of the individual, wherein the CSC-associated gene is Programmed Death-1 (PD-1), wherein the isolated molecule is conjugated to a therapeutic agent, wherein the isolated molecule is an antibody or antigen binding fragment, wherein the composition inhibits the activity of the ABCB5+ cancer stem cell, and wherein the individual has been diagnosed with cancer by a method comprising the steps of:
   (i) determining an expression level of a cancer stem cell (CSC)-associated gene on ABCB5+ cancer stem cell in a sample from an individual; wherein the CSC-associated gene is PD-1; and
   (ii) comparing the expression level of the CSC-associated gene to a reference value from non-cancer samples, wherein the higher expression of the CSC-associated gene on ABCB5+ cancer stem cell as compared to the reference value indicates a cancer.

8. A method for treating an individual having, cancer, comprising:
   administering a therapeutically effective amount of a composition that targets a polypeptide encoded by a CSC-associated gene, wherein the composition is an isolated molecule that selectively binds to the polypeptide encoded by a CSC-associated gene and expressed on an ABCB5+ stem cell of the individual, wherein the CSC-associated gene is Programmed Death-1 (PD-1), wherein the isolated molecule is conjugated to a therapeutic agent, and, wherein the isolated molecule is an antibody or antigen binding fragment, wherein the composition inhibits the activity of the ABCB5+ cancer stem cell, and wherein the cancer is an ABCB5+ stem cell cancer.

9. The method of claim 7, wherein the therapeutic agent is selected from: a toxin and a chemotherapeutic agent.

10. The method of claim 9, wherein the toxin is a radioisotope.

11. The method of claim 10, wherein the radioisotope is selected from the group consisting of: 225Ac, 211At, 212Bi, 213Bi, 186Rh, 188Rh, 177Lu, 90Y, 131I, 67Cu, 125I, 123I, 77Br, 153Sm, 166Bo, 64Cu, 212Pb, 224Ra and 223Ra.

12. The method of claim 9, wherein therapeutic agent is a chemotherapeutic agent.

13. The method of claim 7, wherein the antibody or antigen-binding fragment is a monoclonal antibody, human antibody, chimeric antibody, humanized antibody, a single-chain antibody, F(ab')2, Fab, Fd, Fv, or single-chain Fv fragment.

14. The method of claim 8, wherein the therapeutic agent is selected from: a toxin and a chemotherapeutic agent.

15. The method of claim 14, wherein the toxin is a radioisotope.

16. The method of claim 15, wherein the radioisotope is selected from the group consisting of: 225Ac, 211At, 212Bi, 213Bi, 186Rh, 188Rh, 177Lu, 90Y, 131I, 67Cu, 125I, 123I, 77Br, 153Sm, 166Bo, 64Cu, 212Pb, 224Ra and 223Ra.

17. The method of claim 14, wherein therapeutic agent is a chemotherapeutic agent.

18. The method of claim 8, wherein the antibody or antigen-binding fragment is a monoclonal antibody, human antibody, chimeric antibody, humanized antibody, a single-chain antibody, F(ab')2, Fab, Fd, Fv, or single-chain Fv fragment.

* * * * *